US011047008B2

(12) United States Patent
Emerson et al.

(10) Patent No.: US 11,047,008 B2
(45) Date of Patent: Jun. 29, 2021

(54) METHODS FOR DIAGNOSING INFECTIOUS DISEASE AND DETERMINING HLA STATUS USING IMMUNE REPERTOIRE SEQUENCING

(71) Applicants: Adaptive Biotechnologies Corporation, Seattle, WA (US); Fred Hutchinson Cancer Research Center, Seattle, WA (US)

(72) Inventors: Ryan O. Emerson, Seattle, WA (US); Harlan S. Robins, Seattle, WA (US); Mark Rieder, Seattle, WA (US); William Dewitt, III, Seattle, WA (US); Christopher Carlson, Seattle, WA (US)

(73) Assignees: Adaptive Biotechnologies Corporation, Seattle, WA (US); Fred Hutchinson Cancer Research Center, Seattle, WA (US)

( * ) Notice: Subject to any disclaimer, the term of this patent is extended or adjusted under 35 U.S.C. 154(b) by 859 days.

(21) Appl. No.: 15/553,040

(22) PCT Filed: Feb. 24, 2016

(86) PCT No.: PCT/US2016/019343
§ 371 (c)(1),
(2) Date: Aug. 23, 2017

(87) PCT Pub. No.: WO2016/138122
PCT Pub. Date: Sep. 1, 2016

(65) Prior Publication Data
US 2018/0037953 A1    Feb. 8, 2018

Related U.S. Application Data

(60) Provisional application No. 62/215,630, filed on Sep. 8, 2015, provisional application No. 62/157,249, filed on May 5, 2015, provisional application No. 62/120,249, filed on Feb. 24, 2015.

(51) Int. Cl.
C12Q 1/6881    (2018.01)
C12Q 1/68    (2018.01)
C12Q 1/70    (2006.01)
C12Q 1/6883    (2018.01)
C12Q 1/6869    (2018.01)

(52) U.S. Cl.
CPC .......... *C12Q 1/6881* (2013.01); *C12Q 1/68* (2013.01); *C12Q 1/6883* (2013.01); *C12Q 1/70* (2013.01); *C12Q 1/6869* (2013.01); *C12Q 2600/158* (2013.01); *C12Q 2600/172* (2013.01)

(58) Field of Classification Search
CPC ...... C12Q 1/6881; C12Q 1/68; C12Q 1/6883; C12Q 1/70
See application file for complete search history.

(56) References Cited

U.S. PATENT DOCUMENTS

| 5,189,147 A | 2/1993 | Saito et al. |
|---|---|---|
| 5,213,960 A | 5/1993 | Chang |
| 5,296,351 A | 3/1994 | Morley |
| 5,298,396 A | 3/1994 | Kotzin et al. |
| 5,326,696 A | 7/1994 | Chang |
| 5,336,598 A | 8/1994 | Kotzin et al. |
| 5,418,134 A | 5/1995 | Morley |
| 5,506,126 A | 4/1996 | Seed et al. |
| 5,627,037 A | 5/1997 | Ward |
| 5,627,052 A | 5/1997 | Schrader |
| 5,635,354 A | 6/1997 | Kourilsky et al. |
| 5,635,400 A | 6/1997 | Brenner |
| 5,667,967 A | 9/1997 | Steinman et al. |
| 5,741,676 A | 4/1998 | Fuller |
| 5,776,708 A | 7/1998 | Kotzin et al. |
| 5,776,737 A | 7/1998 | Dunn |
| 5,837,447 A | 11/1998 | Gorski |
| 5,846,719 A | 12/1998 | Brenner et al. |
| 5,925,517 A | 7/1999 | Tyagi et al. |
| 5,935,793 A | 8/1999 | Wong |
| 5,981,176 A | 11/1999 | Wallace |
| 6,087,096 A | 7/2000 | Dau et al. |
| 6,091,000 A | 7/2000 | Haynes |

(Continued)

FOREIGN PATENT DOCUMENTS

| CN | 101225441 A | 7/2008 |
|---|---|---|
| CN | 102272327 A | 12/2011 |

(Continued)

OTHER PUBLICATIONS

Andreas Lossius et al; "High-throughput sequencing of TCR repertoires in multiple sclerosis reveals intrathecal enrichment of EBV-reactive CD8 + T cells: Clinical immunology", European Journal of Immunology, vol. 44, No. 11, (Sep. 16, 2014), pp. 3439-3452.

Bidwell et al; "Advances in DNA-based HLA-typing methods", Immunology Today, Elsevier Publications, Camridge, GB, vol. 15, No. 7, (Jul. 1, 1994), pp. 303-307.

Meriem Attaf et al; "Alpha beta T cell receptors as predictors of health and disease", Cellular & Molecular Immunology, vol. 12, No. 4, (Jan. 26, 2015), pp. 391-399.

Spellman S. et al; "Advances in the Selection of HLA-Compatible Donors; Refinements in HLA Typing and Matching over the First 20 Years of the National Marrow Donor Program Registry", Biology of Blood and Marrow Transplantation, Kluge Carden Jennings Publishing, Charlottesville, VA, US, vol. 14, No. 9, (Sep. 1, 208), pp. 37-44.

(Continued)

*Primary Examiner* — Jerry Lin
(74) *Attorney, Agent, or Firm* — Brian E. Davy; Edward J. Baba; Bozicevic, Field & Francis LLP

(57) ABSTRACT

Methods are provided for predicting a subject's infection status using high-throughput T cell receptor sequencing to match the subject's TCR repertoire to a known set of disease-associated T cell receptor sequences. The methods of the present invention may be used to predict the status of several infectious agents in a single sample from a subject. Methods are also provided for predicting a subject's HLA status using high-throughput immune receptor sequencing.

11 Claims, 19 Drawing Sheets

Specification includes a Sequence Listing.

(56) References Cited

U.S. PATENT DOCUMENTS

| | | |
|---|---|---|
| 6,172,214 B1 | 1/2001 | Brenner |
| 6,228,589 B1 | 5/2001 | Brenner |
| 6,258,568 B1 | 7/2001 | Nyren |
| 6,291,183 B1 | 9/2001 | Pirrung et al. |
| 6,300,070 B1 | 10/2001 | Boles et al. |
| 6,312,690 B1 | 11/2001 | Edelman et al. |
| 6,416,948 B1 | 7/2002 | Pilarski et al. |
| 6,440,706 B1 | 8/2002 | Vogelstein et al. |
| 6,458,530 B1 | 10/2002 | Morris et al. |
| 6,489,103 B1 | 12/2002 | Griffiths et al. |
| 6,524,829 B1 | 2/2003 | Seegar |
| 6,569,627 B2 | 5/2003 | Wittwer et al. |
| 6,596,492 B2 | 7/2003 | Avery et al. |
| 6,753,147 B2 | 6/2004 | Vogelstein et al. |
| 6,787,308 B2 | 9/2004 | Balasubramanian et al. |
| 6,919,434 B1 | 7/2005 | Goto et al. |
| 6,964,850 B2 | 11/2005 | Bevilacqua |
| 7,068,874 B2 | 6/2006 | Wang et al. |
| 7,112,423 B2 | 9/2006 | Van Ness et al. |
| 7,115,400 B1 | 10/2006 | Adessi et al. |
| 7,148,040 B2 | 12/2006 | Meagher et al. |
| 7,157,228 B2 | 1/2007 | Hashmi et al. |
| 7,157,274 B2 | 1/2007 | Bohm et al. |
| 7,208,795 B2 | 4/2007 | Carver et al. |
| 7,232,653 B1 | 6/2007 | Austrup et al. |
| 7,306,906 B2 | 12/2007 | Maruyama et al. |
| 7,313,308 B2 | 12/2007 | Turner et al. |
| 7,323,305 B2 | 1/2008 | Leamon et al. |
| 7,323,306 B2 | 1/2008 | Dunn et al. |
| 7,329,731 B2 | 2/2008 | Jakobsen et al. |
| 7,351,578 B2 | 4/2008 | Cheo et al. |
| 7,365,179 B2 | 4/2008 | Brenner |
| 7,371,519 B2 | 5/2008 | Wolber |
| 7,375,211 B2 | 5/2008 | Kou |
| 7,393,665 B2 | 7/2008 | Brenner |
| 7,432,084 B2 | 10/2008 | Shoemaker |
| 7,537,897 B2 | 5/2009 | Brenner et al. |
| 7,544,473 B2 | 6/2009 | Brenner |
| 7,572,582 B2 | 8/2009 | Wengel et al. |
| 7,662,557 B2 | 2/2010 | McCafferty et al. |
| 7,666,604 B2 | 2/2010 | Jakobsen et al. |
| 7,691,994 B2 | 4/2010 | Brewer et al. |
| 7,700,323 B2 | 4/2010 | Willis et al. |
| 7,709,197 B2 | 5/2010 | Drmanac |
| 7,741,463 B2 | 6/2010 | Gormley et al. |
| 7,749,697 B2 | 7/2010 | Oleksiewicz et al. |
| 7,785,783 B2 | 8/2010 | Morley et al. |
| 7,833,716 B2 | 11/2010 | Becker et al. |
| 7,842,457 B2 | 11/2010 | Berka et al. |
| 7,862,999 B2 | 1/2011 | Zheng et al. |
| 7,879,324 B2 | 2/2011 | Saxon |
| 7,892,550 B2 | 2/2011 | Dennis et al. |
| 7,907,800 B2 | 3/2011 | Foquet et al. |
| 7,915,015 B2 | 3/2011 | Vogelstein et al. |
| 7,955,794 B2 | 6/2011 | Shen et al. |
| 7,956,043 B2 | 6/2011 | Krieg et al. |
| 7,960,116 B2 | 6/2011 | Eid et al. |
| 8,012,690 B2 | 9/2011 | Berka et al. |
| 8,021,842 B2 | 9/2011 | Brenner |
| 8,030,023 B2 | 10/2011 | Adams et al. |
| 8,048,627 B2 | 11/2011 | Dressman et al. |
| 8,053,188 B2 | 11/2011 | Gullberg et al. |
| 8,053,235 B2 | 11/2011 | Buckner et al. |
| 8,137,569 B2 | 3/2012 | Harnack et al. |
| 8,137,936 B2 | 3/2012 | Macevicz |
| 8,153,375 B2 | 4/2012 | Travers et al. |
| 8,158,359 B2 | 4/2012 | Leamon et al. |
| 8,236,503 B2 | 8/2012 | Faham et al. |
| 8,283,294 B2 | 10/2012 | Kastrup et al. |
| 8,309,312 B2 | 11/2012 | Lang et al. |
| 8,313,625 B2 | 11/2012 | Rothberg et al. |
| 8,318,433 B2 | 11/2012 | Brenner |
| 8,394,590 B2 | 3/2013 | Kwong et al. |
| 8,445,205 B2 | 5/2013 | Brenner |
| 8,481,292 B2 | 7/2013 | Casbon et al. |
| 8,507,205 B2 | 8/2013 | Faham |
| 8,628,927 B2 | 1/2014 | Faham |
| 8,685,678 B2 | 4/2014 | Casbon |
| 8,685,898 B2 | 4/2014 | Wiley |
| 8,691,510 B2 | 4/2014 | Faham |
| 8,699,361 B2 | 4/2014 | Jim et al. |
| 8,715,967 B2 | 5/2014 | Casbon |
| 8,722,368 B2 | 5/2014 | Casbon |
| 8,728,766 B2 | 5/2014 | Casbon |
| 8,741,606 B2 | 6/2014 | Casbon |
| 8,748,103 B2 | 6/2014 | Faham |
| 8,759,036 B2 | 6/2014 | Wang |
| 8,795,970 B2 | 8/2014 | Faham |
| 8,826,321 B2 | 9/2014 | Cronin et al. |
| 8,835,358 B2 | 9/2014 | Fodor |
| 9,012,148 B2 | 4/2015 | Han et al. |
| 9,043,160 B1 | 5/2015 | Moorhead et al. |
| 9,150,905 B2 | 10/2015 | Robins et al. |
| 9,217,176 B2 | 12/2015 | Faham et al. |
| 9,228,232 B2 | 1/2016 | Faham et al. |
| 9,371,558 B2 | 6/2016 | Robins et al. |
| 9,394,567 B2 | 7/2016 | Asbury et al. |
| 9,416,420 B2 | 8/2016 | Faham et al. |
| 9,506,119 B2 | 11/2016 | Faham et al. |
| 9,512,487 B2 | 12/2016 | Faham et al. |
| 9,708,657 B2 | 7/2017 | Asbury et al. |
| 9,809,813 B2 | 11/2017 | Robins et al. |
| 10,066,265 B2 | 9/2018 | Klinger et al. |
| 10,077,473 B2 | 9/2018 | Asbury et al. |
| 10,077,478 B2 | 9/2018 | Faham et al. |
| 2002/0076725 A1 | 6/2002 | Toyosaki-Maeda et al. |
| 2002/0110807 A1 | 8/2002 | Pilarski et al. |
| 2003/0096277 A1 | 5/2003 | Chen |
| 2003/0120061 A1 | 6/2003 | Zhang |
| 2003/0162197 A1 | 8/2003 | Morley et al. |
| 2003/0207300 A1 | 11/2003 | Matray et al. |
| 2004/0018489 A1 | 1/2004 | Ma et al. |
| 2004/0033490 A1 | 2/2004 | Laird et al. |
| 2004/0121364 A1 | 6/2004 | Chee et al. |
| 2004/0132050 A1 | 7/2004 | Monforte |
| 2004/0146901 A1 | 7/2004 | Morris et al. |
| 2004/0170977 A1 | 9/2004 | Laird |
| 2004/0235061 A1 | 11/2004 | Wilkie et al. |
| 2004/0248172 A1 | 12/2004 | Samoszuk et al. |
| 2005/0037356 A1 | 2/2005 | Gullberg et al. |
| 2005/0064421 A1 | 3/2005 | Gehrmann et al. |
| 2005/0142577 A1 | 6/2005 | Jones et al. |
| 2005/0250147 A1 | 11/2005 | MacEvicz |
| 2005/0255482 A1 | 11/2005 | Morley et al. |
| 2005/0260570 A1 | 11/2005 | Mao et al. |
| 2006/0019304 A1 | 1/2006 | Hardenbol et al. |
| 2006/0020397 A1 | 1/2006 | Kermani |
| 2006/0046258 A1 | 3/2006 | Lapidus et al. |
| 2006/0085139 A1 | 4/2006 | Collette et al. |
| 2006/0088876 A1 | 4/2006 | Bauer |
| 2006/0134125 A1 | 6/2006 | Luxembourg et al. |
| 2006/0147925 A1 | 7/2006 | Morley et al. |
| 2006/0199210 A1 | 9/2006 | Weichselbaum et al. |
| 2006/0211030 A1 | 9/2006 | Brenner |
| 2006/0216737 A1 | 9/2006 | Bodeau |
| 2006/0228350 A1 | 10/2006 | Wu et al. |
| 2006/0233812 A1 | 10/2006 | Burnie et al. |
| 2006/0234234 A1 | 10/2006 | Van Dongen et al. |
| 2006/0259248 A1 | 11/2006 | Collette et al. |
| 2006/0263789 A1 | 11/2006 | Kincaid |
| 2007/0020640 A1 | 1/2007 | McCloskey et al. |
| 2007/0020670 A1 | 1/2007 | Loken et al. |
| 2007/0105105 A1 | 5/2007 | Clelland et al. |
| 2007/0117134 A1 | 5/2007 | Kou |
| 2007/0160994 A1 | 7/2007 | Lim et al. |
| 2007/0161001 A1 | 7/2007 | Leshkowitz |
| 2007/0172873 A1 | 7/2007 | Brenner et al. |
| 2007/0238099 A1 | 10/2007 | Cohen et al. |
| 2007/0243564 A1 | 10/2007 | Lawson et al. |
| 2007/0264653 A1 | 11/2007 | Berlin et al. |
| 2007/0286849 A1 | 12/2007 | Chaturvedi |
| 2008/0050780 A1 | 2/2008 | Lee et al. |
| 2008/0069770 A1 | 3/2008 | Hercend et al. |
| 2008/0108509 A1 | 5/2008 | Haupl et al. |

(56) References Cited

U.S. PATENT DOCUMENTS

| | | |
|---|---|---|
| 2008/0166704 A1 | 7/2008 | Marche et al. |
| 2008/0166718 A1 | 7/2008 | Lim et al. |
| 2008/0199916 A1 | 8/2008 | Zheng et al. |
| 2008/0248484 A1 | 10/2008 | Bauer |
| 2008/0274904 A1 | 11/2008 | Gormley et al. |
| 2008/0280774 A1 | 11/2008 | Burczynski et al. |
| 2008/0286777 A1 | 11/2008 | Candeias et al. |
| 2009/0026082 A1 | 1/2009 | Rothberg et al. |
| 2009/0053184 A1 | 2/2009 | Morgan et al. |
| 2009/0098555 A1 | 4/2009 | Roth et al. |
| 2009/0105959 A1 | 4/2009 | Braverman et al. |
| 2009/0181859 A1 | 7/2009 | Muraguchi |
| 2009/0197257 A1 | 8/2009 | Harris |
| 2009/0208955 A1 | 8/2009 | Robins et al. |
| 2009/0226975 A1 | 9/2009 | Sabot et al. |
| 2009/0233301 A1 | 9/2009 | Lee |
| 2009/0233802 A1 | 9/2009 | Bignell et al. |
| 2009/0253581 A1 | 10/2009 | Van Eijk et al. |
| 2009/0264299 A1 | 10/2009 | Drmanac et al. |
| 2009/0280489 A1 | 11/2009 | Devinder et al. |
| 2009/0286237 A1 | 11/2009 | Fitzgerald et al. |
| 2009/0298060 A1 | 12/2009 | Lal et al. |
| 2010/0008920 A1 | 1/2010 | Schneck et al. |
| 2010/0021894 A1 | 1/2010 | Mirkin et al. |
| 2010/0021896 A1 | 1/2010 | Han |
| 2010/0021984 A1 | 1/2010 | Edd |
| 2010/0027896 A1 | 2/2010 | Geva et al. |
| 2010/0034834 A1 | 2/2010 | Robbins et al. |
| 2010/0035764 A1 | 2/2010 | Chen |
| 2010/0040606 A1 | 2/2010 | Lantto et al. |
| 2010/0042329 A1 | 2/2010 | Hood et al. |
| 2010/0105886 A1 | 4/2010 | Wondenberg |
| 2010/0129874 A1 | 5/2010 | Mitra et al. |
| 2010/0137143 A1 | 6/2010 | Rothberg et al. |
| 2010/0151471 A1 | 6/2010 | Faham et al. |
| 2010/0159456 A1 | 6/2010 | Albitar |
| 2010/0167353 A1 | 7/2010 | Walder et al. |
| 2010/0173394 A1 | 7/2010 | Colston, Jr. |
| 2010/0255471 A1 | 10/2010 | Clarke |
| 2010/0261204 A1 | 10/2010 | Goolsby et al. |
| 2010/0267043 A1 | 10/2010 | Braverman |
| 2010/0285975 A1 | 11/2010 | Mathies |
| 2010/0300895 A1 | 12/2010 | Nobile et al. |
| 2010/0304982 A1 | 12/2010 | Hinz et al. |
| 2010/0323348 A1 | 12/2010 | Hamady et al. |
| 2010/0323355 A1 | 12/2010 | Dittmer |
| 2010/0330571 A1 | 12/2010 | Robins et al. |
| 2011/0003291 A1 | 1/2011 | Pasqual et al. |
| 2011/0014659 A1 | 1/2011 | Balazs et al. |
| 2011/0097712 A1 | 4/2011 | Cantor et al. |
| 2011/0104671 A1 | 5/2011 | Dornan et al. |
| 2011/0105343 A1 | 5/2011 | Puledran et al. |
| 2011/0129830 A1 | 6/2011 | Ladner et al. |
| 2011/0160078 A1 | 6/2011 | Fodor et al. |
| 2011/0166034 A1 | 7/2011 | Kwong et al. |
| 2011/0183863 A1 | 7/2011 | Wagner et al. |
| 2011/0195253 A1 | 8/2011 | Hinz et al. |
| 2011/0207134 A1 | 8/2011 | Faham et al. |
| 2011/0207135 A1 | 8/2011 | Faham et al. |
| 2011/0207617 A1 | 8/2011 | Faham et al. |
| 2011/0251099 A1 | 10/2011 | Visvanathan et al. |
| 2012/0010096 A1 | 1/2012 | Wohlgemuth et al. |
| 2012/0035062 A1 | 2/2012 | Schultz et al. |
| 2012/0058902 A1 | 3/2012 | Livingston et al. |
| 2012/0071331 A1 | 3/2012 | Casbon et al. |
| 2012/0073667 A1 | 3/2012 | Schultz et al. |
| 2012/0122714 A1 | 5/2012 | Samuels |
| 2012/0135409 A1 | 5/2012 | Faham |
| 2012/0143531 A1 | 6/2012 | Davey et al. |
| 2012/0172241 A1 | 7/2012 | Rearick et al. |
| 2012/0173158 A1 | 7/2012 | Hubbell |
| 2012/0220466 A1 | 8/2012 | Fire et al. |
| 2012/0308999 A1 | 12/2012 | Sarma et al. |
| 2013/0005584 A1 | 1/2013 | Faham |
| 2013/0017957 A1 | 1/2013 | Faham et al. |
| 2013/0045221 A1 | 2/2013 | Stauss et al. |
| 2013/0065768 A1 | 3/2013 | Zheng |
| 2013/0116130 A1 | 5/2013 | Fu |
| 2013/0123120 A1 | 5/2013 | Zimmermann et al. |
| 2013/0136799 A1 | 5/2013 | Faham |
| 2013/0137108 A1 | 5/2013 | Tripathi et al. |
| 2013/0150252 A1 | 6/2013 | Faham |
| 2013/0196328 A1 | 8/2013 | Pepin |
| 2013/0196861 A1 | 8/2013 | Quake |
| 2013/0202718 A1 | 8/2013 | Pepin |
| 2013/0236895 A1 | 9/2013 | Faham |
| 2013/0253842 A1 | 9/2013 | Sherwood et al. |
| 2013/0267427 A1 | 10/2013 | Faham |
| 2013/0273647 A1 | 10/2013 | Sahin et al. |
| 2013/0288237 A1 | 10/2013 | Robins et al. |
| 2013/0302801 A1 | 11/2013 | Asbury |
| 2013/0324422 A1 | 12/2013 | Faham et al. |
| 2013/0344066 A1 | 12/2013 | Faham |
| 2014/0057799 A1 | 2/2014 | Johnson et al. |
| 2014/0065629 A1 | 3/2014 | Barken et al. |
| 2014/0094376 A1 | 4/2014 | Han |
| 2014/0127699 A1 | 5/2014 | Han |
| 2014/0141982 A1 | 5/2014 | Jacobson et al. |
| 2014/0155277 A1 | 6/2014 | Wiley |
| 2014/0186848 A1 | 7/2014 | Robins et al. |
| 2014/0194295 A1 | 7/2014 | Robins et al. |
| 2014/0206548 A1 | 7/2014 | Robins et al. |
| 2014/0206549 A1 | 7/2014 | Robins et al. |
| 2014/0213463 A1 | 7/2014 | Robins et al. |
| 2014/0221220 A1 | 8/2014 | Robins et al. |
| 2014/0227705 A1 | 8/2014 | Vogelstein et al. |
| 2014/0234835 A1 | 8/2014 | Pepin |
| 2014/0235454 A1 | 8/2014 | Faham |
| 2014/0255929 A1 | 9/2014 | Zheng |
| 2014/0255944 A1 | 9/2014 | Carlton |
| 2014/0256567 A1 | 9/2014 | Robins et al. |
| 2014/0256592 A1 | 9/2014 | Faham |
| 2014/0315725 A1 | 10/2014 | Faham et al. |
| 2014/0322716 A1 | 10/2014 | Robins et al. |
| 2014/0336059 A1 | 11/2014 | Faham et al. |
| 2014/0342360 A1 | 11/2014 | Faham et al. |
| 2014/0342367 A1 | 11/2014 | Faham et al. |
| 2014/0349883 A1 | 11/2014 | Faham et al. |
| 2014/0356339 A1 | 12/2014 | Faham et al. |
| 2015/0017630 A1 | 1/2015 | Oved et al. |
| 2015/0017652 A1 | 1/2015 | Robins et al. |
| 2015/0031043 A1 | 1/2015 | Faham et al. |
| 2015/0031553 A1 | 1/2015 | Faham et al. |
| 2015/0031555 A1 | 1/2015 | Johnson et al. |
| 2015/0038346 A1 | 2/2015 | Faham et al. |
| 2015/0051089 A1 | 2/2015 | Robins et al. |
| 2015/0065352 A1 | 3/2015 | Faham et al. |
| 2015/0087535 A1 | 3/2015 | Patel et al. |
| 2015/0133317 A1 | 5/2015 | Robinson et al. |
| 2015/0154352 A1 | 6/2015 | Johnson et al. |
| 2015/0167080 A1 | 6/2015 | Moorhead et al. |
| 2015/0203897 A1 | 7/2015 | Robins et al. |
| 2015/0215062 A1 | 7/2015 | Lee |
| 2015/0218656 A1 | 8/2015 | Kirsch et al. |
| 2015/0232936 A1 | 8/2015 | Shoemaker et al. |
| 2015/0247182 A1 | 9/2015 | Faham et al. |
| 2015/0247198 A1 | 9/2015 | Klinger et al. |
| 2015/0247201 A1 | 9/2015 | Faham et al. |
| 2015/0252419 A1 | 9/2015 | Moorhead et al. |
| 2015/0252422 A1 | 9/2015 | Faham et al. |
| 2015/0259734 A1 | 9/2015 | Asbury et al. |
| 2015/0275296 A1 | 10/2015 | Klinger et al. |
| 2015/0275308 A1 | 10/2015 | Carlton et al. |
| 2015/0299785 A1 | 10/2015 | Livingston et al. |
| 2015/0299786 A1 | 10/2015 | Robins et al. |
| 2015/0299800 A1 | 10/2015 | Faham et al. |
| 2016/0024493 A1 | 1/2016 | Robins et al. |
| 2016/0115532 A1 | 4/2016 | Faham |
| 2016/0138011 A1 | 5/2016 | Dewitt et al. |
| 2016/0186260 A1 | 6/2016 | Klinger et al. |
| 2016/0201133 A1 | 7/2016 | Faham et al. |
| 2016/0251721 A1 | 9/2016 | Robins et al. |
| 2016/0251728 A1 | 9/2016 | Faham et al. |
| 2016/0258025 A1 | 9/2016 | Klinger et al. |

(56) References Cited

U.S. PATENT DOCUMENTS

| | | |
|---|---|---|
| 2016/0304956 A1 | 10/2016 | Robins et al. |
| 2016/0319340 A1 | 11/2016 | Robins et al. |
| 2017/0037469 A1 | 2/2017 | Robins et al. |
| 2017/0292149 A1 | 10/2017 | Emerson et al. |
| 2017/0335386 A1 | 11/2017 | Livingston et al. |
| 2017/0335390 A1 | 11/2017 | Asbury et al. |
| 2017/0335391 A1 | 11/2017 | Emerson et al. |
| 2017/0349954 A1 | 12/2017 | Faham et al. |
| 2018/0073015 A1 | 3/2018 | Robins et al. |
| 2018/0080090 A1 | 3/2018 | Faham et al. |
| 2018/0087109 A1 | 3/2018 | Klinger et al. |
| 2018/0112278 A1 | 4/2018 | Faham et al. |
| 2018/0312832 A1 | 11/2018 | Robins et al. |

FOREIGN PATENT DOCUMENTS

| | | |
|---|---|---|
| CN | 103097888 A | 5/2013 |
| EA | 007958 B1 | 2/2007 |
| EP | 0303459 A2 | 2/1989 |
| EP | 0799897 A1 | 10/1997 |
| EP | 1516929 A2 | 3/2005 |
| EP | 1544308 A1 | 6/2005 |
| EP | 1549764 B1 | 7/2005 |
| EP | 0972081 B1 | 6/2007 |
| EP | 1544308 B1 | 1/2009 |
| EP | 2062982 A1 | 5/2009 |
| EP | 2088432 A1 | 8/2009 |
| EP | 2418287 A2 | 2/2012 |
| EP | 2364368 B1 | 1/2014 |
| JP | 4262799 A | 9/1992 |
| JP | 2002-503954 A | 2/2001 |
| JP | 2005-245381 A | 9/2005 |
| JP | 2006-501842 A | 1/2006 |
| JP | 2007-515955 A | 6/2007 |
| JP | 2007-536939 A | 12/2007 |
| JP | 2008-099588 A | 5/2008 |
| JP | 2011-505123 A | 2/2011 |
| JP | 2012-508011 A | 4/2012 |
| JP | 2013-524848 A | 6/2013 |
| JP | 2013-524849 A | 6/2013 |
| WO | WO 1993/001838 A1 | 2/1993 |
| WO | WO 1995/028481 A1 | 10/1995 |
| WO | WO 1997/013868 A1 | 4/1997 |
| WO | WO 1997/013877 A1 | 4/1997 |
| WO | WO 1997/018330 A1 | 5/1997 |
| WO | WO 1997/046706 A1 | 12/1997 |
| WO | WO 1998/001738 A2 | 1/1998 |
| WO | WO 1998/044151 A1 | 10/1998 |
| WO | WO 1999/019717 A1 | 4/1999 |
| WO | WO 1999/020798 A1 | 4/1999 |
| WO | WO 2001/014424 A2 | 3/2001 |
| WO | WO 2002/024322 A2 | 3/2002 |
| WO | WO 2003/008624 A2 | 1/2003 |
| WO | WO 2003/044225 A2 | 5/2003 |
| WO | WO 2003/052101 A1 | 6/2003 |
| WO | WO 2003/059155 A2 | 7/2003 |
| WO | WO 2004/003820 A2 | 1/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/096985 A2 | 11/2004 |
| WO | WO 2005/003375 A2 | 1/2005 |
| WO | WO 2005/005651 A2 | 1/2005 |
| WO | WO 2005/010200 A2 | 2/2005 |
| WO | WO 2005/042774 A2 | 5/2005 |
| WO | WO 2005/053603 A2 | 6/2005 |
| WO | WO 2005/056828 A1 | 6/2005 |
| WO | WO 2005/059176 A1 | 6/2005 |
| WO | WO 2005/084134 A2 | 9/2005 |
| WO | WO 2005/111242 A2 | 11/2005 |
| WO | WO 2005/113803 A1 | 12/2005 |
| WO | WO 2006/076025 A2 | 7/2006 |
| WO | WO 2006/076205 A2 | 7/2006 |
| WO | WO 2006/110855 A2 | 10/2006 |
| WO | WO 2006/116155 A2 | 11/2006 |
| WO | WO 2006/138284 A2 | 12/2006 |
| WO | WO 2007/008759 A2 | 1/2007 |
| WO | WO 2007/134220 A2 | 11/2007 |
| WO | WO 2008/026927 A2 | 3/2008 |
| WO | WO 2008/039694 A2 | 4/2008 |
| WO | WO 2008/108803 A2 | 9/2008 |
| WO | WO 2008/147879 A1 | 12/2008 |
| WO | WO 2009/015296 A1 | 1/2009 |
| WO | WO 2009/017678 A2 | 2/2009 |
| WO | WO 2009/019657 A2 | 2/2009 |
| WO | WO 2009/021215 A1 | 2/2009 |
| WO | WO 2009/045898 A2 | 4/2009 |
| WO | WO 2009/070767 A2 | 6/2009 |
| WO | WO 2009/095567 A2 | 8/2009 |
| WO | WO 2009/108860 A2 | 9/2009 |
| WO | WO 2009/108866 A2 | 9/2009 |
| WO | WO 2009/137255 A2 | 11/2009 |
| WO | WO 2009/137832 A2 | 11/2009 |
| WO | WO 2009/145925 A1 | 12/2009 |
| WO | WO 2009/151628 A2 | 12/2009 |
| WO | WO 2009/152928 A2 | 12/2009 |
| WO | WO 2009/158521 A2 | 12/2009 |
| WO | WO 2010/011894 A1 | 1/2010 |
| WO | WO 2010/036352 A1 | 4/2010 |
| WO | WO 2010/053587 A2 | 5/2010 |
| WO | WO 2010/083456 A1 | 7/2010 |
| WO | WO 2010/151416 A1 | 12/2010 |
| WO | WO 2011/017151 A2 | 2/2011 |
| WO | WO 2011/083296 A1 | 7/2011 |
| WO | WO 2011/083996 A2 | 7/2011 |
| WO | WO 2011/106738 A2 | 9/2011 |
| WO | WO 2011/107595 A2 | 9/2011 |
| WO | WO 2011/139371 A1 | 11/2011 |
| WO | WO 2011/139372 A1 | 11/2011 |
| WO | WO 2011/140433 A2 | 11/2011 |
| WO | WO 2012/012703 A2 | 1/2012 |
| WO | WO 2012/017081 A1 | 2/2012 |
| WO | WO 2012/027503 A2 | 3/2012 |
| WO | WO 2012/048340 A2 | 4/2012 |
| WO | WO 2012/048341 A1 | 4/2012 |
| WO | WO 2012/055929 A1 | 5/2012 |
| WO | WO 2012/061832 A1 | 5/2012 |
| WO | WO 2012/083069 A2 | 6/2012 |
| WO | WO 2012/083225 A2 | 6/2012 |
| WO | WO 2012/122484 A1 | 9/2012 |
| WO | WO 2012/142213 A2 | 10/2012 |
| WO | WO 2012/148497 A2 | 11/2012 |
| WO | WO 2012/159754 A2 | 11/2012 |
| WO | WO 2013/033721 A1 | 3/2013 |
| WO | WO 2013/036459 A2 | 3/2013 |
| WO | WO 2013/055595 A1 | 4/2013 |
| WO | WO 2013/059725 A1 | 4/2013 |
| WO | WO 2013/066726 A1 | 5/2013 |
| WO | WO 2013/085855 A1 | 6/2013 |
| WO | WO 2013/086450 A1 | 6/2013 |
| WO | WO 2013/086462 A1 | 6/2013 |
| WO | WO 2013/090390 A2 | 6/2013 |
| WO | WO 2013/090469 A1 | 6/2013 |
| WO | WO 2013/096480 A2 | 6/2013 |
| WO | WO 2013/123442 A1 | 8/2013 |
| WO | WO 2013/130512 A2 | 9/2013 |
| WO | WO 2013/131074 A1 | 9/2013 |
| WO | WO 2013/134162 A2 | 9/2013 |
| WO | WO 2013/134302 A1 | 9/2013 |
| WO | WO 2013/155119 A1 | 10/2013 |
| WO | WO 2013/158936 A1 | 10/2013 |
| WO | WO 2013/169957 A1 | 11/2013 |
| WO | WO 2013/181428 A2 | 12/2013 |
| WO | WO 2013/188471 A2 | 12/2013 |
| WO | WO 2013/188831 A1 | 12/2013 |
| WO | WO 2014/018460 A1 | 1/2014 |
| WO | WO 2014/026031 A1 | 2/2014 |
| WO | WO 2014/062945 A1 | 4/2014 |
| WO | WO 2014/062959 A1 | 4/2014 |
| WO | WO 2014/066184 A1 | 5/2014 |
| WO | WO 2014/130685 A1 | 8/2014 |
| WO | WO 2014/145992 A1 | 9/2014 |

(56) References Cited

FOREIGN PATENT DOCUMENTS

| | | |
|---|---|---|
| WO | WO 2015/002908 A1 | 1/2015 |
| WO | WO 2015/013461 A2 | 1/2015 |
| WO | WO 2015/058159 A1 | 4/2015 |
| WO | WO 2015/106161 A1 | 7/2015 |
| WO | WO 2015/134787 A2 | 9/2015 |
| WO | WO 2015/153788 A1 | 10/2015 |
| WO | WO 2015/160439 A2 | 10/2015 |
| WO | WO 2016/069886 A1 | 5/2016 |
| WO | WO 2016/138122 A1 | 9/2016 |
| WO | WO 2016/161273 A1 | 10/2016 |

OTHER PUBLICATIONS

Attaf, et al., "αβ T cell receptors as predictors of health and disease." Cellular & Molecular Immunology (Jul. 2015); 12 (4): 391-399. Epub Jan. 26, 2015.

Bidwell, "Advances in DNA-based HLA-typing methods." Immunol Today (Jul. 1994); 15 (7): 303-307.

DeWitt, et al., "Dynamics of the Cytotoxic T Cell Response to a Model of Acute Viral Infection." J. Virol. (Apr. 2015); 89 (8): 4517-4526. Epub Feb. 4, 2015.

Dziubianau, M., et al., "TCR repertoire analysis by next generation sequencing allows complex differential diagnosis of T cell-related pathology." Am J Transplant (2013); 13(11): 2842-2854. doi: 10.1111/ajt.12431. Epub Sep. 10, 2013.

Emerson, et al., "De novo detection and HLA-association of public T cell responses to Cytomegalovirus using high-throughput immune repertoire sequencing (VIR1P.1134)." The Journal of Immunology (May 2015); 194 (1 Supplement): 74.1, Abstract.

Emerson, et al., "Immunosequencing identifies signatures of cytomegalovirus exposure history and HLA-mediated effects on the T cell repertoire." Nature Genetics (May 2017); 49 (3): 659-665. Epub Apr. 3, 2017.

European Patent Application No. 15854358.7, Extended European Search Report dated Mar. 12, 2018, 12 pages.

European Patent Application No. 18153536.0, Extended European Search Report dated Jun. 6, 2018, 7 pages.

European Patent Application No. 16756268.5, Extended European Search Report dated Oct. 22, 2018, 20 pages.

European Patent Application No. 16756268.5, Partial Supplementary European Search Report dated Jun. 19, 2018, 21 pages.

European Patent Application No. 16774304.6, Extended European Search Report dated Oct. 15, 2018, 9 pages.

European Patent Application No. 18184843.3, Extended European Search Report dated Aug. 13, 2018, 10 pages.

Födinger et al., "Multiplex PCR for rapid detection of T-cell receptor-gamma chain gene rearrangements in patients with lymphoproliferative diseases." British Journal of Haematology (1996); 94(1): 136-139.

Han, et al., "Linking T-cell receptor sequence to functional phenotype at the single-cell level." Nat Biotechnol. (2014); 32 (7): 684-692. Epub Jun. 22, 2014.

Howie, et al., "High throughput pairing of T cell receptor α and β sequences." Science Translational Medicine (2015); 7(301): 301ra131, and supplementary materials, 19 pages.

Linnemann, et al., "High-throughput identification of antigen-specific TCRs by TCR gene capture." Nature Medicine (Nov. 2013); 19 (11): 1534-1541. Epub Oct. 13, 2013.

Linnemann, et al., "TCR repertoires of intratumoral T-cell subsets." Immunological Reviews (2014); 257(1): 72-82.

Lossius, et al., "High-throughput sequencing of TCR repertoires in multiple sclerosis reveals intrathecal enrichment of EBV-reactive CD8+ T cells." European Journal of Immunology (Nov. 2014); 44 (11): 3439-3452. Epub Sep. 16, 2014.

Lowe, T., et al., "A computer program for selection of oligonucleotide primers for polymerase chain reactions," Nucleic Acids Research (1990); 18(7):1757-1761.

Panzara, et al., "Analysis of the T cell repertoire using the PCR and specific oligonucleotide primers." Biotechniques (1992); 12(5): 728-735.

Qu, et al., "Efficient frequency-based de novo short-read clustering for error trimming in next-generation sequencing", Genome Research, 19: 1309-1315 (2009).

Seder and Ahmed, "Similarities and differences in CD4+ and CD8+ effector and memory T cell generation." Nat Immunol. (2003); 4 (9): 835-842.

Sotomayor, et al., "Conversion of tumor-specific CD4$^+$ T-cell tolerance to T-cell priming through in vivo ligation of CD40." Nature Medicine (1999); 5(7): 780-787.

Spellman, et al., "Advances in the selection of HLA-compatible donors: refinements in HLA typing and matching over the first 20 years of the National Marrow Donor Program Registry." Biol Blood Marrow Transplant (2008); (9 Suppl):37-44. Epub Jun. 20, 2008.

Szczepek, et al., "A high frequency of circulating B cells share clonotypic lg heavy-chain VDJ rearrangements with autologous bone marrow plasma cells in multiple myeloma, as measured by single-cell and in situ reverse transcriptase-polymerase chain reaction." Blood (1998); 92(8): 2844-2855.

Willenbrock, et al., "Analysis of T-Cell Subpopulations in T-Cell Non-Hodgkin's Lymphoma of Angioimmunoblastic Lymphadenopathy with Dysproteinemia Type by Single Target Gene Amplification of T Cell Receptor-β Gene Rearrangements." Am J Pathol. (2001); 158(5): 1851-1857.

Yagi, et al., "Detection of clonotypic IGH and TCR rearrangements in the neonatal blood spots of infants and children with B-cell precursor acute lymphoblastic leukemia." Blood (2000); 96(1): 264-268.

US 8,642,750, 02/2014, Faham et al. (withdrawn).

Abbott, et al. "Design and use of signature primers to detect carry-over of amplified material", *J Virol Methods*, 46(1):51-59, Abstract Only (1994).

Ahmadzadeh et al. "FOXP3 expression accurately defines the population of intratumoral regulatory T cells that selectively accumulate in metastatic melanoma lesions", *Blood*, 112(13): 4953-4960 (2008).

Akatsuka, Y. et al. "Rapid screening of T-cell receptor (TCR) variable gene usage by multiplex PCR: Application for assessment of clonal composition", *Tissue Antigens*, 53(2):122-134 (1999).

Alatrakchi et al. "T-cell clonal expansion in patients with B-cell lymphoproliferative disorders", *Journal of Immunotherapy*, 21(5):363-370 (1998).

Alexandre, D. et al. "*H. sapiens* rearranged T-cell receptor gamma chain gene, V2-JP1", GenBank accession No. X57737, NCBI, Nov. 14, 2006, 8 pages [online] [retrieved on Jun. 26, 2013] Retrieved from the internet <URL:http://www.ncbi.nlm.nih.gov/nuccore/x57737>.

Alexandre, D. et al. "*H. sapiens* rearranged T-cell receptor gamma chain gene, V3RS-J1 (hybrid joint)", GenBank accession No. X57740, NCBI, Feb. 11, 1997, 8 pages [online] [retrieved on Jun. 26, 2013] Retrieved from the internet <URL:http://www.ncbi.nlm.nih.gov/nuccore/x57740>.

Altman, et al. "Phenotypic analysis of antigen-specific T lymphocytes", The *Journal of Immunology*, 187(1):7-9 (2011).

Andreasson, et al. "The human IgE-encoding transcriptome to assess antibody repertoires and repertoire evolution", *J Mol Biol.*, 362(2):212-227 (2006). Epub Aug. 14, 2006.

Armand, P. et al., "Detection of circulating tumour DNA in patients with aggressive B-cell non-Hodgkin lymphoma", *Brit. J. Haematol.*, vol. 163, pp. 123-126 (2013).

Arstila, T.P., et al., "A direct estimate of the human αβ0 T cell receptor diversity," *Science*, 286(5441): 958-961 (1999).

Aslanzadeh. "Preventing PCR amplification carryover contamination in a clinical laboratory", *Ann Clin Lab Sci.*, 34(4):389-396 (2004).

Assaf, et al. "High Detection Rate of T-Cell Receptor Beta Chain Rearrangements in T-Cell Lymphoproliferations by Family Specific Polymerase Chain Reaction in Combination with the Genescan Technique and DNA Sequencing", *Blood*, 96(2): 640-646 (2000).

(56) References Cited

OTHER PUBLICATIONS

Babrzadeh et al. "Development on High-throughput Sequencing Technology: emPCR Titration and Barcode Design", *Stanford School of Medicine*, 2 pages (2011).
Bagnara, et al. "IgV gene intraclonal diversification and clonal evolution in B-cell chronic lymphocytic leukaemia", *British Journal of Haematology*, 133(1):50-58 (2006).
Barker, et al. "A second type II restriction endonuclease from Thermus aquaticus with an unusual sequence specificity", *Nucleic Acids Res.*, 12(14): 5567-5581 (1984).
Baum and McCune et al. "Direct measurement of T-cell receptor repertoire diversity with AmpliCot", *Nat Methods*, 3(11): 895-901 (2006).
Becton-Dickinson, CD marker handbook. bdbiosciences.com/go/mousecdmarkers, p. 1-47 (2010).
Becton-Dickinson T-Cell Research Tools, "Novel multicolor flow cytometry tools for the study of CD4+ T-cell differentiation and plasticity", 16 pages (2009).
Beishuizen, et al. "Analysis of Ig and T-cell receptor genes in 40 childhood acute lymphoblastic leukemias at diagnosis and subsequent relapse: implications for the detection of minimal residual disease by polymerase chain reaction analysis", *Blood*, 83(8):2238-2247 (1994).
Béné and Kaeda, "How and why minimal residual disease studies are necessary in leukemia: a review from WP10 and WP12 of the European LeukaemiaNet", *Haematologica*, 94(8):1135-1150 (2009).
Benichou, J. et al., "Rep-Seq: uncovering the immunological repertoire through next-generation sequencing", *Immunology*, 135(3): 183-191 (2011).
Benichou, J. et al., "The restricted DH gene reading frame usage in the expressed human antibody repertoire is selected based upon its amino acid content", *J Immunol.*, 190(11): 5567-77, 29 pages (2013).
Berger, et al. "The clonotypic T cell receptor is a source of tumor-associated antigens in cutaneous T cell lymphoma", *Annals of the New York Academy of Sciences*, 941:106-122, Abstract Only (2001).
Berget, et al. "Detection of clonality in follicular lymphoma using formalin-fixed, paraffin-embedded tissue samples and BIOMED-2 immunoglobulin primers", J Clin Pathol., 64(1):37-41 (2011). doi: 10.1136/jcp.2010.081109. Epub Oct. 28, 2010.
Bernard et al. "Color multiplexing hybridization probes using the apolipoprotein E locus as a model system for genotyping", Anal Biochem., 273(2):221-228 (1999).
Bernardin, F. et al., "Estimate of the total number of CD8+ clonal expansions in healthy adults using a new DNA heteroduplex-tracking assay for CDR3 repertoire analysis", *Journal of Immunological Methods*, 274(1-2):159-175 (2003).
Bertness, et al. "T-Cell Receptor Gene Rearrangements as Clinical Markers of Human T-Cell Lymphomas", *The New England Journal of Medicine*, 313:534-538 (1985).
Biggerstaff, et al. "Enumeration of leukocyte infiltration in solid tumors by confocal laser scanning microscopy", *BMC Immunol.*, 7:16, 13 pages (2006).
Brochet et al. "IMGT/V-QUEST: the highly customized and integrated system for IG and TR standardized V-J and V-D-J sequence analysis", *Nucleic Acids Research*, vol. 36, Web Server issue W503-W508 (2008).
Bolotin, D.A. et al., "Next generation sequencing for TCR repertoire profiling: Platform-specific features and correction algorithms", *Eur. J. Immunol.*, 42:3073-3083 (2012).
Bonarius, H.P.J. et al. "Monitoring the T-Cell Receptor Repertoire at Single-Clone Resolution", *PLOS One*, 1(e55):1-10 (2006).
Boria, et al. "Primer sets for cloning the human repertoire of T cell receptor variable regions", *BMC Immunology*, 9:50, 9 pages (2008).
Borst, et al. "False-positive results and contamination in nucleic acid amplification assays: suggestions for a prevent and destroy strategy", Eur J Clin Microbiol Infect Dis., 23(4):289-299, Abstract Only (2004). Epub Mar. 10, 2004.

Boudinot et al. "New perspectives for large-scale repertoire analysis of immune receptors", *Molecular Immunology*, 45: 2437-2445 (2008).
Boyce, et al. "Human regulatory T-cell isolation and measurement of function", *BD Biosciences*, pp. 1-20 (2010).
Boyd, S.D. et al., "Individual Variation in the Germline Ig Gene Repertoire Inferred from Variable Region Gene Rearrangements", *The Journal of Immunology*, 184(12): 6986-6992 (2010). Epub 2010.
Boyd, S.D. et al., "Measurement and Clinical Monitoring of Human Lymphocyte Clonality by Massively Parallel V-D-J Pyrosequencing," *Science Translational Medicine*, 1:12ra23, 40 pages, including Supplementary Materials (2009).
Bradfield, et al. "Graft-versus-leukemia effect in acute lymphoblastic leukemia: the importance of tumor burden and early detection", Leukemia, 18(6): 1156-1158 (2004).
Brehm-Stecher and Johnson. "Single-cell microbiology: tools, technologies, and applications", *Microbiology and Molecular Biology Reviews*, 68(3):538-559 (2004).
Brenan, C. et al., "High throughput, nanoliter quantitative PCR," *Drug Discovery Today: Technologies*, 2(3):247-253 (2005).
Brennan et al. "Predictable αβ T-cell receptor selection toward an HLA-B*3501-restricted human cytomegalovirus epitope", J. Virol., 81(13): 7269-7273 (2007).
Brisco, et al. "Determining the repertoire of IGH gene rearrangements to develop molecular markers for minimal residual disease in B-lineage acute lymphoblastic leukaemia", *J Mol Diagn.*, 11(3):194-200 (2009).
Brisco, et al. "Outcome prediction in childhood acute lymphoblastic leukaemia by molecular quantification of residual disease at the end of induction", *Lancet*, 343:196-200 (1994).
Brody, et al. "Active and passive immunotherapy for lymphoma: proving principles and improving results", J Clin Oncol., 29(14):1864-1875, Abstract Only (2011). doi: 10.1200/JCO.2010.33.4623. Epub Apr. 11, 2011.
Brody, et al., "Immunotransplant for mantle cell lymphoma: Phase I/II study preliminary results", *Journal of Clinical Oncology*, ASCO Annual Meeting Abstracts Part 1, Suppl; abstr 2509: vol. 29, No. 15, 1 page (2011).
Brüggemann, et al. "Clinical significance of minimal residual disease quantification in adult patients with standard-risk acute lymphoblastic leukemia", *Blood*, 107(3):1116-1123 (2006). Epub Sep. 29, 2005.
Brüggemann, et al. "Rearranged T-cell receptor beta genes represent powerful targets for quantification of minimal residual disease in childhood and adult T-cell acute lymphoblastic leukemia", *Leukemia*, 18(4): 709-719 (2004).
Brüggemann, et al. "Standardized MRD quantification in European ALL trials: proceedings of the Second International Symposium on MRD assessment in Kiel, Germany, Sep. 18-20, 2008", *Leukemia*, 24(3):521-535 (2010). doi: 10.1038/leu.2009.268. Epub Dec. 24, 2009.
Buccisano, et al. "Prognostic and therapeutic implications of minimal residual disease detection in acute myeloid leukemia", Blood, 119(2):332-341 (2012). doi: 10.1182/blood-2011-08-363291. Epub Oct. 28, 2011.
Buccisano, et al. "Monitoring of minimal residual disease in acute myeloid leukemia", Curr Opin Oncol., 21(6):582-588, Abstract Only (2009). doi: 10.1097/CCO.0b013e3283311856.
Butkus, B. "Hutch Team Uses ddPCR to Quantify T-Cell Response in Tumors; Adaptive Biotech Eyes Market", *PCR Insider*, Dec. 12, 2013, 3 pages http://www.genomeweb.com/print/1323296.
Bystrykh. "Generalized DNA Barcode Design Based on Hamming Codes", *PLoS ONE*, 7(5): e36852, 1-8 (2012).
Campana. "Minimal residual disease in acute lymphoblastic leukemia", *Semin Hematol.*,46(1):100-106 (2009).
Campana, et al. "Role of minimal residual disease monitoring in adult and pediatric acute lymphoblastic leukemia", *Hematol Oncol Clin North Am.*, 23(5): 1083-1098 (2009). doi: 10.1016/j.hoc.2009.07.010.
Campbell et al. "Subclonal phylogenetic structures in cancer revealed by ultra-deep sequencing," *PNAS*, 105(35):13081-13086 (2008).

(56) References Cited

OTHER PUBLICATIONS

Caporaso, J.G. et al. "Global patterns of 16S rRNA diversity at a depth of millions of sequences per sample", PNAS, 108(Suppl. 1):4516-4522 (2010).

Carlotti, et al. "Transformation of follicular lymphoma to diffuse large B-cell lymphoma may occur by divergent evolution from a common progenitor cell or by direct evolution from the follicular lymphoma clone", Blood, 113(15): 3553-3557 (2009). doi: 10.1182/blood-2008-08-174839. Epub Feb. 6, 2009.

Carlson et al. "Profiling the repertoire of TCRB usage in induced and natural Treg cells", The Journal of Immunology, 186: 62.5, Abstract (2011).

Carlson, et al. "Deep sequencing of the human TCRγ and TCRβ repertoires provides evidence that TCRβ rearranges after αγ, γδT cell commitment". Presented at the ASHG 2011 Conference. Oct. 2011. Poster. 1 page.

Carlson, C.S. et al. "Using synthetic templates to design an unbiased multiplex PCR assay", Nature Communications, 4:2680, pp. 1-9 (2013).

Casali, et al. "Human monoclonals from antigen-specific selection of B lymphocytes and transformation by EBV", Science, 234(4775): 476-479, Abstract Only (1986).

Casbon et al. "A method for counting PCR template molecules with application to next-generation sequencing", Nucleic Acids Research, 39(12): e81, 8 pages (2011).

Catherwood, M.A. et al., "Improved clonality assessment in germinal centre/post germinal centre non-Hodgkin's lymphomas with high rates of somatic hypermutation", J. Clin. Pathol., 60:524-528, Abstract (2007).

Cha et al., "Effect of anti-CTLA-4 antibody treatment on T-cell repertoire evolution in treated cancer patients." Journal of Clinical Oncology, 2013 ASCO Annual Meeting Abstracts; vol. 31, No. 15_suppl (May 20 Supplement), 2013: 3020, 1 page.

Chan et al. "Evaluation of Nanofluidics Technology for High-Throughput SNP Genotyping in a Clinical Setting", The Journal of Molecular Diagnostics, 13(3): 305-312 (2011).

Chen et al. "A novel approach for the analysis of T-cell reconstitution by using a T-cell receptor β-based oligonucleotide microarray in hematopoietic stem cell transplantation", Exp Hematol., 35(5):831-841 (2007).

Chen, et al. "Microfluidic cell sorter with integrated piezoelectric actuator", Biomed Microdevices, 11(6): 1223-1231 (2009). doi: 10.1007/s10544-009-9341-5.

Chen, Y. et al., "T-cell receptor gene expression in tumour-infiltrating lymphocytes and peripheral blood lymphocytes of patients with nasopharyngeal carcinoma", British Journal of Cancer, 72(1): 117-22 (1995).

Chinese Application No. 201380042163.X, Search Report dated Apr. 12, 2016 (English translation), 2 pages.

Chinese Patent Application No. 2014800254909, Search Report and English translation, dated May 25, 2017, mailed by the Chinese Patent Office dated Jun. 6, 2017, 5 pages.

Chiu, et al. "Non-invasive prenatal assessment of trisomy 21 by multiplexed maternal plasma DNA sequencing: large scale validity study", BMJ, 342:c7401, 9 pages (2011). doi: 10.1136/bmj.c7401.

Choi, et al. "Relapse in children with acute lymphoblastic leukemia involving selection of a preexisting drug-resistant subclone", Blood, 110(2):632-639 (2007).

Choi, et al. "Clonal evolution in B-lineage acute lymphoblastic leukemia by contemporaneous $V_H$-$V_H$ gene replacements and $V_H$-$DJ_H$ gene rearrangements", Blood, 87(6):2506-2512 (1996).

Chothia, C. et al. "Canonical structures for the hypervariable regions of immunoglobulins," J. Mol. Biol., 196:901-917, Abstract only (1987).

Chothia, C. et al. "Conformations of immunoglobulin hypervariable regions," Nature, 342:877-883 (1989).

Churchill and Waterman. "The Accuracy of DNA Sequences: Estimating Sequence Quality", Genomics, 14:89-98 (1992).

Chute, et al. "Detection of immunoglobulin heavy chain gene rearrangements in classic Hodgkin lymphoma using commercially available BIOMED-2 primers", Diagn Mol Pathol., 17(2): 65-72 (2008). doi: 10.1097/PDM.0b013e318150d695.

Citri et al. "Comprehensive qPCR profiling of gene expression in single neuronal cells", Nature Protocols, 7(1): 118-127 (2012).

Cleary, et al. "Production of complex nucleic acid libraries using highly parallel in situ oligonucleotide synthesis", Nat Methods, 1(3): 241-248 (2004). Epub Nov. 18, 2004.

Clemente, et al. "Deep sequencing of the T-cell receptor repertoire in CD8+T-large granular lymphocyte leukemia identifies signature landscapes", Blood, 122(25): 4077-85 (2013). doi: 10.1182/blood-2013-05-506386. Epub Oct. 22, 2013.

Craig et al. "Identification of genetic variants using bar-coded multiplex sequencing", Nature Methods, 5(10): 887-893 (2008) and Supplemental Materials.

Cronin, et al. "Comprehensive next-generation cancer genome sequencing in the era of targeted therapy and personalized oncology", Biomark Med., 5(3):293-305 (2011). (Abstract only). doi: 10.2217/bmm.11.37.

Cronn et al. "Multiplex sequencing of plant chloroplast genomes using Solexa sequencing-by-synthesis technology", Nucleic Acids Research, 36(19):e122, 1-11 (2008).

Curran et al. "Nucleotide sequencing of psoriatic arthritis tissue before and during methotrexate administration reveals a complex inflammatory T cell infiltrate with very few clones exhibiting features that suggest they drive the inflammatory process by recognizing autoantigens", The Journal of Immunology, 172:1935-1944 (2004).

Curran-Everett, D., "Multiple comparisons: philosophies and illustrations", Am J Physiol Regulatory Integrative Comp Physiol., 279:R1-R8 (2000).

Currier and Robinson. "Spectratype/immunoscope analysis of the expressed TCR repertoire", Current Protocols in Immunology, Supplement 38:10.28.1-10.28.24 (2000).

Dash, P. et al., "Paired analysis of TCR[alpha] and TCR[beta] chains at the single-cell level in mice", Journal of Clinical Investigation, 121(1):288-295 (2011).

Davi, et al. "Lymphocytic progenitor cell origin and clonal evolution of human B-lineage acute lymphoblastic leukemia", Blood, 88(2):609-621 (1996).

Davis, et al. "Interrogating the repertoire: broadening the scope of peptide-MHC multimer analysis", Nat Rev Immunol., 11(8):551-558 (2011). doi: 10.1038/nri3020.

Davis, et al. "Staining of cell surface human CD4 with 2'-F-pyrimidine-containing RNA aptamers for flow cytometry", Nucleic Acids Research, 26(17):3915-3924 (1998).

Dean, et al. "Rapid amplification of plasmid and phage DNA using Phi 29 DNA polymerase and multiply-primed rolling circle amplification", Genome Res., 11(6): 1095-1099 (2001).

Dedhia, et al. "Evaluation of DNA extraction methods and real time PCR optimization on formalin-fixed paraffin-embedded tissues", Asian Pac J Cancer Prev., 8(1): 55-59 (2007).

DeKosky et al. "High-throughput sequencing of the paired human immunoglobulin heavy and light chain repertoire", Nature Biotechnology, 31(2): 166-169 (2013).

Deng et al. "Gene profiling involved in immature CD4+ T lymphocyte responsible for systemic lupus erythematosus", Molecular Immunology, 43:1497-1507 (2006).

Deschoolmeester, et al. "Tumor infiltrating lymphocytes: an intriguing player in the survival of colorectal cancer patients", BMC Immunology, 11:19, 12 pages (2010). doi: 10.1186/1471-2172-11-19.

Desmarais, et al. High-throughput sequencing of memory and naïve T cell receptor repertoires at the RNA and DNA levels reveals differences in relative expression of expanded TCR clones. Adaptive Technologies. Seattle W A. Poster, 1 page. Presented May 5, 2012.

Desmarais and Robins. "High-throughput sequencing of memory and naïve T cell receptor repertoires at the RNA and DNA levels reveals differences in relative expression of expanded TCR clones", The Journal of Immunology, 182: 178.12 (2012).

Dictor et al. "Resolving T-cell receptor clonality in two and genotype in four multiplex polymerase chain reactions", Haematologica, 90(11): 1524-1532 (2005).

(56) References Cited

OTHER PUBLICATIONS

Diederichsen, et al. "Prognostic value of the CD4+/CD8+ ratio of tumour infiltrating lymphocytes in colorectal cancer and HLA-DR expression on tumour cells", Cancer Immunol Immunother., 52(7):423-428 (2003). Epub Apr. 15, 2003.
Diehl, et al. "BEAMing: single-molecule PCR on microparticles in water-in-oil emulsions", Nat Methods, 3(7):551-559, Abstract Only (2006).
Ding, et al. "Clonal evolution in relapsed acute myeloid leukaemia revealed by whole-genome sequencing", Nature, 481(7382):506-510 (2012). doi: 10.1038/nature10738.
Diviacco, et al. "A novel procedure for quantitative polymerase chain reaction by coamplification of competitive templates", Gene, 122(2):313-320 (1992).
Dobosy, J. et al. "RNase H-dependent PCR (rhPCR): improved specificity and single nucleotide polymorphism detection using blocked cleavable primers", BMC Biotechnology, 11(80):1-18 (2011).
Dohm, et al. "Substantial biases in ultra-short read data sets from high throughput DNA sequencing", Nucleic Acids Research, 36:e105, 10 pages (2008).
Dou, et al. "Analysis of T cell receptor $V_\beta$ gene usage during the course of disease in patients with chronic hepatitis B", Journal of Biomedical Science, 5(6):428-434 (1998).
Dressman, et al. "Transforming single DNA molecules into fluorescent magnetic particles for detection and enumeration of genetic variations", PNAS, 100(15):8817-8822 (2003). Epub Jul. 11, 2003.
Drmanac, et al. "Human genome sequencing using unchained base reads on self-assembling DNA nanoarrays", Science, 327(5961):78-81 (2010). doi: 10.1126/science.1181498. Epub Nov. 5, 2009.
Droege, et al. "The Genome Sequencer FLX System—longer reads, more applications, straight forward bioinformatics and more complete data sets", J Biotechnol., 136(1-2):3-10 (2008). doi: 10.1016/j.jbiotec.2008.03.021. Epub Jun. 21, 2008.
Droese, J., et al. "Validation of BIOMED-2 multiplex PCR tubes for detection of TCRB gene rearrangements in T-cell malignancies," Leukemia, 18:1531-1538 (2004).
Du et al. "TCR spectratyping revealed T lymphocytes associated with graft-versus-host disease after allogeneic hematopoietic stem cell transplantation", Leukemia & Lymphoma, 48(8):1618-1627 (2007).
Dueñas, M., et al. "In vitro immunization of naive human B cells yields high affinity immunoglobulin G antibodies as illustrated by phage display." Immunology (1996); 89.1: 1-7.
Dunn, et al. "Focus on TILs: Prognostic significance of tumor infiltrating lymphocytes in human glioma", Cancer Immun., 7:12, 16 pages (2007).
Eason et al. "Characterization of synthetic DNA bar codes in Saccharomyces cerevisiae gene-deletion strains," PNAS, 101(30):11046-11051 (2004).
Edd et al. "Controlled encapsulation of single cells into monodisperse picoliter drops", Lab Chip, 8(8):1262-1264 (2008).
Eichler, et al. "Haplotype and interspersion analysis of the FMR1 CGG repeat identifies two different mutational pathways for the origin of the fragile X syndrome", Hum Mol Genet., 5(3):319-330 (1996).
Eichler, et al. "Length of uninterrupted CGG repeats determines instability in the FMR1 gene", Nat Genet., 8(1):88-94, Abstract Only (1994).
Eid et al. "Real-time DNA sequencing from single polymerase molecules", Science, 323(5910):133-138 (2009). doi: 10.1126/science.1162986. Epub Nov. 20, 2008.
Eis, et al. "An invasive cleavage assay for direct quantitation of specific RNAs", Nat Biotechnol., 19(7):673-676, Abstract Only (2001).
Eisenstein. "Personalized, sequencing-based immune profiling spurs startups", Nat Biotechnol., 31(3):184-186 (2013). doi: 10.1038/nbt0313-184b.
Elkord et al. "T regulatory cells in cancer: recent advances and therapeutic potential", Expert Opinion on Biological Therapy, 10(11):1573-1586 (2010).

Emerson, et al. "Correlation of TCR diversity with immune reconstitution after cord blood transplant", Presented at the American Society of Clinical Oncology's annual meeting. May 2012. Poster. 1 page.
Emerson et al. "Defining the Alloreactive T Cell Repertoire Using High-Throughput Sequencing of Mixed Lymphocyte Reaction Culture", PLoS One, 9(11): e111943 (2014).
Emerson, R.O. et al. "High-throughput sequencing of T-cell receptors reveals a homogeneous repertoire of tumour-infiltrating lymphocytes in ovarian cancer", Journal of Pathology, 231: 433-440 (2013).
Emerson, et al. "CD4+ and CD8+ T cell β antigen receptors have different and predictable V and J gene usage and CDR3 lengths", Presented at the Annual Meeting of the American Association of Immunologists 2012 in Boston, MA May 2012. Poster.
Emerson, et al. "Estimating the ratio of CD4+ to CD8+ T cells using high-throughput sequence data", J Immunol Methods, 391(1-2):14-21 (2013). doi: 10.1016/j.jim.2013.02.002. Epub Feb. 18, 2013.
Estorninho, et al. "A novel approach to tracking antigen-experienced CD4 T cells into functional compartments via tandem deep and shallow TCR clonotyping", J Immunol., 191(11): 5430-5440 (2013). doi: 10.4049/jimmunol.1300622. Epub Oct. 25, 2013.
European Application No. 09764927.1, Notice of Opposition dated Oct. 14, 2014, Reference# 547-7.
European Application No. 09764927.1, Notice of Opposition dated Oct. 14, 2014, Reference# BR0-0001EP.
European Application No. 09764927.1, European Opposition dated Oct. 15, 2014 (in French only).
Esendagli et al. "Malignant and non-malignant lung tissue areas are differentially populated by natural killer cells and regulatory T cells in non-small cell lung cancer", Lung Cancer, 59(1): 32-40 (2008).
European Application No. 10732172.1, Extended European Search Report dated May 29, 2012, 5 pages.
European Application No. 16162568.6, Extended European Search Report dated Jul. 20, 2016, 6 pages.
European Patent Application No. 13195379.6, European Search Report and Opinion dated Mar. 13, 2014, 6 pages.
European Patent Application No. 11777704.5, European Search Report dated Jul. 26, 2013, 6 pages.
European Patent Application No. 16183402.3, Extended European Search Report dated Feb. 21, 2017, 8 pages.
European Patent Application No. 13828563.0, Extended European Search Report dated Feb. 12, 2016, 10 pages.
European Patent Application No. 13804085.2, Extended European Search Report dated Nov. 16, 2015, 10 pages.
European Patent Application No. 14819680.1, Extended European Search Report dated Feb. 10, 2017, 10 pages.
European Patent Application No. 13775514.6, Extended European Search Report dated Dec. 1, 2015, 12 pages.
European Patent Application No. 13757482.8, Extended European Search Report dated Jun. 6, 2016, 5 pages.
European Patent Application No. 16165939.6, Extended European Search Report dated Oct. 7, 2016, 9 pages.
European Patent Application No. 09764927.1, EPO's Communication of Notices of Opposition, dated Nov. 21, 2014.
European Patent Application No. 09764927.1, Patentee's Observations/Response dated May 27, 2015.
European Patent Application No. 09764927.1, Opponent's Response to Submission of the Patentee dated Nov. 23, 2015.
European Patent Application No. 15772627.4, Extended European Search Report dated Jul. 19, 2017, 8 pages.
European Patent Application No. 15779750.7, Extended European Search Report dated Aug. 9, 2017, 9 pages.
European Patent Application No. 15758762.7, Extended European Search Report dated Sep. 22, 2017, 12 pages.
Faham, M. et al. "Deep-sequencing approach for minimal residual disease detection in acute lymphoblastic leukemia", Blood, 120(26): 5173-5180 (2012).
Ferradini et al. "Analysis of T Cell Receptor Variability in Tumor-infiltrating Lymphocytes from a Human Regressive Melanoma", J. Clin. Invest., pp. 1183-1190 (1993).

(56) References Cited

OTHER PUBLICATIONS

Ferrero, et al. "Multiple myeloma shows no intra-disease clustering of immunoglobulin heavy chain genes", Haematologica, 97(6): 849-853 (2012). doi: 10.3324/haematol.2011.052852. Epub Dec. 29, 2011.
Flaherty et al. "Ultrasensitive detection of rare mutations using next-generation targeted resequencing", Nucleic Acids Research, 40(1): e2, 12 pages (2012).
Flohr, T., et al. "Minimal residual disease-directed risk stratification using real-time quantitative PCT analysis of immunoglobulin and T-cell receptor gene rearrangements in the international multicenter trial AIEOP-BFM ALL 2000 for childhood acute lymphoblastic leukemia", Leukemia, 22:771-782 (2008).
Frank. "BARCRAWL and BARTAB: software tools for the design and implementation of barcoded primers for highly multiplexed DNA sequencing," BMC Bioinformatics, 10: 362 (2009).
Frederiksson et al., "Multiplex amplification of all coding sequences within 10 cancer genes by Gene-Collector", Nucleic Acids Research, 35(7): e47 (2007).
Freeman, et al. "Quantitative RT-PCR: Pitfalls and Potential", Biotechniques, 6(1): 112-125 (1999).
Freeman, J.D., et al. "Profiling the T-Cell Receptor Beta-Chain Repertoire by Massively Parallel Sequencing", Genome Research, 19(10):1817-1824 (2009). Epub Jun. 18, 2009.
Fridman, et al. "Prognostic and predictive impact of intra- and peritumoral immune infiltrates", Cancer Research, 71(17): 5601-5605 (2011). doi: 10.1158/0008-5472.CAN-11-1316. Epub Aug. 16, 2011.
Fritz et al. "Alterations in the spinal cord T cell repertoire during relapsing experimental autoimmune encephalomyelitis," J Immunol, 164:6662-6668 (2000).
Fu et al. "Counting individual DNA molecules by the stochastic attachment of diverse labels", PNAS, 108(22): 9026-9031 and Supporting Materials, 8 pages (2011).
Fuller, et al. "The challenges of sequencing by synthesis", Nat Biotechnol., 7(11): 1013-1023 (2009) (Abstract only). doi: 10.1038/nbt.1585. Epub Nov. 6, 2009.
García-Castillo and Núnez, et al. "Detection of clonal immunoglobulin and T-cell receptor gene recombination in hematological malignancies: monitoring minimal residual disease", Cardiovascular & Haematological Disorders-Drug Targets, 9:124-135 (2009).
Gauss, et al. "Mechanistic constraints on diversity in human V(D)J recombination", Mol Cell Biol., 16(1):258-269 (1996).
Gawad, et al. "Massive evolution of the immunoglobulin heavy chain locus in children with B precursor acute lymphoblastic leukemia", Blood, 120(22):4407-4417 (2012). doi: 10.1182/blood-2012-05-429811. Epub Aug. 28, 2012.
Georgiou, G., et al., "The promise and challenge of high-throughput sequencing of the antibody repertoire." Nat Biotechnol (2014); 32(2): 158-168.
Gerlinger and Swanton. "How Darwinian models inform therapeutic failure initiated by clonal heterogeneity in cancer medicine", British Journal of Cancer, 103(8):1139-1143 (2010). doi: 10.1038/sj.bjc.6605912. Epub Sep. 28, 2010.
Gerlinger, M. et al. "Ultra deep T cell receptor sequencing reveals the complexity and intratumour heterogeneity of T cell clones in renal cell carcinomas", Journal of Pathology, 231:424-432 (2013).
Germano, et al. "Clonality profile in relapsed precursor-B-ALL children by GeneScan and sequencing analyses. Consequences on minimal residual disease monitoring", Leukemia, 17(8):1573-1582 (2003).
Giannoni, et al. Allelic exclusion and peripheral reconstitution by TCR transgenic T cells arising from transduced human hematopoietic stem/progenitor cells, Mol Ther., 21(5):1044-1054 (2013). doi: 10.1038/mt.2013.8. Epub Feb. 5, 2013.
Gilbert, et al. "The isolation of nucleic acids from fixed, paraffin-embedded tissues-which methods are useful when?", PLoS One, 2(6):e537, 12 pages (2007).
Giuggio, et al. "Evolution of the intrahepatic T cell repertoire during chronic hepatitis C virus infection", Viral Immunology, 18(1):179-189 (2005).
Gloor et al. "Microbiome profiling by Illumina sequencing of combinatorial sequence-tagged PCR products," PLoS ONE, 5(10): e15406, 15 pages (2010).
Godelaine, et al. "Polyclonal CTL responses observed in melanoma patients vaccinated with dendritic cells pulsed with a MAGE-3.A1 peptide", J Immunol., 171(9):4893-4897 (2003).
Golembowski, et al. "Clonal evolution in a primary cutaneous follicle center B cell lymphoma revealed by single cell analysis in sequential biopsies", Immunobiology, 201(5):631-644 (2000).
Gonzalez, et al. "Incomplete DJH rearrangements of the IgH gene are frequent in multiple myeloma patients: immunobiological characteristics and clinical implications", Leukemia, 17:1398-1403 (2003).
Gonzalez et al., "Incomplete DJH rearrangements as a novel tumor target for minimal residual disease quantitation in multiple myeloma using real-time PCR", Leukemia, 17:1051-1057 (2003).
Gonzalez, S.F., et al. "Trafficking of B Cell Antigen in Lymph Nodes", Ann. Rev. Immunol., 29: 215-233 (2011).
Gopalakrishnan, et al. "Unifying model for molecular determinants of the preselection Vβ repertoire", Proc Natl Acad Sci USA, 110(34):E3206-15 (2013). doi: 10.1073/pnas.1304048110. Epub Aug. 5, 2013.
Gorski, et al. "Circulating T cell repertoire complexity in normal individuals and bone marrow recipients analyzed by CDR3 size spectratyping. Correlation with immune status", J Immunol., 152(10):5109-5119 (1994).
Gottenberg, et al. "Markers of B-lymphocyte activation are elevated in patients with early rheumatoid arthritis and correlated with disease activity in the ESPOIR cohort", Arthritis Res Ther., 11(4): R114 (2009). doi: 10.1186/ar2773. Epub Jul. 23, 2009.
Gratama and Kern. "Flow cytometric enumeration of antigen-specific T lymphocytes", Cytometry A, 58(1): 79-86 (2004).
Gratama, et al. "Measuring antigen-specific immune responses", 2008 update. Cytometry A., 73(11): 971-974 (2008). doi: 10.1002/cyto.a.20655.
Green, et al. "Clonal diversity of Ig and T-cell-receptor gene rearrangements identifies a subset of childhood B-precursor acute lymphoblastic leukemia with increased risk of relapse", Blood, 92(3):952-958 (1998).
Greenberg, et al. "Profile of immunoglobulin heavy chain variable gene repertoires and highly selective detection of malignant clonotypes in acute lymphoblastic leukemia" J Leukoc Biol., 57(6):856-864 (1995).
Greenman, et al. "Patterns of somatic mutation in human cancer genomes", Nature, 446(7132): 153-158 (2007).
Grupp, et al. "Chimeric antigen receptor-modified T cells for acute lymphoid leukemia", N Engl J Med., 368(16):1509-1518 (2013). doi: 10.1056/NEJMoa1215134. Epub Mar. 25, 2013.
Gulliksen, et al. "Real-time nucleic acid sequence-based amplification in nanoliter volumes", Anal Chem., 76(1): 9-14, Abstract Only (2004).
Gunderson et al. "Decoding Randomly Ordered DNA Arrays", Genome Research, 14: 870-877 (2004).
Guo, et al. "Sequence changes at the V-D junction of the $V_H 1$ heavy chain of anti-phosphocholine antibodies alter binding to and protection against Streptococcus pneumoniae", Int Immunol., 9(5):665-677 (1997).
Gurrieri, et al. "Chronic lymphocytic leukemia B cells can undergo somatic hypermutation and intraclonal immunoglobulin $V_H DJ_H$ gene diversification", J Exp Med., 196(5):629-639 (2002).
Hadrup, et al. "Parallel detection of antigen-specific T-cell responses by multidimensional encoding of MHC multimers", Nat Methods, 6(7): 520-526 (2009) (Abstract Only). doi: 10.1038/nmeth.1345. Epub Jun. 21, 2009.
Halldórsdóttir, et al. "Application of BIOMED-2 clonality assays to formalin-fixed paraffin embedded follicular lymphoma specimens: superior performance of the IGK assays compared to IGH for suboptimal specimens", Leukemia & Lymphoma, 48(7): 1338-1343 (2007).

(56) References Cited

OTHER PUBLICATIONS

Hamady, et al. "Error-correcting barcoded primers for pyrosequencing hundreds of samples in multiplex", *Nature Methods*, 5(3):235-237 (2008). doi: 10.1038/nmeth.1184. Epub Feb. 10, 2008.
Han et al. "Immunorepertoire analysis by multiplex PCR amplification and high throughput sequencing", *The Journal of Immunology*, 182:42.6, 1 page (2009).
Hanahan, et al. "Hallmarks of cancer: the next generation", *Cell*, 144(5): 646-674 (2011). doi: 10.1016/j.cell.2011.02.013.
Harismendy et al. "Evaluation of next generation sequencing platforms for population targeted sequencing studies", *Genome Biology*, 10:R32, 13 pages (2009).
Hawkins, et al. "Whole genome amplification—applications and advances", *Curr Opin Biotechnol.*, 13(1): 65-67 (2002).
He, et al. "IgH gene rearrangements as plasma biomarkers in Non-Hodgkin's lymphoma patients", *Oncotarget*, 2(3): 178-185 (2011).
Heger, M. "Studies Highlight Challenges of Immune Repertoire Sequencing's Clinical Applicability", available at http://www.genomeweb.com/sequencing/studies-highlight-challenges-immune-repertoire-sequencings-clinical-applicabilit?hq_e=el&hq_m=966798&hq_l=10&hq_v=2357e2f0b3. Accessed Apr. 6, 2011.
Henegariu, O. et al., "Multiplex PCR: Critical Parameters and Step-By-Step Protocol," Biotechniques, Informa HealthCare, 23(3):504-511 (1997).
Hensel et al. "Simultaneous identification of bacterial virulence genes by negative selection", *Science*, 269(5222): 400-403 (1995).
Hill, et al. "Using ecological diversity measures with bacterial communities", *FEMS Microbiol Ecol.*, 43(1):1-11 (2003). doi: 10.1111/j.1574-6941.2003.tb01040.x.
Hirohata, et al. "Regulation of human B cell function by sulfasalazine and its metabolites", *Int Immunopharmacol.*, 2(5): 631-640, Abstract Only (2002).
Hodges, E. et al. "Diagnostic role of tests for T cell receptor (TCR) genes", *J Clin Pathol.*, 56(1): 1-11 (2003).
Holt. "Q &A: BC cancer agency's Robert Holt on sequencing the immune repertoire in immune reconstitution," *Genome Web* (www.genomeweb.com) Jun. 30, 2009.
Holt and Jones. "The new paradigm of flow cell sequencing", *Genome Research*, 18:839-846 (2008).
Hoogenboom, et al. "Multi-subunit proteins on the surface of filamentous phage: methodologies for displaying antibody (Fab) heavy and light chains", *Nucleic Acids Res.*, 19(15): 4133-4137 (1991).
Hoogendoorn, et al. "Primary allogeneic T-cell responses against mantle cell lymphoma antigen-presenting cells for adoptive immunotherapy after stem cell transplantation", *Clin Cancer Res.*, 11(14): 5310-5318 (2005).
Hoos, et al. "Improved endpoints for cancer immunotherapy trials", *J Natl Cancer Inst.*, 102(18): 1388-1397 (2010). doi: 10.1093/jnci/djq310. Epub Sep. 8, 2010.
Hosono, et al. "Unbiased whole-genome amplification directly from clinical samples", *Genome Res.*, 13(5): 954-964 (2003). Epub Apr. 14, 2003.
Hoven, et al. "Detection and isolation of antigen-specific B cells by the fluorescence activated cell sorter (FACS)", *J Immunol Methods*, 117(2): 275-284, Abstract Only, 2 pages (1989).
Howe, et al. "T cell receptor clonotype analysis of T cell responses: Diagnostic application of a clonotypic database", *Blood*, 102:Abstract 3918 (2003).
Huh, et al. "Microfluidics for flow cytometric analysis of cells and particles", *Physiol Meas.*, 26(3): R73-98, Abstract Only (2005). Epub Feb. 1, 2005.
Huijsmans, et al. "Comparative analysis of four methods to extract DNA from paraffin-embedded tissues: effect on downstream molecular applications", *BMC Res Notes*, 3:239, 9 pages (2010). doi: 10.1186/1756-0500-3-239.
Huse, et al. "Generation of a large combinatorial library of the immunoglobulin repertoire in phage lambda", *Science*, 246(4935): 1275-1281, Abstract Only (1989).
Hwang, H.Y. et al. "Identification of a Commonly used CDR3 Region of Infiltrating T Cells Expressing Vβ13 and Vβ15 Derived from Psoriasis Patients", *The Journal of Investigative Dermatology*, 120(3):359-364 (2003).
Iancu, et al. "Profile of a serial killer: cellular and molecular approaches to study individual cytotoxic T-cells following therapeutic vaccination", *J Biomed Biotechnol.*, 2011: 452606 (2011). doi: 10.1155/2011/452606. Epub Nov. 14, 2010.
Ilakovac, V., "Statistical hypothesis testing and some pitfalls." Biochemia Medica (2009); 19(1): 10-16, 4 pages. [online]. [Retrieved on Apr. 12, 2016]. Retrieved from the Internet: <URL:http://www.biochemia-medica.com/contentlstatistical-hypothesis-testing-and-some-pitfalls>PDF.
Illumina. Data Sheet: Sequencing. Genomic Sequencing. Pub. No. 770.2008-016 Reference states: "Current as of Jan. 30, 2009", 6 pages, Copyright 2010.
Illumina. Data Sheet, "TruSeq™ exome enrichment kit", 5 pages (2011).
Illumina Systems & Software, Technology Spotlight, DNA Sequencing with Solexa® Technology, Illumina, Inc., Pub. No. 770-2007-002, 4 pages (2007).
Illumina. "Technical Note: Systems and Software. Calling sequencing SNPs", 3 pages (2010).
Illumina. TruSeq Sample Preparation Kit and Data Sheet. Illumina, Inc., San Diego, CA, 4 pages (2011).
Ishii et al. "Isolation and expression profiling of genes upregulated in the peripheral blood cells of systemic lupus erythematosus patients," *DNA Research*, 12:429-439 (2005).
Jabara et al. "Accurate sampling and deep sequencing of the HIV-1 protease gene using a Primer ID", *PNAS*, 108(50): 20166-20171 (2011).
Jacobi et al. "Activated memory B cell subsets correlate with disease activity in systemic lupus erythematosus: delineation by expression of CD27, IgD, and CD95", *Arthritis & Rheumatism*, 58(6):1762-1773 (2008).
Jacobi et al. "Correlation between circulating CD27$^{high}$ plasma cells and disease activity in patients with systemic lupus erythematosus" *Arthritis & Rheumatism*, 48(5):1332-1342 (2003).
Jaffe, et al. "Classification of lymphoid neoplasms: the microscope as a tool for disease discovery", *Blood*, 112(12): 4384-4399 (2008). doi: 10.1182/blood-2008-07-077982.
Jalla, et al. "Enumeration of lymphocyte subsets using flow cytometry: Effect of storage before and after staining in a developing country setting", *Indian J Clin Biochem.*, 19(2): 95-99 (2004). doi: 10.1007/BF02894264.
Jena, et al. "Amplification of genes, single transcripts and cDNA libraries from one cell and direct sequence analysis of amplified products derived from one molecule", *J. Immunol. Methods*, 190:199-213 (1996).
Jochems and Schlom. "Tumor-infiltrating immune cells and prognosis: the potential link between conventional cancer therapy and immunity", *Exp Biol Med* (Maywood), 236(5): 567-579 (2011). doi: 10.1258/ebm.2011.011007. Epub Apr. 12, 2011.
Jung, et al. "Unraveling V(D)J recombination; insights into gene regulation", *Cell*, 116(2): 299-311 (2004).
Jurkat, Clone 6-1 (ATCC TIB-152) Webpage retrievable from the ATCC under http://www.lgcstandards-atcc.org/Products/ All MB-152. aspx#characteristics. Accessed Oct. 14, 2014.
Kanda, et al. "Immune recovery in adult patients after myeloablative dual umbilical cord blood, matched sibling, and matched unrelated donor hematopoietic cell transplantation", *Biol Blood Marrow Transplant*, 18(11):1664-1676 (2012). doi: 10.1016/j.bbmt.2012.06.005. Epub Jun. 12, 2012.
Kato et al. "Analysis of accumulated T cell clonotypes in patients with systemic lupus erythematosus," *Arthritis & Rheumatism*, 43(12):2712-2721 (2000).
Katz, S.C. et al. "T Cell Infiltrate Predicts Long-Term Survival Following Resection of Colorectal Cancer Liver Metastases," Ann. Surg. Oncol., 16:2524-2530 (2009).
Kedzierska, et al. "Tracking phenotypically and functionally distinct T cell subsets via T cell repertoire diversity", *Mol Immunol.*, 45(3): 607-618 (2008). Epub Aug. 24, 2007.

(56) References Cited

OTHER PUBLICATIONS

Kiianitsa, et al., "Development of Tools for T-Cell Repertoire Analysis (TCRB Spectratyping) for the Canine Model of Hematopoietic Cell Transplantation", Blood, ASH—Annual Meeting Abstracts, 110:Abstract 4873, 2 pages (2007).
Kim, et al. "An efficient and reliable DNA extraction method for preimplantation genetic diagnosis: a comparison of allele drop out and amplification rates using different single cell lysis methods", Fertility and Sterility, 92: 814-818 (2009).
Kim, et al. "Polony multiplex analysis of gene expression (PMAGE) in mouse hypertrophic cardiomyopathy", Science, 316(5830):1481-1484 (2007).
Kinde et al. "Detection and quantification of rare mutations with massively parallel sequencing," PNAS, 108(23): 9530-9535 and Supporting Information, 16 pages (2011).
Kircher, et al. "Improved base calling for the Illumina Genome Analyzer using machine learning strategies", Genome Biol., 10(8): R83, 9 pages (2009). doi: 10.1186/gb-2009-10-8-r83. Epub Aug. 14, 2009.
Kirsch, et al. "High-throughput TCR sequencing provides added value in the diagnosis of cutaneous T-cell lymphoma", Presented for the 2014 ASH Annual meeting. Poster. 1 page. Dec. 5-9, 2014.
Kita, et al. "T cell receptor clonotypes in skin lesions from patients with systemic lupus erythematosus", Journal of Investigative Dermatology,110(1): 41-46 (1988).
Kivioja et al. "Counting absolute numbers of molecules using unique molecular identifiers," Nature Methods, 9(1): 72-76 (2012).
Klarenbeek, P.L. et al. "Deep sequencing of antiviral T-cell responses to HCMV and EBV in humans reveals a stable repertoire that is maintained for many years." PLoS Pathogens (2012); 8.9: e1002889.
Klarenbeek, P.L. et al. "Human T-cell memory consists mainly of unexpanded clones", Immunology Letters, 133: 42-48 (2010).
Klinger et al. "Combining next-generation sequencing and immune assays: a novel method for identification of antigen-specific T cells", PLoS One, 8(9): e74231, 1-9 (2013).
Klenerman, et al. "Tracking T cells with tetramers: new tales from new tools", Nat Rev Immunol., 2(4):263-272 (2002).
Kneba, M., et al. "Analysis of Rearranged T-cell Receptor β-Chain Genes by Polymerase Chain Reaction (PCR) DNA Sequencing and Automated High Resolution PCR Fragment Analysis",Blood, 86:3930-3937 (1995).
Kneba, et al. "Characterization of clone-specific rearrangement T-cell receptor gamma-chain genes in lymphomas and leukemias by the polymerase chain reaction and DNA sequencing",Blood, 84(2):574-581 (1994).
Kobari, et al. "T cells accumulating in the inflamed joints of a spontaneous murine model of rheumatoid arthritis become restricted to common clonotypes during disease progression", Int Immunol., 16(1):131-138 (2004).
Koboldt et al., "VarScan: variant detection in massively parallel sequencing of individual and pooled samples", Bioinformatics, 25(17): 2283-2285 (2009).
Koch, et al. "Tumor infiltrating T lymphocytes in colorectal cancer: Tumor-selective activation and cytotoxic activity in situ," Ann Surg., 244(6): 986-992; discussion 992-993 (2006).
Kojima et al. "PCR amplification from single DNA molecules on magnetic beads in emulsion: application for high-throughput screening of transcription factor targets", Nucleic Acids Research, 33: 17, e150, 9 pages (2005).
Kohlmann, et al. "Integration of next-generation sequencing into clinical practice: are we there yet?", Semin Oncol., 39(1): 26-36, Abstract Only (2012). doi: 10.1053/j.seminoncol.2011.11.008.
Krause et al. "Epitope-Specific Human Influenza Antibody Repertoires Diversify by B Cell Intraclonal Sequence Divergence and Interclonal Convergence", The Journal of Immunology, 187: 3704-3711 (2011).
Krueger, et al. "Large scale loss of data in low-diversity illumina sequencing libraries can be recovered by deferred cluster calling", PLoS One, 6(1): e16607, 7 pages (2011). doi:10.1371/journal.pone. 0016607.

Ku, et al. "Exome sequencing: dual role as a discovery and diagnostic tool", Ann Neurol., 71(1):5-14, Abstract Only (2012). doi: 10.1002/ana.22647.
Kumar, et al. "PEG-labeled nucleotides and nanopore detection for single molecule DNA sequencing by synthesis", Sci Rep., 2:684, 8 pages (2012). Epub Sep. 21, 2012.
Kwak, et al. "Induction of immune responses in patients with B-cell lymphoma against the surface-immunoglobulin idiotype expressed by their tumors", N Engl J Med., 327(17):1209-1215 (1992).
Kyu et al. "Frequencies of human influenza-specific antibody secreting cells or plasmablasts post vaccination from fresh and frozen peripheral blood mononuclear cells", Journal of Immunological Methods, 340: 42-47 (2009).
Ladetto, et al., "Next-generation sequencing and real-time quantitative PCR for minimal residual disease (MRD) detection using the immunoglobulin heavy chain variable region: A methodical comparison in acute lymphoblastic leukemia (ALL), mantle cell lymphoma (MCL) and multiple myeloma (MM)", Blood, vol. 120 , No. 21, Abstract 788 (Conference Abstract), Entire Abstract (2012).
Ladetto, M. et al. "Real-time polymerase chain reaction in multiple myeloma: Quantitative analysis of tumor contamination of stem cell harvests", Experimental Hematology, 30:529-536 (2002).
Ladetto, M. et al. "Real-Time Polymerase Chain Reaction of Immunoglobulin Rearrangements for Quantitative Evaluation of Minimal Residual Disease in Multiple Myeloma", American Society for Blood and Marrow Transplantation, 6(3):241-253 (2000).
Langerak, et al. "Immunoglobulin/T-cell receptor clonality diagnostics", Expert Opin. Med. Diagn., 1(3):451-461 (2007).
Langerak, et al. "Polymerase chain reaction-based clonality testing in tissue samples with reactive lymphoproliferations: usefulness and pitfalls. A report of the BIOMED-2 Concerted Action BMH4-CT98-3936", Leukemia, 21(2):222-229 (2007).
Laplaud et al. "Blood T-cell receptor β chain transcriptome in multiple sclerosis. Characterization of the T cells with altered CDR3 length distribution", Brain, 127:981-995 (2004).
Laplaud et al. "Serial blood T cell repertoire alterations in multiple sclerosis patients; correlation with clinical and MRI parameters", Journal of Neuroimmunology, 177(1-2):151-160 (2006).
Larimore, K., et al. "Shaping of Human Germline IgH Repertoires Revealed by Deep Sequencing", The Journal of Immunology, 189(6): 3221-3230 (2012).
Lassmann, et al. "Application of BIOMED-2 primers in fixed and decalcified bone marrow biopsies: analysis of immunoglobulin H receptor rearrangements in B-cell non-Hodgkin's lymphomas", J Mol Diagn., 7(5): 582-591 (2005).
Lee, et al. "Characterization of circulating T cells specific for tumor-associated antigens in melanoma patients", Nat Med., 5(6): 677-685, Abstract Only (1999).
Lee, et al. "Prognostic implications of type and density of tumour-infiltrating lymphocytes in gastric cancer", Br J Cancer, 99(10): 1704-1711 (2008). doi: 10.1038/sj.bjc.6604738. Epub Oct. 21, 2008.
Lefranc. "IMGT, the international ImMunoGeneTics database", Nucleic Acids Res., 31(1):307-310 (2003).
Leiden, J.M. et al. "The Complete Primary Structure of the T-Cell Receptor Genes From an Alloreactive Cytotoxic Human T-Lymphocyte Clone", Immunogenetics, 24(1): 17-23 (1986).
Leisner, et al. "One-pot, mix-and-read peptide-MHC tetramers", PLoS One, 3(2):e1678, 11 pages (2008). doi: 10.1371/journal.pone. 0001678.
Leone, et al. "Molecular beacon probes combined with amplification by NASBA enable homogeneous, real-time detection of RNA", Nucleic Acids Research, 26(9): 2150-2155 (1998).
Leproust, et al. "Synthesis of high-quality libraries of long (150mer) oligonucleotides by a novel depurination controlled process", Nucleic Acids Res., 38(8): 2522-2540 (2010). doi: 10.1093/nar/gkq163. Epub Mar. 22, 2010.
Lessin, et al. "Molecular diagnosis of cutaneous T-cell lymphoma: polymerase chain reaction amplification of T-cell antigen receptor beta-chain gene rearrangements", J Invest Dermatol., 96(3): 299-302 (1991).
Li, et al. "Utilization of Ig heavy chain variable, diversity, and joining gene segments in children with B-lineage acute lymphoblastic

(56) References Cited

OTHER PUBLICATIONS leukemia: implications for the mechanisms of VDJ recombination and for pathogenesis", *Blood*, 103(12):4602-4609 (2004).

Li, et al. "An improved one-tube RT-PCR protocol for analyzing single-cell gene expression in individual mammalian cells", *Anal. Bioanal. Chem.*, 397: 1853-1859 (2010).

Li, et al. "β cell-specific CD4+ T cell clonotypes in peripheral blood and the pancreatic islets are distinct", *J Immunol.*, 183(11): 7585-7591 (2009). doi: 10.4049/jimmunol.0901587. Epub Nov. 16, 2009.

Li, et al. "Clonal rearrangements in childhood and adult precursor B acute lymphoblastic leukemia: a comparative polymerase chain reaction study using multiple sets of primers", *Eur J Haematol.*, 63(4):211-218 (1999).

Li, et al. "Detailed clonality analysis of relapsing precursor B acute lymphoblastic leukemia: implications for minimal residual disease detection", *Leukemia Research*, 25:1033-1045 (2001).

Li, et al. "Sequence analysis of clonal immunoglobulin and T-cell receptor gene rearrangements in children with acute lymphoblastic leukemia at diagnosis and at relapse: implications for pathogenesis and for the clinical utility of PCR-based methods of minimal residual disease detection", *Blood*, 102:4520-4526 (2003).

Liedtke, et al. "A comparison of methods for RNA extraction from lymphocytes for RT-PCR", *PCR Methods and Applications*, 4(3): 185-187 (1994).

Lin, et al. "Multiplex genotype determination at a large number of gene loci", *Proc Natl Acad Sci USA*, 93(6): 2582-2587 (1996).

Liu, et al. "CD127 expression inversely correlates with FoxP3 and suppressive function of human CD4+ T reg cells", *J Exp Med.*, 203(7): 1701-1711 (2006). Epub Jul. 3, 2006.

Logan, et al., "High-throughput immunoglobulin gene sequencing quantifies minimal residual disease in CLL with 10e-6 sensitivity and strongly predicts relapse after allogeneic hematopoietic cell transplantation", *Blood*, vol. 118 (21), Abstract 2542 (2011).

Logan, A.C. et al. "High-throughput VDJ sequencing for quantification of minimal residual disease in chronic lymphocytic leukemia and immune reconstitution assessment", *PNAS*, 108(52): 21194-21199 (2011). Epub Dec. 12, 2011.

Logan, et al., "Massively parallel immunoglobulin gene sequencing provides ultra-sensitive minimal residual disease detection and predicts post-transplant relapse in acute lymphoblastic leukemia by three to six months", *Blood*, vol. 118 (21), Abstract 4104 (2011).

Lorimer, I. A., and Pastan, Ira. "Random recombination of antibody single chain Fv sequences after fragmentation with DNaseI in the presence of Mn2+." Nucleic Acids Research (1995); 23.15: 3067-3068.

Lossos, et al. "Transformation of follicular lymphoma to diffuse large-cell lymphoma: alternative patterns with increased or decreased expression of c-myc and its regulated genes", *PNAS*, 99(13): 8886-8891 (2002). Epub Jun. 19, 2002.

Lovisa, et al. "IGH and IGK gene rearrangements as PCR targets for pediatric Burkitt's lymphoma and mature B-ALL MRD analysis", *Lab Invest.*, 89(10):1182-1186 (2009).

Lowman, et al. "Monovalent phage display: a method for selecting variant proteins from random libraries", *Methods: A Companion to Methods in Enzymology*, 3: 205-216, Abstract Only (1991).

Lúcio, P. et al. "Flow cytometric analysis of normal B cell differentiation: a frame of reference for the detection of minimal residual disease in precursor-B-ALL", *Leukemia*, 13:419-427 (1999).

Lyamichev, et al. "Polymorphism identification and quantitative detection of genomic DNA by invasive cleavage of oligonucleotide probes", *Nat Biotechnol.*, 17(3): 292-396 (1999).

Luo et al. "Analysis of the interindividual conservation of T cell receptor α- and β-chain variable regions gene in the peripheral blood of patients with systemic lupus erythematosus", *Clinical & Experimental Immunology*, 154(3):316-324 (2008).

Mackay, et al. "Real-time PCR in virology", *Nucleic Acids Res.*, 30(6): 1292-1305 (2002).

Malyguine, et al. "ELISPOT Assay for Monitoring Cytotoxic T Lymphocytes (CTL) Activity in Cancer Vaccine Clinical Trials", *Cells*, 1(2): 111-126 (2012). doi: 10.3390/cells1020111.

Manion et al., "Reducing Error in Next Generation Sequencing Data with NextGENe Software's Condensation Tool™", Mar. 2009, pp. 1-3.

Manrao, et al. "Reading DNA at single-nucleotide resolution with a mutant MspA nanopore and phi29 DNA polymerase", *Nat Biotechnol.*, 30(4): 349-353 (2012). doi: 10.1038/nbt.2171.

Mar et al. "Inferring steady state single-cell gene expression distributions from analysis of mesoscopic samples", *Genome Biology*, 7(12): R119, 12 pages (2006).

Mardis. "Next-generation DNA sequencing methods", *Annu. Rev. Genomics Hum. Genet.*, 9:387-402 (2008). doi: 10.1146/annurev.genom.9.081307.164359.

Margulies, et al. "Genome sequencing in microfabricated high-density picolitre reactors", *Nature*, 437(7057):376-380 (2005). Epub Jul. 31, 2005.

Mariani, S. et al., "Comprehensive assessment of the TCRBV repertoire in small T-cell samples by means of an improved and convenient multiplex PCR method," *Experimental Hematology*, 37(6):728-738 (2009).

Markoulatos, P. et al., "Multiplex Polymerase Chain Reaction: A Practical Approach", Journal of Clinical Laboratory Analysis, 16:47-51 (2002).

Martin-Jimenez, et al. "Molecular characterization of heavy chain immunoglobulin gene rearrangements in Waldenström's macroglobulinemia and IgM monoclonal gammopathy of undetermined significance", *Haematologica*, 92(5): 635-642 (2007).

Mary et al. "Analysis of gene expression at the single-cell level using microdroplet-based microfluidic technology", *Biomicrofluidics*, 5: 024109-1-024109-10 (2011).

Maryanski, J.L. et al., "A quantitative, single-cell PCR analysis of an antigen-specific TCR repertoire 8 selected during an in vivo CD8 response: direct evidence for a wide range of clone sizes with uniform tissue distribution", Molecular Immunology, 36:745-753 (1999).

Maślanka, K. et al., "Molecular Analysis of T-Cell Repertoires: Spectratypes Generated by Multiplex Polymerase Chain Reaction and Evaluated by Radioactivity or Fluorescence", *Human Technology*, 44(1):28-34 (1995).

Mato et al. "Correlation of clonal T cell expansion with disease activity in systemic lupus erythematosus", *Int Immunol.*, 9(4):547-554 (1997).

Matolcsy, et al. "Clonal evolution of B cells in transformation from low- to high-grade lymphoma", *Eur. J. Immunol.*,29(4):1253-1264 (1999).

Matsumoto et al. "CDR3 spectratyping analysis of the TCR repertoire in Myasthenia Gravis", *The Journal of Immunology*, 176:5100-5107 (2006).

Matsumoto et al. "Complementarity-determining region 3 spectratyping analysis of the TCR repertoire in multiple sclerosis", *The Journal of Immunology*, 170:4846-4853 (2003).

Mazor et al. "Antibody internalization studied using a novel IgG binding toxin fusion", *Journal of Immunological Methods*, 321: 41-59 (2007).

Mazumder, et al., "Detection of multiple myeloma cells in peripheral blood using high-throughput sequencing assay" *Blood*, vol. 120, No. 21, Abstract 321 (Conference Abstract), Entire Abstract (2012).

McCloskey et al. "Encoding PCR products with batch-stamps and barcodes," *Biochem. Genet.*, 45: 761-767 (2007).

McLean et al. "Recognition of human cytomegalovirus by human primary immunoglobulins identifies an innate foundation to an adaptive immune response", J. Immunol., 174(8): 4768-4778 (2005).

Mei et al. "Blood-borne human plasma cells in steady state are derived from mucosal immune responses", *Blood*, 113(11): 2461-2469 (2009).

Meijer et al. "Isolation of Human Antibody Repertoires with Preservation of the Natural Heavy and Light Chain Pairing", *J. Mol. Biol.*, 358: 764-772 (2006).

Meier, et al. "Fractal organization of the human T cell repertoire in health and after stem cell transplantation", Biol Blood Marrow Transplant., 19(3):366-77 (2013). doi: 10.1016/j.bbmt.2012.12.004. Epub Jan. 11, 2013.

(56) References Cited

OTHER PUBLICATIONS

Meier et al. "Simultaneous evaluation of T-cell and B-cell clonality, t(11;14) and t(14;18), in a single reaction by a four-color multiplex polymerase chain reaction assay and automated High-Resolution fragment analysis", *American Journal of Pathology*, 159(6): 2031-2043 (2001).
Meier, et al. "The influence of different stimulation conditions on the assessment of antigen-induced CD154 expression on CD4+ T cells", *Cytometry A.*, (11):1035-1042 (2008). doi: 10.1002/cyto.a.20640.
Meleshko, et al. "Rearrangements of IgH, TCRD and TCRG genes as clonality marker of childhood acute lymphoblastic leukemia", *Experimental Oncology*, 27(4):319-324 (2005).
Menezes et al. "A public T cell clonotype within a heterogeneous autoreactive repertoire is dominant in driving EAE", *J Clin Invest*, 117(8):2176-2185 (2007).
Merriam-Webster, 2 pages, (definition of "e.g.," accessed Apr. 25, 2014).
Merriam-Webster, 4 pages (definition of "substantial," accessed Apr. 25, 2014).
Metzker, "Sequencing Technologies—The Next Generation", *Nature Reviews, Genetics*, 11:31-46 (2010).
Meyer et al. "Targeted high-throughput sequencing of tagged nucleic acid samples", *Nucleic Acids Research*, 35(15): e97, 5 pages (2007).
Miceli and Parnes. "The roles of CD4 and CD8 in T cell activation", *Seminars in Immunology*, 3(3): 133-141 (1991). Abstract only.
Michálek, et al. "Detection and long-term in vivo monitoring of individual tumor-specific T cell clones in patients with metastatic melanoma", *J Immunol.*, 178(11):6789-6795 (2007).
Michálek, et al. "Identification and monitoring of graft-versus-host specific T-cell clone in stem cell transplantation", *The Lancet*, 361(9364): 1183-1185 (2003).
Miller, et al., "Assembly algorithms for next-generation sequencing data", Genomics, 95(6): 315-327 (2010).
Miltenyi, et al. "High gradient magnetic cell separation with MACS", *Cytometry*, 11(2): 231-238 (1990).
Miner et al. "Molecular barcodes detect redundancy and contamination in hairpin-bisulfite PCR", *Nucleic Acids Research*, 32(17): e135, 4 pages (2004).
Miqueu, P. et al. "Statistical analysis of CDR3 length distributions for the assessment of T and B cell repertoire biases", *Molecular Immunology*, 44:1057-1064 (2007).
Mitra, et al. "Fluorescent in situ sequencing on polymerase colonies", *Anal Biochem.*, 320(1): 55-65, Abstract Only (2003).
Miyashita, et al. "N-Methyl substituted 2',4'-BNANC: a highly nuclease-resistant nucleic acid analogue with high-affinity RNA selective hybridization", *Chem Commun* (Camb), (36): 3765-3767, Abstract Only (2007). Epub Jul. 9, 2007.
Moen, et al. "Immunoglobulin G and A antibody responses to Bacteroides forsyth and Prevotella intermedia in sera and synovial fluids of arthritis patients", *Clin Diagn Lab Immunol.*, 10(6): 1043-1050 (2003).
Molloy, et al. "Soluble T cell receptors: novel immunotherapies", *Curr Opin Pharmacol.*, 5(4): 438-443 (2005) (Abstract Only).
Monod, M.Y. et al. "IMGT/JunctionAnalysis: the first tool for the analysis of the immunogloblulin and T cell receptor complex V-J and V-D-J Junctions", *Bioinformatics*, 20(Suppl 1):i379-385 (2004).
Moody, et al. "Antigen-specific B cell detection reagents: use and quality control", *Cytometry A.*, 73(11): 1086-1092 (2008). doi: 10.1002/cyto.a.20599.
Morgan, et al. "Cancer regression in patients after transfer of genetically engineered lymphocytes", *Science*, 314(5796): 126-129 (2006). Epub Aug. 31, 2006.
Morozova et al. "Applications of New Sequencing Technologies for Transcriptome Analysis", *Annu. Rev. Genomics Hum. Genet.*, 10: 135-151 (2009).
Morrissy et al. "Next-generation tag sequencing for cancer gene expression profiling", *Genome Research*, 19: 1825-1835 (2009).
Moss, et al. "The human T cell receptor in health and disease", *Annu. Rev. Immunol.*, 10:71-96 (1992).
Moura, et al. "Alterations on peripheral blood B-cell subpopulations in very early arthritis patients", *Rheumatology* (Oxford), 49(6): 1082-1092 (2010). doi: 10.1093/rheumatology/keq029. Epub Mar. 7, 2010.
Muraro et al. "Molecular tracking of antigen-specific T cell clones in neurological immune-mediated disorders", *Brain*, 126(Pt 1):20-31 (2003).
Murugan, et al. "Statistical inference of the generation probability of T-cell receptors from sequence repertoires", *PNAS*, 109(40): 16161-16166 (2012). doi: 10.1073/pnas.1212755109. Epub Sep. 17, 2012.
Naito, et al. "CD8+ T cells infiltrated within cancer cell nests as a prognostic factor in human colorectal cancer", *Cancer Research*, 58(16): 3491-3494 (1998).
Nardi, et al. "Quantitative monitoring by polymerase colony assay of known mutations resistant to ABL kinase inhibitors", *Oncogene*, 27(6):775-782 (2008). Epub Aug. 6, 2007, 1-8.
Navarrete, et al. "Upfront immunization with autologous recombinant idiotype Fab fragment without prior cytoreduction in indolent B-cell lymphoma", *Blood*, 117(5): 1483-1491 (2011). doi: 10.1182/blood-2010-06-292342. Epub Nov. 2, 2010.
Neale, et al. "Comparative analysis of flow cytometry and polymerase chain reaction for the detection of minimal residual disease in childhood acute lymphoblastic leukemia", *Leukemia*, 18(5):934-938 (2004).
Needleman and Wunsch. "A general method applicable to the search for similarities in the amino acid sequence of two proteins", *J Mol Biol.*, 48(3): 443-453 (1970).
Nelson. "CD20+ B cells: the other tumor-infiltrating lymphocytes", *The Journal of Immunology*, 185(9): 4977-4982 (2010). doi: 10.4049/jimmunol.1001323.
Newman, et al. "Identification of an antigen-specific B cell population", *J Immunol Methods*, 272(1-2): 177-187, Abstract Only (2003).
Nguyen et al. "Identification of errors introduced during high throughput sequencing of the T cell receptor repertoire" *BMC Genomics*, 12: 106, 13 pages (2011).
Nielsen, et al. "Peptide nucleic acid (PNA). A DNA mimic with a pseudopeptide backbone", *Chem. Soc. Rev.*, 26:73-78, Abstract Only (1997).
Nosho, et al. "Tumour-infiltrating T-cell subsets, molecular changes in colorectal cancer, and prognosis: cohort study and literature review", *J Pathol.*, 222(4): 350-366 (2010). doi: 10.1002/path.2774.
Novak, et al. "Single Cell Multiplex Gene Detection and Sequencing Using Microfluidically-Generated Agarose Emulsions", *Angew Chem Int Ed Engl.*, 50(2): 390-395, with supplemental materials (2011).
Oble, et al. "Focus on TILs: prognostic significance of tumor infiltrating lymphocytes in human melanoma", *Cancer Immunity*, 9: 3, 20 pages (2009).
Oelke, et al. "Ex vivo induction and expansion of antigen-specific cytotoxic T cells by HLA-Ig-coated artificial antigen-presenting cells", *Nat Med.*, 9(5): 619-624 (2003). Epub Apr. 21, 2003.
Ogle, et al. "Direct measurement of lymphocyte receptor diversity", *Nucleic Acids Research*, 31(22):e139, 6 pages (2003).
Ohlin, Mats, et al. "Light chain shuffling of a high affinity antibody results in a drift in epitope recognition." Molecular Immunology (1996); 33.1: 47-56.
Ohtani. "Focus on TILs: prognostic significance of tumor infiltrating lymphocytes in human colorectal cancer", *Cancer Immunity*, 7: 4, 9 pages (2007).
Okajima et al. "Analysis of T cell receptor Vβ diversity in peripheral CD4$^+$ and CD8$^+$ T lymphocytes in patients with autoimmune thyroid diseases", *Clinical & Experimental Immunology*, 155:166-172 (2008).
Okello et al. "Comparison of methods in the recovery of nucleic acids from archival formalin-fixed paraffin-embedded autopsy tissues", *Anal Biochem.*, 400(1): 110-117 (2010). doi: 10.1016/j.ab.2010.01.014. Epub Jan. 15, 2010.
Ottensmeier, et al. "Analysis of VH genes in follicular and diffuse lymphoma shows ongoing somatic mutation and multiple isotype transcripts in early disease with changes during disease progression", *Blood*, 91(11): 4292-4299 (1998).

(56) References Cited

OTHER PUBLICATIONS

Packer and Muraro. "Optimized clonotypic analysis of T-cell receptor repertoire in immune reconstitution", *Experimental Hematology*, 35(3):516-521 (2007).
Palmowski, et al. "The use of HLA class I tetramers to design a vaccination strategy for melanoma patients", *Immunol Rev.*, 188: 155-163 (2002) (Abstract Only).
Pan, et al. "A new FACS approach isolates hESC derived endoderm using transcription factors", *PLoS One*, 6(3): e17536, 9 pages (2011). doi: 10.1371/journal.pone.0017536.
Panzer-Grümayer et al. "Immunogenotype changes prevail in relapses of young children with TEL-AML1-positive acute lymphoblastic leukemia and derive mainly from clonal selection", *Clin Cancer Research*, 11(21):7720-7727 (2005).
Parameswaran et al. "A pyrosequencing-tailored nucleotide barcode design unveils opportunities for large-scale sample multiplexing", *Nucleic Acids Research*, 35(19): e130, 9 pages (2007).
Parmigiani, et al. "Design and analysis issues in genome-wide somatic mutation studies of cancer", *Genomics*, 93(1): 17-21 (2009). doi: 10.1016/j.ygeno.2008.07.005. Epub Aug. 23, 2008.
Pasqual et al. "Quantitative and qualitative changes in V-J alpha rearrangements during mouse thymocytes differentiation: implication for a limited T cell receptor alpha chain repertoire", *Journal of Experimental Medicine*, 196(9): 1163-1173 (2002). XP002322207 ISSN: 0022-1007.
Peet. "The Measurement of Species Diversity", *Annual Review of Ecology and Systematics*, 5: 285-307, Abstract Only (1974).
Petrosino, et al. "Metagenomic pyrosequencing and microbial identification", *Clin Chem.*, 55(5): 856-866 (2009). doi: 10.1373/clinchem. 2008.107565. Epub Mar. 5, 2009.
PCT/US2009/006053, International Search Report dated Jun. 15, 2010, 6 pages.
PCT/US2009/006053, Written Opinion dated Jun. 15, 2010, 4 pages.
PCT/US2009/006053, International Preliminary Report on Patentability dated May 10, 2011, 5 pages.
PCT/US2010/021264, International Search Report and Written Opinion dated Apr. 14, 2010, 7 pages.
PCT/US2010/021264, International Preliminary Report on Patentability dated Jul. 19, 2011, 5 pages.
PCT/US2016/019343, International Preliminary Report on Patentability dated Aug. 29, 2017, 14 pages.
PCT/US2016/019343, International Search Report and Written Opinion dated Jul. 22, 2016, 23 pages.
PCT/US2016/025535, International Preliminary Report on Patentability dated Oct. 3, 2017, 7 pages.
PCT/US2016/025535, International Search Report and Written Opinion dated Jul. 11, 2016, 9 pages.
PCT/US2010/037477, International Search Report and Written Opinion dated Sep. 24, 2010, 10 pages.
PCT/US2010/037477, International Preliminary Report on Patentability dated Jan. 4, 2012, 7 pages.
PCT/US2011/000791, International Search Report and Written Opinion dated Sep. 22, 2011, 13 pages.
PCT/US2011/000791, International Preliminary Report on Patentability dated Nov. 6, 2012, 10 pages.
PCT/US2011/049012, International Search Report and Written Opinion dated Apr. 10, 2012, 9 pages.
PCT/US2011/049012, International Preliminary Report on Patentability dated Feb. 26, 2013, 5 pages.
PCT/US2013/028942, International Search Report and Written Opinion dated May 9, 2013, 10 pages.
PCT/US2013/028942, International Preliminary Report on Patentability dated May 5, 2015, 9 pages.
PCT/US2013/054189, International Search Report and Written Opinion dated Oct. 21, 2013, 10 pages.
PCT/US2013/054189, International Preliminary Report on Patentability dated Feb. 10, 2015, 7 pages.
PCT/US2013/035857, International Search Report and Written Opinion dated Aug. 7, 2013, 10 pages.
PCT/US2013/035857, International Preliminary Report on Patentability dated Oct. 14, 2014, 8 pages.
PCT/US2013/040221, International Search Report and Written Opinion dated Sep. 23, 2013, 15 pages.
PCT/US2013/040221, International Preliminary Report on Patentability dated Apr. 24, 2014, 41 pages.
PCT/US2013/045276, International Search Report and Written Opinion dated Jan. 29, 2014, 11 pages.
PCT/US2013/045276, International Preliminary Report on Patentability dated Dec. 16, 2014, 2014, 7 pages.
PCT/US2013/045994, International Search Report and Written Opinion dated Oct. 25, 2013, 15 pages.
PCT/US2013/045994, International Preliminary Report on Patentability dated Dec. 16, 2014, 10 pages.
PCT/US2013/051539, International Search Report and Written Opinion dated Nov. 27, 2013, 9 pages.
PCT/US2013/051539, International Preliminary Report on Patentability dated Jan. 27, 2015, 7 pages.
PCT/US2014/030859, International Search Report and Written Opinion dated Jul. 18, 2014, 14 pages.
PCT/US2014/030859, International Preliminary Report on Patentability dated Sep. 15, 2015, 8 pages.
PCT/US2014/044971, International Search Report and Written Opinion dated Oct. 30, 2014, 14 pages.
PCT/US2014/044971, International Preliminary Examination Report dated Jan. 6, 2016, 12 pages.
PCT/US2015/018967, International Search Report and Written Opinion dated Jul. 30, 2015, 17 pages.
PCT/US2015/018967, International Preliminary Report on Patentability dated Oct. 18, 2016, 11 pages.
PCT/US2015/019029, International Search Report and Written Opinion dated Sep. 15, 2015, 19 pages.
PCT/US2015/019029, International Preliminary Report on Patentability dated Sep. 6, 2016, 14 pages.
PCT/US2015/023915, International Search Report and Written Opinion dated Aug. 26, 2015, 11 pages.
PCT/US2015/023915, International Preliminary Report on Patentability dated Oct. 4, 2016, 7 pages.
PCT/US2015/058035, International Search Report and Written Opinion dated Jan. 29, 2016, 14 pages.
PCT/US2015/058035, International Preliminary Report on Patentability dated May 2, 2017, 8 pages.
Pekin, D. et al. "Quantitative and sensitive detection of rare mutations using droplet-based microfluidics", *Lab Chip*, 11(3): 2156-2166 (2011).
Pels et al. "Clonal evolution as pathogenetic mechanism in relapse of primary CNS lymphoma", *Neurology*, 63(1):167-169 (2004).
Perkel, J. "Overcoming the Challenges of Multiplex PCR", *Biocompare Editorial Article*, Oct. 23, 2012, 6 Pages, can be retrieved at URL:http://www.biocompare.com/Editorial-Articles/117895-Multiplex-PCR/>.
Pira et al. "Human naive CD4 T-cell clones specific for HIV envelope persist for years in vivo in the absence of antigenic challenge", *J Acquir Immune Defic Syndr.*, 40(2):132-139 (2005).
Plasilova et al. "Application of the Molecular Analysis of the T-Cell Receptor Repertoire in the Study of Immune-Mediated Hematologic Diseases", *Hematology*, 8(3): 173-181 (2003).
Pohl, G. and Shih. "Principle and applications of digital PCR", *Expert Rev. Mol. Diagn.*, 4(1):41-47 (2004).
Pop and Salzberg. "Bioinformatics challenges of new sequencing technology", *NIH, Trends Genet.*, 24(3): 142-149 (2008).
Pourmand, et al. "Direct electrical detection of DNA synthesis", *PNAS*, 103(17): 6466-6470 (2006). Epub Apr. 13, 2006.
Polz and Cavanaugh. "Bias in Template-to-Product Ratios in Multitemplate PCR", *Applied and Environmental Microbiology*, 64(10): 3724-3730 (1998).
Porter, et al. "Chimeric antigen receptor-modified T cells in chronic lymphoid leukemia", *N Engl J Med.*, 365(8):725-33 (2011). doi: 10.1056/NEJMoa1103849. Epub Aug. 10, 2011.
Prabakaran et al. "454 antibody sequencing—error characterization and correction", *BMC Research Notes*, 4: 404 (2011).

(56) References Cited

OTHER PUBLICATIONS

Puisieux, I. et al., "Oligoclonality of Tumor-Infiltrating Lymphocytes from Human Melanomas," The Journal of Immunology, 153:2807-2818 (1994).
Putnam, et al. "Clinical grade manufacturing of human alloantigen-reactive regulatory T cells for use in transplantation", Am J Transplant., 13(11): 3010-3020 (2013). doi: 10.1111/ajt.12433. EpubSep. 18, 2013.
Qiu et al. "DNA sequence-based "bar codes" for tracking the origins of expressed sequence tags from a maize cDNA library constructed using multiple mRNA sources", *Plant Physiology*, 133(2): 475-481 (2003).
Ramesh, et al. "Clonal and constricted T cell repertoire in Common Variable Immune Deficiency", Clin Immunol., pii: S1521-6616(15)00004-2 (2015). doi: 10.1016/j.clim.2015.01.002. [Epub ahead of print].
Ramsden, et al. "V(D)J recombination: Born to be wild", *Semin Cancer Biol.*, 20(4): 254-260 (2010). doi: 10.1016/j.semcancer.2010.06.002. Epub Jul. 1, 2010.
Rasmussen, T. et al. "Quantitation of minimal residual disease in multiple myeloma using an allele-specific real-time PCR assay", *Experimental Hematology*, 28:1039-1045 (2000).
Ray, et al. "Single cell multiplex PCR amplification of five dystrophin gene exons combined with gender determination", *Molecular Human Reproduction*, 7(5): 489-494 (2001).
Reddy, et al. "Monoclonal antibodies isolated without screening by analyzing the variable-gene repertoire of plasma cells", *Nature Biotechnology*, 28(9): 965-969 (2010). doi: 10.1038/nbt.1673. Epub Aug. 29, 2010.
Reddy and Georgiou. "Systems analysis of adaptive immunity by utilization of high-throughput technologies", *Current Opinion in Biotechnology*, 22(4): 584-589 (2011).
Reinartz et al. "Massively parallel signature sequencing (MPSS) as a tool for in-depth quantitative gene expression profiling in all organisms", *Brief Funct Genomic Proteomic.*, 1(1):95-104 (2002).
Reischl and Kochanowski. "Quantitative PCR. A Survey of the Present Technology", *Molecular Biotechnology*, 3:55-71 (1995).
Ria, et al. "Collagen-specific T-cell repertoire in blood and synovial fluid varies with disease activity in early rheumatoid arthritis", *Arthritis Res Ther.*, 10(6):R135, 18 pages (2008). Epub Nov. 17, 2008.
Rickinson and Moss. "Human cytotoxic T lymphocyte responses to Epstein-Barr virus infection", *Annu Rev Immunol.*, 15:405-431 (1997).
Rieder, et al. "A normalization procedure for removal of residual multiplex PCR amplification bias from ultra-deep sequencing of the TCR repertoire", (Program #530W). Presented at the 62nd Annual Meeting of the American Society of Human Genetics, Nov. 7, 2012 in San Francisco, California. 2 pages.
Rieder, et al. "A normalization procedure for removal of residual multiplex PCR amplification bias from ultra-deep sequencing of the TCR repertoire", Presented at the Annual Meeting of the American Society of Hematology 2012 in Atlanta, Georgia Dec. 8-11, 2012. Poster. 1 page.
Risitano et al. "In-vivo dominant immune responses in aplastic anaemia: molecular tracking of putatively pathogenetic T-cell clones by TCRβ-CDR3 sequencing", *Lancet*, 364:355-364 (2004).
Robert, et al. "CTLA4 blockade broadens the peripheral T-cell receptor repertoire", Clin Cancer Res., 20(9):2424-32 (2014). doi: 10.1158/1078-0432.CCR-13-2648. Epub Feb. 28, 2014.
Robins, H. et al. "Ultra-sensitive detection of rare T cell clones", *Journal of Immunological Methods*, 375(1-2): 14-19 (2012). Epub Sep. 10, 2011.
Robins, et al. "CD4+ and CD8+ T cell β antigen receptors have different and predictable V and J gene usage and CDR3 lengths", *J. Immunol.*, 188: 115.10, Abstract (2012).
Robins et al. "Detecting and monitoring lymphoma with high-throughput sequencing" Oncotarget, 2:287-288 (2011).
Robins, H. et al. "Digital Genomic Quantification of Tumor Infiltrating Lymphocytes", *Science Translational Medicine*, 5:214ra169, 19 pages, Supplementary Materials (2013).
Robins, H. et al. "Comprehensive assessment of T-cell receptor β-chain diversity in αβ T cells", *Blood*, 114(19):4099-4107 (and Supplemental Materials) (2009).
Robins, et al. "Effects of aging on the human adaptive immune system revealed by high-throughput DNA sequencing of T cell receptors", *J Immunol.*, 188: 47.16, Abstract (2012).
Robins, et al. "High-throughput sequencing of T-cell receptors." Sep. 2010. Poster. 1 page.
Robins, et al. "Immune profiling with high-throughput sequencing." Presented for the ASHI 2011 conference. Oct. 2011. Poster. 1 page.
Robins, et al. "Immunosequencing: applications of immune repertoire deep sequencing", *Curr Opin Immunol.*, 25(5): 646-652 (2013). doi: 10.1016/j.coi.2013.09.017. Epub Oct. 16, 2013.
Robins, H. et al. "Overlap and Effective Size of the Human CD8+ T Cell Receptor Repertoire", *Science Transitional Medicine*, 2(47, 47ra64):17 pages, Supplementary Materials (2010).
Robins, et al. "Overlap of the human CD8+ T cell receptor repertoire." Oct. 2010. Poster. 1 page.
Robins. "Overlap and effective size of the human CD8+ T cell repertoire", Keystone Symposia held Oct. 27, 2010 to Nov. 1, 2010. Immunological Mechanisms of Vaccination (Abstract). Available online Sep. 27, 2010, 1 page.
Robins, H. et al. "The Computational Detection of Functional Nucleotide Sequence Motifs in the Coding Regions of Organisms", *Exp Biol Med*, 233(6): 665-673 (2008).
Ronaghi, et al. "A sequencing method based on real-time pyrophosphate", *Science*, 281(5375): 363, 365, 5 pages (1998).
Rosenberg, S.A. et al. "New Approach to the Adoptive Immunotherapy of Cancer with Tumor-Infiltrating Lymphocytes", *Science*, 233(4770): 1318-1321 (1986).
Rosenquist, et al. "Clonal evolution as judged by immunoglobulin heavy chain gene rearrangements in relapsing precursor-B acute lymphoblastic leukemia", *Eur J Haematol.*, 63(3):171-179 (1999).
Rothberg, et al. "An integrated semiconductor device enabling non-optical genome sequencing", *Nature*, 475(7356): 348-352 (2011). doi: 10.1038/nature10242.
Rougemont, et al. "Probabilistic base calling of Solexa sequencing data", *BMC Bioinformatics*, 9:431, 12 pages (2008).
Ryan et al. "Clonal evolution of lymphoblastoid cell lines", *Laboratory Investigation*, 86(11):1193-1200 (2006). Epub Oct. 2, 2006.
Saada, R. et al. "Models for antigen receptor gene rearrangement: CDR3 length", *Immunology and Cell Biology*, 85:323-332 (2007).
Salzberg. "Mind the gaps", *Nature Methods*, 7(2): 105-106 (2010).
Sanchez-Freire et al. "Microfluidic single-cell real-time PCR for comparative analysis of gene expression patterns", *Nature Protocols*, 7(5): 829-838 (2012).
Sandberg et al. "BIOMED-2 Multiplex Immunoglobulin/T-Cell Receptor Polymerase Chain Reaction Protocols Can Reliably Replace Southern Blot Analysis in Routine Clonality Diagnostics", *J. Molecular Diagnostics*, 7(4): 495-503 (2005).
Sandberg, et al. "Capturing whole-genome characteristics in short sequences using a naïve Bayesian classifier", *Genome Res.*, 11(8): 1404-9 (2001).
Santamaria, P. et al. "Beta-Cell-Cytotoxic CD8 T Cells from Nonobese Diabetic Mice Use Highly Homologous T Cell Receptor a-Chain CDR3 Sequences", *The Journal of Immunology*, 154(5):2494-2503 (1995).
Sato et al. "Intraepithelial CD8+ tumor-infiltrating lymphocytes and a high CD8+/regulatory T cell ratio are associated with favorable prognosis in ovarian cancer", *PNAS*, 102(51): 18538-18543 (2005). Epub Dec. 12, 2005.
Satoh et al. "Pretreatment with restriction enzyme or bovine serum albumin for effective PCR amplification of Epstein-Barr virus DNA in DNA extracted from paraffin-embedded gastric carcinoma tissue", *J Clin Microbiol.*, 36(11): 3423-3425 (1998).
Schaufelberger et al. "An uneven expression of T cell receptor V genes in the arterial wall and peripheral blood in giant cell arteritis", *Inflammation*, 31(6):372-383 (2008).

(56) References Cited

OTHER PUBLICATIONS

Schlissel, M.S. et al. "Leukemia and lymphoma: a cost of doing business for adaptive immunity", *Genes Dev.*, 20(12): 1539-1544 (2006).

Schloss, PD et al. Reducing the Effects of PCR Amplification and Sequencing Artifacts on 16S Rrna-Based Studies. PLoS One. Dec. 14, 2011, vol. 6, No. 12; e27310; DOI:10.1371/journal.pone.0027310.

Schmitt et al. "Detection of ultra-rare mutations by next-generation sequencing," *PNAS*, 109(36): 14508-14513 and Supporting Information, 9 pages (2012).

Schøller et al. "Analysis of T cell receptor αβ variability in lymphocytes infiltrating melanoma primary tumours and metastatic lesions", *Cancer Immunol Immunother.* 39(4):239-248 (1994).

Schrappe, M. et al. "Late MRD response determines relapse risk overall and in subsets of childhood T-cell ALL: results of the AIEOP-BFM-ALL 2000 study", *Blood*, 118(8): 2077-2084 (2011).

Schreiber et al. "Cancer immunoediting: integrating immunity's roles in cancer suppression and promotion", *Science*, 331(6024): 1565-1570 (2011). doi: 10.1126/science.1203486.

Schwab et al. "CD8+ T-cell clones dominate brain infiltrates in Rasmussen encephalitis and persist in the periphery", *Brain*, 132:1236-1246 (2009).

Schwartzman, Armin. "Empirical null and false discovery rate inference for exponential families." The Annals of Applied Statistics (2008); 2(4): 1332-1359.

Schweiger et al. "Genome-wide massively parallel sequencing of formaldehyde fixed-paraffin embedded (FFPE) tumor tissues for copy-number- and mutation-analysis", *PLoS One*, 4(5): e5548, 7 pages (2009). doi: 10.1371/journal.pone.0005548. Epub May 14, 2009.

Chinese Patent Application No. 201510054401.X, Search Report dated Jul. 14, 2016, 2 pages.

Sebastian, E. et al., "Molecular Characterization of immunoglobulin gene rearrangements in diffuse large B-cell lymphoma", *Am. J. Pathol.*, 181: 1879-1888, Abstract (2012). (Epub: Sep. 28, 2012).

Sehouli et al. "Epigenetic quantification of tumor-infiltrating T-lymphocytes" *Epigenetics*, 6(2): 236-246 (2011). Epub Feb. 1, 2011.

Seitz, et al. "Reconstitution of paired T cell receptor α- and β-chains from microdissected single cells of human inflammatory tissues", *PNAS*, 103: 12057-12062 (2006).

Seo, et al. "Four-color DNA sequencing by synthesis on a chip using photocleavable fluorescent nucleotides", *PNAS*, 102(17): 5926-5931 (2005). Epub Apr. 13, 2005.

Sfanos et al. "Human Prostate-Infiltrating CD8+ T Lymphocytes are Oligoclonal and PD-1+", *The Prostate*, 69(15): 1694-1703 (2009).

Sfanos et al. "Phenotypic analysis of prostate-infiltrating lymphocytes reveals TH17 and Treg skewing", *Clinical Cancer Research*, 14(11):3254-3261 (2008). doi: 10.1158/1078-0432.CCR-07-5164.

Shen et al. "Comparing platforms for *C. elegans* mutant identification using high-throughput whole-genome sequencing", *PLoS One*, 3(12):e4012, 6 pages (2008).

Shendure, et al. "Advanced sequencing technologies: methods and goals", *Nat Rev Genet.*, 5(5): 335-344 (2004).

Shendure and Ji. "Next-generation DNA sequencing", *Nature Biotechnology*, 26(10):1135-1145 (2008).

Sherwood, A. et al. "Deep Sequencing of the Human TCRγ and TCRβ Repertoires Suggests that TCR β Rearranges After αβ and γδ T Cell Commitment", Science Translational Medicine, *Sci. Transl. Med.*, 3(90): 1-7 (2011).

Sherwood, et al. "New Technologies for Measurements of Tumor Infiltrating Lymphocytes", Presented Nov. 7, 2012 Moscone Center, Exhibit Halls ABC.

Sherwood, et al. "Tumor-infiltrating lymphocytes in colorectal tumors display a diversity of T cell receptor sequences that differ from the T cells in adjacent mucosal tissue", Cancer Immunol Immunother., 62(9):1453-61 (2013). doi: 10.1007/s00262-013-1446-2. Epub Jun. 16, 2013.

Shino, et al. "Usefulness of immune monitoring in lung transplantation using adenosine triphosphate production in activated lymphocytes", *The Journal of Heart and Lung Transplant*, 31: 996-1002 (2012).

Shiroguchi et al. "Digital RNA sequencing minimizes sequence-dependent bias and amplification noise with optimized single-molecule barcodes", *PNAS*, 109(4): 1347-1352 (2012).

Shoemaker et al. "Quantitative phenotypic analysis of yeast deletion mutants using a highly parallel molecular bar-coding strategy," *Nature Genetics*, 14(4): 450-456 (1996).

Shumaker, et al. "Mutation detection by solid phase primer extension", *Hum Mutat.*, 7(4): 346-354, Abstract Only (1996).

Sia, et al. "Microfluidic devices fabricated in poly(dimethylsiloxane) for biological studies", *Electrophoresis*, 24(21): 3563-3576, Abstract Only (2003).

Sims, et al. "Fluorogenic DNA sequencing in PDMS microreactors", *Nat Methods*, 8(7): 575-580 (2011). doi: 10.1038/nmeth.1629.

Sims, et al. "MHC-peptide tetramers for the analysis of antigen-specific T cells", *Expert Rev Vaccines*, 9(7): 765-774 (2010). doi: 10.1586/erv.10.66.

Sing et al. "A molecular comparison of T Lymphocyte populations infiltrating the liver and circulating in the blood of patients with chronic hepatitis B: evidence for antigen-driven selection of a public complementarity-determining region 3 (CDR3) motif", *Hepatology*, 33(5):1288-1298 (2001).

Singapore Application No. 11201407888R, Written Opinion dated Aug. 14, 2015, 12 pages.

Singapore Application No. 11201500313Y, Search Report and Written Opinion dated Dec. 9, 2015, 11 pages.

Sint, D., et al. "Advances in multiplex PCR: balancing primer efficiencies and improving detection success", *Methods in Ecology and Evolution*, 3(5): 898-905 (2012).

Skulina et al. "Multiple Sclerosis: Brain-infiltrating CD8+ T cells persist as clonal expansions in the cerebrospinal fluid and blood", *PNAS*, 101(8):2428-2433 (2004).

Smith, et al. "Comparison of biosequences", *Advances in Applied Mathematics*, 2: 482-489 (1981).

Smith et al. "Rapid generation of fully human monoclonal antibodies specific to a vaccinating antigen", *Nature Protocols*, 4(3): 372-384 and CORRIGENDA (2009).

Smith et al. "Rapid whole-genome mutational profiling using next-generation sequencing technologies", *Genome Research*, 18: 1638-1642 (2008).

Sobrino, et al. "SNPs in forensic genetics: a review on SNP typing methodologies", *Forensic Sci Int.*, 154(2-3): 181-194, Abstract Only (2005). Epub Jan. 11, 2005.

Spreafico, et al. "A circulating reservoir of pathogenic-like CD4+ T cells shares a genetic and phenotypic signature with the inflamed synovial micro-environment", *Ann Rheum Dis.*, 0: 1-7 (2014). doi: 10.1136/annrheumdis-2014-206226. [Epub ahead of print].

Sramkova, et al. "Detectable minimal residual disease before allogeneic hematopoietic stem cell transplantation predicts extremely poor prognosis in children with acute lymphoblastic leukemia", *Pediatr. Blood Cancer*, 48(1):93-100 (2007).

Srinivasan et al. "Effect of fixatives and tissue processing on the content and integrity of nucleic acids", *Am J Pathol.*, 161(6): 1961-1971 (2002).

Srivastava and Robins. "Palindromic nucleotide analysis in human T cell receptor rearrangements", PLoS One, 7(12):e52250 (2012). doi: 10.1371/journal.pone.0052250. Epub Dec. 21, 2012.

Steenbergen, et al. "Distinct ongoing Ig heavy chain rearrangement processes in childhood B-precursor acute lymphoblastic leukemia", *Blood*, 82(2):581-589 (1993).

Steenbergen, et al. "Frequent ongoing T-cell receptor rearrangements in childhood B-precursor acute lymphoblastic leukemia: implications for monitoring minimal residual disease", *Blood*, 86(2): 692-702, Abstract Only (1995).

Stemmer, et al. "Single-step assembly of a gene and entire plasmid from large numbers of oligodeoxyribonucleotides", *Gene*, 164(1): 49-53 (1995).

Steward et al. "A polymerase chain reaction study of the stability of Ig heavy-chain and T-cell receptor delta gene rearrangements between

(56) References Cited

OTHER PUBLICATIONS presentation and relapse of childhood B-lineage acute lymphoblastic leukemia", *Blood*, 83(5):1355-1362 (1994).

Stewart and Schwartz. "Immunoglobulin V regions and the B cell", *Blood*, 83(7): 1717-1730 (1994).

Stickler, et al. "An in vitro human cell-based assay to rank the relative immunogenicity of proteins", *Toxicol Sci.*, 77(2): 280-289 (2004). Epub Dec. 22, 2003.

Stiller et al. "Direct multiplex sequencing (DMPS)—a novel method for targeted high-throughput sequencing of ancient and highly degraded DNA", *Genome Research*, 19: 1843-849 (2009).

Straten, Per thor, et al. "T-cell clonotypes in cancer", *Journal of Translational Medicine*, 2(1): 11, 10 pages (2004).

Stratton. "Exploring the genomes of cancer cells: progress and promise", *Science*, 331(6024): 1553-1558 (2011). doi: 10.1126/science.1204040.

Striebich, et al. "Selective Accumulation of Related CD41 T Cell Clones in the Synovial Fluid of Patients with Rheumatoid Arthritis", *J Immunol.*, 161(8): 4428-4436 (1998).

Struyk et al. "T cell receptors in rheumatoid arthritis", *Arthritis & Rheumatism*, 38(5):577-589 (1995).

Sumida et al. "T cell receptor repertoire of infiltrating T cells in lips of Sjögren's syndrome patients", *J Clin Invest.*, 89:681-685 (1992).

Sumida et al. "T cell receptor Vα repertoire of infiltrating T cells in labial salivary glands from patients with Sjögren's syndrome", *J Rheumatol.*, 21:1655-1661 (1994).

Swarup and Rajeswari. "Circulating (cell-free) nucleic acids—a promising, non-invasive tool for early detection of several human diseases", *FEBS Letters*, 581(5): 795-799 (2007). Epub Feb. 2, 2007.

Szczepanski et al. "Comparative analysis of Ig and TCR gene rearrangements at diagnosis and at relapse of childhood precursor-B-ALL provides improved strategies for selection of stable PCR targets for monitoring of minimal residual disease", *Blood*, 99(7):2315-2323 (2002).

Szczepanski, T. et al. "Minimal residual disease in leukemia patients", *Lancet Oncology*, 2:409-417 (2001).

Szczepanski et al. "Why and how to quantify minimal residual disease in acute lymphoblastic leukemia?", *Leukemia*, 21(4):622-626 (2007). Epub Feb. 15, 2007.

Tackenberg et al. "Clonal expansions of CD4+ β helper T cells in autoimmune myasthenia gravis", *European Journal of Immunology*, 37(3):849-863 (2007).

Tajiri et al. "Cell-microarray analysis of antigen-specific B-cells: single cell analysis of antigen receptor expression and specificity", *Cytometry Part A*, 71A: 961-967 (2007).

Takamatsu, et al., "A comparison between next-generation sequencing and ASO-qPCR for minimal residual disease detection in multiple myeloma", *J. Clin. Oncol.*, 31(Supplement 1): Abstract 8601 (Conference Abstract), Entire Abstract (2013).

Tam, James P. "Synthetic peptide vaccine design: synthesis and properties of a high-density multiple antigenic peptide system." Proceedings of the National Academy of Sciences (1988); 85.15: 5409-5413.

Tanaka et al. "Single-Cell Analysis of T-Cell Receptor Repertoire of HTLV-1 Tax-Specific Cytotoxic T Cells in Allogeneic Transplant Recipients with Adult T-Cell Leukemia/Lymphoma", *Cancer Research*, 70: 6181-6192 (2010).

Taubenheim et al. "High Rate of Antibody Secretion Is not Integral to Plasma Cell Differentiation as Revealed by XBP-1 Deficiency", *The Journal of Immunology*, 189: 3328-3338 (2012).

Tautz, et al. "Cryptic simplicity in DNA is a major source of genetic variation", *Nature*, 322(6080): 652-656 (1986).

Tawfik, et al. "Man-made cell-like compartments for molecular evolution", *Nat Biotechnol.*, 16(7): 652-656, Abstract Only (1998).

Ten Bosch et al. "Keeping Up With the Next Generation Massively Parallel Sequencing in Clinical Diagnostics", *Journal of Molecular Diagnostics*, 10(6): 484-492 (2008).

Tewhey, R. et al. "Corrigendum: Microdroplet-based PCR enrichment for large-scale targeted sequencing", *Nature Biotechnology*, 28(2):178, 1 page (2010).

Thiel, et al. "Antigen-specific cytometry—new tools arrived!", *Clin Immunol.*, 111(2): 155-161, Abstract Only (2004).

Thornhill et al. "A comparison of different lysis buffers to assess allele dropout from single cells for preimplantation genetic diagnosis", *Prenatal Diagnosis*, 21:490-497 (2001).

Tokimitsu et al. "Single lymphocyte analysis with a microwell array chip", *Cytometry Part A*, 71A:1003-1010 (2007).

Toriello et al. "Integrated microfluidic bioprocessor for single-cell gene expression analysis", *PNAS*, 105(51): 20173-20178 (2008).

Triebel, F. et al. "A Unique V-J-C-Rearranged Gene Encodes A γ Protein Expressed on the Majority of CD3+ T Cell Receptor -a/fr Circulating Lymphocytes", *J. Exp. Med.*, 167:694-699 (1988).

Tsai et al. "Discovery of rare mutations in populations: TILLING by sequencing", Plant Physiology, 156(3): 1257-1268 (and Supplemental Data) (2011).

Tsankova, et al. "Peripheral T-cell lymphoma emerging in a patient with aggressive polymyositis: molecular evidence for neoplastic transformation of an oligo clonal T-cell infiltrate", Acta Neuropathol., 126(4):595-601 (2013). doi: 10.1007/s00401-013-1164-z. Epub Aug. 13, 2013.

Tschumper, et al. "Comprehensive assessment of potential multiple myeloma immunoglobulin heavy chain V-D-J intraclonal variation using massively parallel pyrosequencing", *Oncotarget*, 3(4): 502-513 (2012).

Turcotte and Rosenberg. "Immunotherapy for metastatic solid cancers", *Adv Surg.*, 45: 341-360 (2011).

UK combined search and examination report dated Mar. 20, 2013 for GB 1300533.5.

UK Combined Search Report and Office action dated Jun. 29, 2012 for UK application No. GB1209668.1.

UK Combined Search Report and Office action dated May 27, 2011 for UK application No. GB1105068.9.

UK Search Report and office action dated Jan. 13, 2012 for UK application No. GB1120209.0.

UK Search Report and office action dated Jul. 7, 2010 for UK application No. GB1009641.0.

Umibe et al. "Clonal expansion of T cells infiltrating in the airways of non-atopic asthmatics", *Clinical & Experimental Immunology*, 119(3):390-397 (2000).

Unrau and Deugau. "Non-cloning amplification of specific DNA fragments from whole genomic DNA digests using DNA 'indexers'", *Gene.*, 145(2): 163-169, Abstract Only, 2 pages (1994).

Uppaluri et al. "Focus on TILs: prognostic significance of tumor infiltrating lymphocytes in head and neck cancers", *Cancer Immunity*, 8:16, 10 pages (2008).

Urban, et al. "A systematic and quantitative analysis of PCR template contamination", *J Forensic Sci.*, 45(6): 1307-1311 (2000).

Van Der Velden, V.H.J., et al. "Analysis of minimal residual disease by Ig/TCR gene rearrangements: guidelines for interpretation of real-time quantitative PCR data," *Leukemia*, 21:604-611 (2007).

Van Der Velden, V.H.J., et al. "Detection of minimal residual disease in hematologic malignancies by realtime quantitative PCR: principles, approaches, and laboratory aspects," *Leukemia*, 17:1013-1034 (2003).

Van Der Velden, V.H.J., et al. "Real-time quantitative PCR for detection of minimal residual disease before allogeneic stem cell transplantation predicts outcome in children with acute lymphoblastic leukemia", *Leukemia*, 15:1485-1487 (2001).

Van Dongen, J.J.M. et al. "Design and standardization of PCR primers and protocols for detection of clonal immunoglobulin and 1-cell receptor gene recombinations in suspect lymphoproliferations: Report of the BIOMED-2 Concerted Action BMHC-CT98-3936", *Leukemia*, 17:2257-2317 (2003).

Van Dongen, J.J.M. et al. "Prognostic value of minimal residual disease in acute lymphoblastic leukaemia in childhood", *The Lancet*, 352:1731-1738 (1998).

Van Heijst, J.W.J., et al., "Quantitative assessment of T-cell repertoire recovery after hematopoietic stem cell transplantation." Nat Med. (2013); 19(3): 372-377.

(56) References Cited

OTHER PUBLICATIONS

Varley and Mitra. "Nested patch PCR enables highly multiplexed mutation discovery in candidate genes", Genome Research, 18: 1844-1850 (2008).
Venturi, et al. "A mechanism for TCR sharing between T cell subsets and individuals revealed by pyrosequencing", J Immunol., 186(7): 4285-4294 (2011). doi: 10.4049/jimmunol.1003898. Epub Mar. 7, 2011.
Venturi, V. et al. "TCR β-Chain Sharing in Human CD8[+]T Cell Responses to Cytomegalovirus and EBV[1]", The Journal of Immunology, 181:7853-7862 (2008).
Vester, et al. "LNA (locked nucleic acid): high-affinity targeting of complementary RNA and DNA", Biochemistry, 43(42): 13233-13241, Abstract Only (2004).
Vlassov, et al. "Circulating nucleic acids as a potential source for cancer biomarkers", Curr Mol Med., 10(2): 142-165 (2010).
Vogelstein et al. "Cancer genome landscapes", Science, 339(6127): 1546-1558 (2013). doi: 10.1126/science.1235122.
Wälchli, et al. "A practical approach to T-cell receptor cloning and expression", PLoS One, 6(11): e27930, 11 pages (2011). doi: 10.1371/journal.pone.0027930. Epub Nov. 21, 2011.
Wang, et al. "Balanced-PCR amplification allows unbiased identification of genomic copy changes in minute cell and tissue samples", Nucleic Acids Research, 32(9): e76, 10 pages (2004).
Wang, et al. "High throughput sequencing reveals a complex pattern of dynamic interrelationships among human T cell subsets", PNAS, 107(4): 1518-1528 (2010).
Wang et al. "Immunorepertoire analysis by multiplex PCR amplification and high throughput sequencing", Poster-Program 42.6, The 96th Annual Meeting of the America Association of Immunologists, Seattle, USA, May 8-12, 2009, 1 page.
Wang, X. et al. "Quantitative Measurement of Pathogen Specific Human Memory T Cell Repertoire Diversity using a CDR3 B-Specific Microarray", BMC Genomics, 8(329): 1-13 (2007).
Warren et al. "Exhaustive T-cell repertoire sequencing of human peripheral blood samples reveals signatures of antigen selection and a directly measured repertoire size of at least 1 million clonotypes", Genome Res., 21(5): 790-797 (2011). Epub Feb. 24, 2011.
Warren et al. "Profiling model T-cell metagenomes with short reads", Bioinformatics, 25(4):458-464 (2009).
Weiss et al. "Clonal Rearrangements of T-Cell Receptor Genes in Mycosis Fungoides and Dermatopathic Lymphadenopathy", The New England Journal of Medicine, 313(9):539-544 (1985).
Welch and Link. "Genomics of AML: clinical applications of next-generation sequencing", American Society of Hematology, 2011: 30-35 (2011). doi: 10.1182/asheducation—Jan. 30, 2011.
Wells, et al. "Rapid evolution of peptide and protein binding properties in vitro", Curr Opin Biotechnol., 3(4): 355-362, Abstract Only (1992).
Wells, et al. "Strategies for preimplantation genetic diagnosis of single gene disorders by DNA amplification", Prenatal Diagnosis, 18(13):1389-1401 (1998).
Weng, et al. "Minimal residual disease monitoring with high-throughput sequencing of T cell receptors in cutaneous T cell lymphoma", Sci Transl Med., 5(214):214ra171 (2013).
Westermann and Pabst. "Distribution of lymphocyte subsets and natural killer cells in the human body", Clin Investig., 70(7): 539-544 (1992).
Wetmur and Chen. "An emulsion polymerase chain reaction-based method for molecular haplotyping", Methods in Molecular Biology, 410: 351-361 (1996).
Wetmur and Chen. "Linking emulsion PCR haplotype analysis", chapter 11, Park, D.J. (ed.), PCR Protocols, Methods in Molecular Biology, 687: 165-175 (2011).
Wetmur et al. "Molecular haplotyping by linking emulsion PCR: analysis of paraoxonase 1 haplotypes and phenotypes", Nucleic Acids Research, 33(8):2615-2619 (2005).
Weusten, et al. "Principles of quantitation of viral loads using nucleic acid sequence-based amplification in combination with homogeneous detection using molecular beacons", Nucleic Acids Res., 30(6): e26, 7 pages (2002).
White et al. "High-throughput microfluidic single-cell RT-qPCR", PNAS, 108(34): 13999-14004 (2011).
Whiteford, et al. "Swift: primary data analysis for the Illumina Solexa sequencing platform", Bioinformatics, 25(17): 2194-2199 (2009). doi: 10.1093/bioinformatics/btp383. Epub Jun. 23, 2009.
Wilson-Lingardo et al., "Deconvolution of Combinatorial Libraries for Drug Discovery: Experimental Comparison of Pooling Strategies." J. Med. Chem., (1996); 39 (14): 2720-2726.
Wlodarski et al. "Molecular strategies for detection and quantitation of clonal cytotoxic T-cell responses in aplastic anemia and myelodysplastic syndrome", Blood, 108(8):2632-2641 (2006).
Wlodarski et al. "Pathologic clonal cytotoxic T-cell responses: nonrandom nature of the T-cell-receptor restriction in large granular lymphocyte leukemia", Blood, 106:2769-2779 (2005).
Wolfl, et al. "Activation-induced expression of CD137 permits detection, isolation, and expansion of the full repertoire of CD8+T cells responding to antigen without requiring knowledge of epitope specificities", Blood, 110(1): 201-210 (2007). Epub Mar. 19, 2007.
Wolfl, et al. "Use of CD137 to study the full repertoire of CD8+ T cells without the need to know epitope specificities", Cytometry A., 73(11): 1043-1049 (2008). doi: 10.1002/cyto.a.20594.
Wood, et al. "Using next-generation sequencing for high resolution multiplex analysis of copy number variation from nanogram quantities of DNA from formalin-fixed paraffin-embedded specimens", Nucleic Acids Research, 38(14): e151, 11 pages (2010). doi: 10.1093/nar/gkq510. Epub Jun. 4, 2010.
Woodsworth, Daniel J., et al., "Sequence analysis of T-cell repertoires in health and disease." Genome Medicine (2013); 5: 98, 13 pages.
Wrammert et al. "Rapid cloning of high-affinity human monoclonal antibodies against influenza virus", Nature, 453: 667-672 (2008).
Wu, et al. "High-throughput sequencing detects minimal residual disease in acute T lymphoblastic leukemia", Sci Transl Med., 4(134):134ra63 (2012). doi: 10.1126/scitranslmed.3003656.
Wu, et al. "High-throughput sequencing of T-cell receptor gene loci for minimal residual disease monitoring in T Lymphoblastic Leukemia", Blood, 118: 2545 (Abstr) (2011).
Wu, Y-C. et al. "High-throughput immunoglobulin repertoire analysis distinguishes between human IgM memory and switched memory B-cell populations", Blood Journal, 116(7): 1070-1078, 22 pages (2010).
Wu et al. "Focused Evolution of HIV-1 Neutralizing Antibodies Revealed by Structures and Deep Sequencing", Science, 333: 1593-1602 (2011).
Wu, H.D. et al. "The Lymphocytic Infiltration in Calcific Aortic Stenosis Predominantly Consists of Clonally Expanded T Cells", The Journal of Immunology, 178(8): 5329-5339 (2007).
Xie, Yang, et al., "A note on using permutation-based false discovery rate estimates to compare different analysis methods for microarray data." Bioinformatics (2005); 21.23: 4280-4288.
Xiong, et al. "Non-polymerase-cycling-assembly-based chemical gene synthesis: strategies, methods, and progress", Biotechnol Adv., 26(2): 121-134, Abstract Only (2008). Epub Nov. 7, 2007.
Xu, W. et al. "A Novel Universal Primer-Multiplex-PCR Method with Sequencing Gel Electrophoresis Analysis", PLoS One, 7(1): e22900, 10 pages (2012).
Xu, et al. "Simultaneous isolation of DNA and RNA from the same cell population obtained by laser capture microdissection for genome and transcriptome profiling", J Mol Diagn., 10(2):129-134 (2008). doi: 10.2353/jmoldx.2008.070131. Epub Feb. 7, 2008.
Yao, et al. "Analysis of the CDR3 length repertoire and the diversity of TCRα chain in human peripheral blood T Lymphocytes", Cell Mol Immunol., 4(3): 215-220 (2007).
Yeh, et al. "Regulating DNA translocation through functionalized soft nanopores", Nanoscale, 4(8): 2685-4693, Abstract Only (2012). doi: 10.1039/c2nr30102d. Epub Mar. 15, 2012.
Yassai, M.B. et al. "A clonotype nomenclature for T cell receptors", Immunogenetics, 61:493-502 (2009).

(56) References Cited

OTHER PUBLICATIONS

Yin et al. "Antiretroviral therapy restores diversity in the T-cell receptor Vβ repertoire of CD4 T-cell subpopulations among human immunodeficiency virus type 1-infected children and adolescents", *Clinical and Vaccine Immunology*, 16(9):1293-1301 (2009).

Yon and Fried. "Precise gene fusion by PCR", *Nucleic Acids Research*, 17(12):4895, 1 pages (1989).

York, et al. "Highly parallel oligonucleotide purification and functionalization using reversible chemistry", *Nucleic Acids Res.*, 40(1): e4, 7 pages (2012). doi: 10.1093/nar/gkr910. Epub Oct. 29, 2011.

Yu and Fu. "Tumor-infiltrating T lymphocytes: friends or foes?", *Lab Invest.*, 86(3): 231-245 (2006).

Zagnoni, et al. "Droplet Microfluidics for High-throughput Analysis of Cells and Particles", *Methods in Cell Biology*, Chapter 2, 102: 23-48 (2011).

Zaliova, et al. "Quantification of fusion transcript reveals a subgroup with distinct biological properties and predicts relapse in BCR/ABL-positive ALL: implications for residual disease monitoring", *Leukemia*,23(5):944-951 (2009).

Zehentner et al. "Minimal Disease Detection and Confirmation in Hematologic Malignancies: Combining Cell Sorting with Clonality Profiling", *Clinical Chemistry*, 52(3): 430-437 (2006).

Zeng et al. "High-performance single cell genetic analysis using microfluidic emulsion generator arrays", *Anal. Chem.*, 82(8):3183-3190 (2010).

Zhong, Q. et al. "Multiplex digital PCR: breaking the one target per color barrier of quantitative PCR", Lab Chip, 11:2167-2174 (2011).

Zhou et al. "High throughput analysis of TCR-β rearrangement and gene expression in single cells", *Laboratory Investigation*, 86: 314-321 (2006).

Zhou et al. "Isolation of purified and live Foxp3+ regulatory T cells using FACS sorting on scatter plot", *J Mol Cell Biol.*, 2(3): 164-169 (2010). doi: 10.1093/jmcb/mjq007. Epub Apr. 29, 2010.

Zimmerman and Mannhalter. "Technical aspects of quantitative competitive PCR", *Biotechniques*, 21: 268-279 (1996).

- 640 healthy subjects
  - Bone marrow donors at FHCRC
  - Mostly healthy
- CMV serotype determined (routine for BM donors)
  - 287 CMV+, 353 CMV-
- HLA typing performed (routine for BM donors)
- Sequenced ~ 250k TCRs from peripheral blood

FIG. 3B

| Sex | CMV+ | CMV- | All |
|---|---|---|---|
| Female | 150 | 147 | 297 |
| Male | 137 | 206 | 343 |
| All | 287 | 353 | 640 |
| Race/ethnicity* | CMV+ | CMV- | All |
| White | 164 | 212 | 376 |
| Black or African American | 8 | 0 | 8 |
| Asian | 15 | 2 | 17 |
| American Indian or Alaska Native | 7 | 2 | 9 |
| Native Hawaiian or other Pacific Islander | 3 | 0 | 3 |
| Hispanic or Latino | 20 | 6 | 26 |
| Unknown | 70 | 131 | 201 |
| All | 287 | 353 | 640 |
| Age (in years) | CMV+ | CMV- | All |
| Mean | 42 | 37 | 40 |
| Median | 44 | 38 | 41 |
| Range | 5-74 | 1-70 | 1-74 |
| # of individuals of unknown age | 31 | 56 | 87 |

*Race and Ethnicity categories as defined by the NIH were used. All Hispanic/Latino individuals were classified as Race=Unknown but Ethnicity=Hispanic or Latino. The 26 individuals classified as Unknown provided no information for either Race or Ethnicity.

Classification

- Logistic regression of CMV burden vs. CMV status
- Leave-one-out cross-validation Cross-validation results

HLA-restriction of CMV-associated TCRβ sequences

Incidence of previously reported CMV-reactive TCRβ sequences in this cohort

FIG. 12

Concordance with Previous Literature

| | this study | | | | previous publications | | | | | |
|---|---|---|---|---|---|---|---|---|---|---|
| aa sequence | V gene | J gene | HLA association | public | V gene* | match? | J gene* | match? | HLA association | match? | Ref. |
| CASSLAPGATNEKLFF | TCRBV07-06*01 | TCRBJ01-04*03 | HLA-A2 | yes | 6S3 (07-06) | ✓ | 1S4 (01-04) | ✓ | HLA-A2 | ✓ | Trautmann et al., 2005 |
| | | | | | 7-6 (07-06) | ✓ | 1-4 (01-04) | ✓ | HLA-A2 | ✓ | Price et al., 2005 |
| | | | | | 7-6 (07-06) | ✓ | 1-4 (01-04) | ✓ | HLA-A2 | ✓ | Venturi et al., 2008 |
| | | | | | 6.2/7-9 (07-08 or -09) | ✗ | 1-4 (01-04) | ✓ | HLA-A2 | ✓ | Miconnet et al. 2011 |
| (redacted) | TCRBV07-09 | TCRBJ02-01*03 | HLA-B7, HLA-A3 | yes | 6.4 (07-06) | ✗ | 2-1 (02-01) | ✓ | HLA-B7 | ✓ | Weekes et al., 1999 |
| | | | | | 6.2/7-9 (07-08 or -09) | ✓ | 2.1 (02-01) | ✓ | HLA-B7 | ✓ | Miconnet et al, 2011 |
| (redacted) | TCRBV04-03*01 | TCRBJ01-01*03 | HLA-B7, HLA-A3 | no | 7.2 (04-03) | ✓ | 1.1 (01-01) | ✓ | HLA-B7 | ✓ | Weekes et al., 1999 |
| (redacted) | TCRBV07-02*01 | TCRBJ02-01*03 | - | no | 6.1 (07-03) | ✗ | 2.1 (02-01) | ✓ | HLA-A2 | NA | Peggs et al., 2003 |
| (redacted) | TCRBV12 | TCRBJ01-02*03 | HLA-A2 | no | 12.4 (12-04) | ✓ | 1-2 (01-02) | ✓ | HLA-A2 | ✓ | Venturi et al., 2008 |

(*) Reported gene, followed by name in current nomenclature (as per IMGT); for Peggs et al. the identity of the J gene was deduced from the aminoacid sequence.

Feature selection

Feature vector for each subject

- Apply a P value cutoff to identify a set of feature TCRs from the previous list
- Check FDR by permutation of allele status
- For HLA-A2, 288 features at $p \leq 10^{-4}$, FDR = .1
- Compute abundance of each feature TCR in each subject

Machine learning

- Fit a logistic regression model to feature data $$\Pr(\text{HLA-A2+} \mid \mathbf{x}) = \frac{1}{1 - e^{-(\beta_0 + \beta \cdot x)}}$$

- $x$ → vector of abundances for the feature clones
- $\beta$ → coefficients for each feature, fit to maximize likelihood of training data

FIG. 17
Inferring allele status

- Cross validation:
  - Leave one subject out of the data set
  - Perform feature TCR identification
  - Fit logistic regression model
  - Use model to infer allele status for the subject held out
- Perform cross validation for each subject
- Training on the complete data set allows classification of novel subjects

Cross validation accuracy

- Based on 78 rounds of cross validation+

SEQUENCE LISTING

```
<160> NUMBER OF SEQ ID NOS: 163

<210> SEQ ID NO 1
<211> LENGTH: 13
<212> TYPE: PRT
<213> ORGANISM: Homo sapiens

<400> SEQUENCE: 1

Cys Ala Ser Ser Gly Gln Gly Ala Tyr Glu Gln Tyr Phe
1               5                   10

<210> SEQ ID NO 2
<211> LENGTH: 15
<212> TYPE: PRT
<213> ORGANISM: Homo sapiens

<400> SEQUENCE: 2
```

Cys Ala Ser Ser Pro Asp Arg Val Gly Gln Glu Thr Gln Tyr Phe
1               5                   10                  15

<210> SEQ ID NO 3
<211> LENGTH: 15
<212> TYPE: PRT
<213> ORGANISM: Homo sapiens

<400> SEQUENCE: 3

Cys Ala Ser Ser Ile Gly Pro Leu Glu His Asn Glu Gln Phe Phe
1               5                   10                  15

<210> SEQ ID NO 4
<211> LENGTH: 13
<212> TYPE: PRT
<213> ORGANISM: Homo sapiens

<400> SEQUENCE: 4

Cys Ala Ser Ser Ile Glu Gly Asn Gln Pro Gln His Phe
1               5                   10

<210> SEQ ID NO 5
<211> LENGTH: 15
<212> TYPE: PRT
<213> ORGANISM: Homo sapiens

<400> SEQUENCE: 5

Cys Ala Ser Ser Leu Val Ala Gly Gly Arg Glu Thr Gln Tyr Phe
1               5                   10                  15

<210> SEQ ID NO 6
<211> LENGTH: 13
<212> TYPE: PRT
<213> ORGANISM: Homo sapiens

<400> SEQUENCE: 6

Cys Ala Ser Ser Leu Glu Ala Glu Tyr Glu Gln Tyr Phe
1               5                   10

<210> SEQ ID NO 7
<211> LENGTH: 11
<212> TYPE: PRT
<213> ORGANISM: Homo sapiens

<400> SEQUENCE: 7

Cys Ala Thr Ser Asp Gly Asp Glu Gln Phe Phe
1               5                   10

<210> SEQ ID NO 8
<211> LENGTH: 16
<212> TYPE: PRT
<213> ORGANISM: Homo sapiens

<400> SEQUENCE: 8

Cys Ala Ser Ser Leu Ala Pro Gly Ala Thr Asn Glu Lys Leu Phe Phe
1               5                   10                  15

<210> SEQ ID NO 9
<211> LENGTH: 13
<212> TYPE: PRT
<213> ORGANISM: Homo sapiens

<400> SEQUENCE: 9

Cys Ala Ser Ser Arg Gly Arg Gln Glu Thr Gln Tyr Phe

```
1               5                   10
```

<210> SEQ ID NO 10
<211> LENGTH: 15
<212> TYPE: PRT
<213> ORGANISM: Homo sapiens

<400> SEQUENCE: 10

```
Cys Ala Ser Ser Ala Gly Gln Gly Val Thr Tyr Glu Gln Tyr Phe
1               5                   10                  15
```

<210> SEQ ID NO 11
<211> LENGTH: 12
<212> TYPE: PRT
<213> ORGANISM: Homo sapiens

<400> SEQUENCE: 11

```
Cys Ala Ser Ser Leu Arg Arg Glu Lys Leu Phe Phe
1               5                   10
```

<210> SEQ ID NO 12
<211> LENGTH: 16
<212> TYPE: PRT
<213> ORGANISM: Homo sapiens

<400> SEQUENCE: 12

```
Cys Ala Ser Ser Leu Ile Gly Val Ser Ser Tyr Asn Glu Gln Phe Phe
1               5                   10                  15
```

<210> SEQ ID NO 13
<211> LENGTH: 15
<212> TYPE: PRT
<213> ORGANISM: Homo sapiens

<400> SEQUENCE: 13

```
Cys Ala Ser Ser Phe Pro Thr Ser Gly Gln Glu Thr Gln Tyr Phe
1               5                   10                  15
```

<210> SEQ ID NO 14
<211> LENGTH: 13
<212> TYPE: PRT
<213> ORGANISM: Homo sapiens

<400> SEQUENCE: 14

```
Cys Ala Ser Ser Pro Gln Arg Asn Thr Glu Ala Phe Phe
1               5                   10
```

<210> SEQ ID NO 15
<211> LENGTH: 13
<212> TYPE: PRT
<213> ORGANISM: Homo sapiens

<400> SEQUENCE: 15

```
Cys Ser Val Arg Asp Asn Phe Asn Gln Pro Gln His Phe
1               5                   10
```

<210> SEQ ID NO 16
<211> LENGTH: 15
<212> TYPE: PRT
<213> ORGANISM: Homo sapiens

<400> SEQUENCE: 16

```
Cys Ala Thr Ser Arg Asp Ser Gln Gly Ser Tyr Gly Tyr Thr Phe
1               5                   10                  15
```

```
<210> SEQ ID NO 17
<211> LENGTH: 11
<212> TYPE: PRT
<213> ORGANISM: Homo sapiens

<400> SEQUENCE: 17

Cys Ala Ser Ser Pro Gly Asp Glu Gln Tyr Phe
1               5                   10

<210> SEQ ID NO 18
<211> LENGTH: 15
<212> TYPE: PRT
<213> ORGANISM: Homo sapiens

<400> SEQUENCE: 18

Cys Ala Ser Ser Gln Thr Gly Gly Arg Asn Gln Pro Gln His Phe
1               5                   10                  15

<210> SEQ ID NO 19
<211> LENGTH: 14
<212> TYPE: PRT
<213> ORGANISM: Homo sapiens

<400> SEQUENCE: 19

Cys Ala Ser Ser Gln Asn Arg Gly Gln Glu Thr Gln Tyr Phe
1               5                   10

<210> SEQ ID NO 20
<211> LENGTH: 15
<212> TYPE: PRT
<213> ORGANISM: Homo sapiens

<400> SEQUENCE: 20

Cys Ala Ser Ser Leu Val Ile Gly Gly Asp Thr Glu Ala Phe Phe
1               5                   10                  15

<210> SEQ ID NO 21
<211> LENGTH: 14
<212> TYPE: PRT
<213> ORGANISM: Homo sapiens

<400> SEQUENCE: 21

Cys Ala Ser Ser Phe His Gly Phe Asn Gln Pro Gln His Phe
1               5                   10

<210> SEQ ID NO 22
<211> LENGTH: 15
<212> TYPE: PRT
<213> ORGANISM: Homo sapiens

<400> SEQUENCE: 22

Cys Ala Ser Ser Arg Leu Ala Gly Gly Thr Asp Thr Gln Tyr Phe
1               5                   10                  15

<210> SEQ ID NO 23
<211> LENGTH: 15
<212> TYPE: PRT
<213> ORGANISM: Homo sapiens

<400> SEQUENCE: 23

Cys Ala Ser Ser Leu Pro Ser Gly Leu Thr Asp Thr Gln Tyr Phe
1               5                   10                  15

<210> SEQ ID NO 24
```

```
<211> LENGTH: 15
<212> TYPE: PRT
<213> ORGANISM: Homo sapiens

<400> SEQUENCE: 24

Cys Ala Thr Ser Arg Asp Thr Gln Gly Ser Tyr Gly Tyr Thr Phe
1               5                   10                  15

<210> SEQ ID NO 25
<211> LENGTH: 11
<212> TYPE: PRT
<213> ORGANISM: Homo sapiens

<400> SEQUENCE: 25

Cys Ala Thr Ser Asp Gly Asp Thr Gln Tyr Phe
1               5                   10

<210> SEQ ID NO 26
<211> LENGTH: 15
<212> TYPE: PRT
<213> ORGANISM: Homo sapiens

<400> SEQUENCE: 26

Cys Ala Ser Ser Leu Val Ala Ser Gly Arg Glu Thr Gln Tyr Phe
1               5                   10                  15

<210> SEQ ID NO 27
<211> LENGTH: 14
<212> TYPE: PRT
<213> ORGANISM: Homo sapiens

<400> SEQUENCE: 27

Cys Ala Ser Ser Ile Trp Gly Leu Asp Thr Glu Ala Phe Phe
1               5                   10

<210> SEQ ID NO 28
<211> LENGTH: 11
<212> TYPE: PRT
<213> ORGANISM: Homo sapiens

<400> SEQUENCE: 28

Cys Ala Ser Ser Pro Gly Asp Glu Gln Phe Phe
1               5                   10

<210> SEQ ID NO 29
<211> LENGTH: 13
<212> TYPE: PRT
<213> ORGANISM: Homo sapiens

<400> SEQUENCE: 29

Cys Ala Ser Ser Pro Ser Thr Gly Thr Glu Ala Phe Phe
1               5                   10

<210> SEQ ID NO 30
<211> LENGTH: 14
<212> TYPE: PRT
<213> ORGANISM: Homo sapiens

<400> SEQUENCE: 30

Cys Ser Val Glu Glu Asp Glu Gly Ile Tyr Gly Tyr Thr Phe
1               5                   10

<210> SEQ ID NO 31
<211> LENGTH: 13
<212> TYPE: PRT
```

<213> ORGANISM: Homo sapiens

<400> SEQUENCE: 31

Cys Ala Ser Ser Glu Ile Pro Asn Thr Glu Ala Phe Phe
1               5                   10

<210> SEQ ID NO 32
<211> LENGTH: 16
<212> TYPE: PRT
<213> ORGANISM: Homo sapiens

<400> SEQUENCE: 32

Cys Ala Ser Ser Gln Val Pro Gly Gln Gly Asp Asn Glu Gln Phe Phe
1               5                   10                  15

<210> SEQ ID NO 33
<211> LENGTH: 14
<212> TYPE: PRT
<213> ORGANISM: Homo sapiens

<400> SEQUENCE: 33

Cys Ala Ser Ser Pro Ala Gly Leu Asn Thr Glu Ala Phe Phe
1               5                   10

<210> SEQ ID NO 34
<211> LENGTH: 13
<212> TYPE: PRT
<213> ORGANISM: Homo sapiens

<400> SEQUENCE: 34

Cys Ala Ser Ser Leu Gly Leu Lys Gly Thr Gln Tyr Phe
1               5                   10

<210> SEQ ID NO 35
<211> LENGTH: 13
<212> TYPE: PRT
<213> ORGANISM: Homo sapiens

<400> SEQUENCE: 35

Cys Ala Ser Ser Gly Asp Arg Leu Tyr Glu Gln Tyr Phe
1               5                   10

<210> SEQ ID NO 36
<211> LENGTH: 13
<212> TYPE: PRT
<213> ORGANISM: Homo sapiens

<400> SEQUENCE: 36

Cys Ser Val Arg Asp Asn Tyr Asn Gln Pro Gln His Phe
1               5                   10

<210> SEQ ID NO 37
<211> LENGTH: 15
<212> TYPE: PRT
<213> ORGANISM: Homo sapiens

<400> SEQUENCE: 37

Cys Ala Ser Ser Tyr Gly Gly Leu Gly Ser Tyr Glu Gln Tyr Phe
1               5                   10                  15

<210> SEQ ID NO 38
<211> LENGTH: 14
<212> TYPE: PRT

-continued

<400> SEQUENCE: 38

Cys Ala Ser Asn Arg Asp Arg Gly Arg Tyr Glu Gln Tyr Phe
1               5                   10

<210> SEQ ID NO 39
<211> LENGTH: 13
<212> TYPE: PRT
<213> ORGANISM: Homo sapiens

<400> SEQUENCE: 39

Cys Ala Ser Met Gly Gly Ala Ser Tyr Glu Gln Tyr Phe
1               5                   10

<210> SEQ ID NO 40
<211> LENGTH: 15
<212> TYPE: PRT
<213> ORGANISM: Homo sapiens

<400> SEQUENCE: 40

Cys Ala Ser Ser Leu Gly Val Gly Pro Tyr Asn Glu Gln Phe Phe
1               5                   10                  15

<210> SEQ ID NO 41
<211> LENGTH: 14
<212> TYPE: PRT
<213> ORGANISM: Homo sapiens

<400> SEQUENCE: 41

Cys Ala Ser Ser Leu Gly Gly Ala Gly Asp Thr Gln Tyr Phe
1               5                   10

<210> SEQ ID NO 42
<211> LENGTH: 14
<212> TYPE: PRT
<213> ORGANISM: Homo sapiens

<400> SEQUENCE: 42

Cys Ala Thr Ser Arg Gly Thr Val Ser Tyr Glu Gln Tyr Phe
1               5                   10

<210> SEQ ID NO 43
<211> LENGTH: 11
<212> TYPE: PRT
<213> ORGANISM: Homo sapiens

<400> SEQUENCE: 43

Cys Ala Thr Ser Asp Gly Glu Thr Gln Tyr Phe
1               5                   10

<210> SEQ ID NO 44
<211> LENGTH: 15
<212> TYPE: PRT
<213> ORGANISM: Homo sapiens

<400> SEQUENCE: 44

Cys Ala Ser Ser Glu Ala Arg Gly Gly Val Glu Lys Leu Phe Phe
1               5                   10                  15

<210> SEQ ID NO 45
<211> LENGTH: 14
<212> TYPE: PRT
<213> ORGANISM: Homo sapiens

<400> SEQUENCE: 45

Cys Ala Ser Ser Leu Asn Arg Gly Gln Glu Thr Gln Tyr Phe
1               5                   10

<210> SEQ ID NO 46
<211> LENGTH: 13
<212> TYPE: PRT
<213> ORGANISM: Homo sapiens

<400> SEQUENCE: 46

Cys Ser Val Arg Asp Asn His Asn Gln Pro Gln His Phe
1               5                   10

<210> SEQ ID NO 47
<211> LENGTH: 15
<212> TYPE: PRT
<213> ORGANISM: Homo sapiens

<400> SEQUENCE: 47

Cys Ala Ser Ser Glu Ser Gly His Arg Asn Gln Pro Gln His Phe
1               5                   10                  15

<210> SEQ ID NO 48
<211> LENGTH: 15
<212> TYPE: PRT
<213> ORGANISM: Homo sapiens

<400> SEQUENCE: 48

Cys Ser Ala Ser Pro Gly Gln Gly Ala Ser Tyr Gly Tyr Thr Phe
1               5                   10                  15

<210> SEQ ID NO 49
<211> LENGTH: 12
<212> TYPE: PRT
<213> ORGANISM: Homo sapiens

<400> SEQUENCE: 49

Cys Ala Ser Ser Glu Ala Arg Thr Arg Ala Phe Phe
1               5                   10

<210> SEQ ID NO 50
<211> LENGTH: 12
<212> TYPE: PRT
<213> ORGANISM: Homo sapiens

<400> SEQUENCE: 50

Cys Ala Ser Arg Pro Thr Gly Tyr Glu Gln Tyr Phe
1               5                   10

<210> SEQ ID NO 51
<211> LENGTH: 14
<212> TYPE: PRT
<213> ORGANISM: Homo sapiens

<400> SEQUENCE: 51

Cys Ala Ser Ser Val Thr Gly Gly Thr Asp Thr Gln Tyr Phe
1               5                   10

<210> SEQ ID NO 52
<211> LENGTH: 15
<212> TYPE: PRT
<213> ORGANISM: Homo sapiens

<400> SEQUENCE: 52

Cys Ala Ser Ser Arg Leu Ala Ala Ser Thr Asp Thr Gln Tyr Phe
1               5                   10                  15

<210> SEQ ID NO 53
<211> LENGTH: 15
<212> TYPE: PRT
<213> ORGANISM: Homo sapiens

<400> SEQUENCE: 53

Cys Ala Thr Ser Asp Ser Val Thr Asn Thr Gly Glu Leu Phe Phe
1               5                   10                  15

<210> SEQ ID NO 54
<211> LENGTH: 15
<212> TYPE: PRT
<213> ORGANISM: Homo sapiens

<400> SEQUENCE: 54

Cys Ala Ser Ser Arg Asn Arg Glu Ser Asn Gln Pro Gln His Phe
1               5                   10                  15

<210> SEQ ID NO 55
<211> LENGTH: 13
<212> TYPE: PRT
<213> ORGANISM: Homo sapiens

<400> SEQUENCE: 55

Cys Ala Ser Ser Ala Gln Gly Ala Tyr Glu Gln Tyr Phe
1               5                   10

<210> SEQ ID NO 56
<211> LENGTH: 15
<212> TYPE: PRT
<213> ORGANISM: Homo sapiens

<400> SEQUENCE: 56

Cys Ala Ser Ser Ile Gln Gly Tyr Ser Asn Gln Pro Gln His Phe
1               5                   10                  15

<210> SEQ ID NO 57
<211> LENGTH: 15
<212> TYPE: PRT
<213> ORGANISM: Homo sapiens

<400> SEQUENCE: 57

Cys Ala Ser Ser Tyr Asn Pro Tyr Ser Asn Gln Pro Gln His Phe
1               5                   10                  15

<210> SEQ ID NO 58
<211> LENGTH: 17
<212> TYPE: PRT
<213> ORGANISM: Homo sapiens

<400> SEQUENCE: 58

Cys Ala Ser Ser Leu Gly His Arg Asp Pro Asn Thr Gly Glu Leu Phe
1               5                   10                  15

Phe

<210> SEQ ID NO 59
<211> LENGTH: 13
<212> TYPE: PRT
<213> ORGANISM: Homo sapiens

<400> SEQUENCE: 59

Cys Ala Ser Ser Thr Thr Gly Gly Asp Gly Tyr Thr Phe
1               5                   10

<210> SEQ ID NO 60
<211> LENGTH: 15
<212> TYPE: PRT
<213> ORGANISM: Homo sapiens

<400> SEQUENCE: 60

Cys Ala Ser Ser Val Leu Ala Gly Pro Thr Asp Thr Gln Tyr Phe
1               5                   10                  15

<210> SEQ ID NO 61
<211> LENGTH: 12
<212> TYPE: PRT
<213> ORGANISM: Homo sapiens

<400> SEQUENCE: 61

Cys Ala Ser Ser Tyr Arg Gln Glu Thr Gln Tyr Phe
1               5                   10

<210> SEQ ID NO 62
<211> LENGTH: 13
<212> TYPE: PRT
<213> ORGANISM: Homo sapiens

<400> SEQUENCE: 62

Cys Ala Ser Ser Ser Gly Gln Val Tyr Gly Tyr Thr Phe
1               5                   10

<210> SEQ ID NO 63
<211> LENGTH: 12
<212> TYPE: PRT
<213> ORGANISM: Homo sapiens

<400> SEQUENCE: 63

Cys Ala Ser Gly Arg Asp Thr Tyr Glu Gln Tyr Phe
1               5                   10

<210> SEQ ID NO 64
<211> LENGTH: 16
<212> TYPE: PRT
<213> ORGANISM: Homo sapiens

<400> SEQUENCE: 64

Cys Ala Thr Ser Asp Ser Arg Thr Gly Gly Gln Glu Thr Gln Tyr Phe
1               5                   10                  15

<210> SEQ ID NO 65
<211> LENGTH: 16
<212> TYPE: PRT
<213> ORGANISM: Homo sapiens

<400> SEQUENCE: 65

Cys Ala Ser Ser Ser Pro Gly Arg Ser Gly Ala Asn Val Leu Thr Phe
1               5                   10                  15

<210> SEQ ID NO 66
<211> LENGTH: 12
<212> TYPE: PRT
<213> ORGANISM: Homo sapiens

<400> SEQUENCE: 66

Cys Ala Ser Ser Tyr Gly Gly Glu Gly Tyr Thr Phe
1               5                   10

```
<210> SEQ ID NO 67
<211> LENGTH: 14
<212> TYPE: PRT
<213> ORGANISM: Homo sapiens

<400> SEQUENCE: 67

Cys Ala Ser Ser Leu Ala Gly Val Asp Tyr Glu Gln Tyr Phe
1               5                   10

<210> SEQ ID NO 68
<211> LENGTH: 13
<212> TYPE: PRT
<213> ORGANISM: Homo sapiens

<400> SEQUENCE: 68

Cys Ala Ser Ser Leu Gln Gly Ala Asp Thr Gln Tyr Phe
1               5                   10

<210> SEQ ID NO 69
<211> LENGTH: 13
<212> TYPE: PRT
<213> ORGANISM: Homo sapiens

<400> SEQUENCE: 69

Cys Ala Ser Ser Leu Glu Ala Glu Asn Glu Gln Phe Phe
1               5                   10

<210> SEQ ID NO 70
<211> LENGTH: 16
<212> TYPE: PRT
<213> ORGANISM: Homo sapiens

<400> SEQUENCE: 70

Cys Ala Ser Ser Glu Ala Pro Ser Thr Ser Thr Asp Thr Gln Tyr Phe
1               5                   10                  15

<210> SEQ ID NO 71
<211> LENGTH: 13
<212> TYPE: PRT
<213> ORGANISM: Homo sapiens

<400> SEQUENCE: 71

Cys Ala Ser Ser Leu Glu Gly Gln Gln Pro Gln His Phe
1               5                   10

<210> SEQ ID NO 72
<211> LENGTH: 16
<212> TYPE: PRT
<213> ORGANISM: Homo sapiens

<400> SEQUENCE: 72

Cys Ala Ser Ser Leu Gly His Arg Asp Ser Ser Tyr Glu Gln Tyr Phe
1               5                   10                  15

<210> SEQ ID NO 73
<211> LENGTH: 13
<212> TYPE: PRT
<213> ORGANISM: Homo sapiens

<400> SEQUENCE: 73

Cys Ala Ser Ser Pro Ser Arg Asn Thr Glu Ala Phe Phe
1               5                   10

<210> SEQ ID NO 74
<211> LENGTH: 13
```

<212> TYPE: PRT
<213> ORGANISM: Homo sapiens

<400> SEQUENCE: 74

Cys Ser Ala Leu Gly His Ser Asn Gln Pro Gln His Phe
1               5                   10

<210> SEQ ID NO 75
<211> LENGTH: 14
<212> TYPE: PRT
<213> ORGANISM: Homo sapiens

<400> SEQUENCE: 75

Cys Ala Ser Ser His Arg Asp Arg Asn Tyr Glu Gln Tyr Phe
1               5                   10

<210> SEQ ID NO 76
<211> LENGTH: 15
<212> TYPE: PRT
<213> ORGANISM: Homo sapiens

<400> SEQUENCE: 76

Cys Ala Ser Ser Pro Pro Gly Gln Gly Ser Asp Thr Gln Tyr Phe
1               5                   10                  15

<210> SEQ ID NO 77
<211> LENGTH: 15
<212> TYPE: PRT
<213> ORGANISM: Homo sapiens

<400> SEQUENCE: 77

Cys Ala Ser Ser Leu Gln Gly Tyr Ser Asn Gln Pro Gln His Phe
1               5                   10                  15

<210> SEQ ID NO 78
<211> LENGTH: 16
<212> TYPE: PRT
<213> ORGANISM: Homo sapiens

<400> SEQUENCE: 78

Cys Ala Ser Ser Tyr Val Arg Thr Gly Gly Asn Tyr Gly Tyr Thr Phe
1               5                   10                  15

<210> SEQ ID NO 79
<211> LENGTH: 13
<212> TYPE: PRT
<213> ORGANISM: Homo sapiens

<400> SEQUENCE: 79

Cys Ala Ser Ser Arg Asp Arg Asn Tyr Gly Tyr Thr Phe
1               5                   10

<210> SEQ ID NO 80
<211> LENGTH: 15
<212> TYPE: PRT
<213> ORGANISM: Homo sapiens

<400> SEQUENCE: 80

Cys Ala Ser Ser Thr Gly Thr Ser Gly Ser Tyr Glu Gln Tyr Phe
1               5                   10                  15

<210> SEQ ID NO 81
<211> LENGTH: 14
<212> TYPE: PRT
<213> ORGANISM: Homo sapiens

```
<400> SEQUENCE: 81

Cys Ala Ser Arg Ser Asp Ser Gly Ala Asn Val Leu Thr Phe
1               5                   10

<210> SEQ ID NO 82
<211> LENGTH: 13
<212> TYPE: PRT
<213> ORGANISM: Homo sapiens

<400> SEQUENCE: 82

Cys Ala Thr Ser Arg Val Ala Gly Glu Thr Gln Tyr Phe
1               5                   10

<210> SEQ ID NO 83
<211> LENGTH: 13
<212> TYPE: PRT
<213> ORGANISM: Homo sapiens

<400> SEQUENCE: 83

Cys Ala Ser Ser Glu Glu Gly Ile Gln Pro Gln His Phe
1               5                   10

<210> SEQ ID NO 84
<211> LENGTH: 14
<212> TYPE: PRT
<213> ORGANISM: Homo sapiens

<400> SEQUENCE: 84

Cys Ala Ser Ser Leu Gly Gly Pro Gly Asp Thr Gln Tyr Phe
1               5                   10

<210> SEQ ID NO 85
<211> LENGTH: 15
<212> TYPE: PRT
<213> ORGANISM: Homo sapiens

<400> SEQUENCE: 85

Cys Ala Ser Ser Leu Val Ala Ala Gly Arg Glu Thr Gln Tyr Phe
1               5                   10                  15

<210> SEQ ID NO 86
<211> LENGTH: 14
<212> TYPE: PRT
<213> ORGANISM: Homo sapiens

<400> SEQUENCE: 86

Cys Ala Ser Arg Gly Gln Gly Trp Asp Glu Lys Leu Phe Phe
1               5                   10

<210> SEQ ID NO 87
<211> LENGTH: 14
<212> TYPE: PRT
<213> ORGANISM: Homo sapiens

<400> SEQUENCE: 87

Cys Ala Ser Ser Leu Glu Gly Gln Gly Phe Gly Tyr Thr Phe
1               5                   10

<210> SEQ ID NO 88
<211> LENGTH: 14
<212> TYPE: PRT
<213> ORGANISM: Homo sapiens

<400> SEQUENCE: 88
```

Cys Ala Ser Arg Asp Trp Asp Tyr Thr Asp Thr Gln Tyr Phe
1               5                   10

<210> SEQ ID NO 89
<211> LENGTH: 17
<212> TYPE: PRT
<213> ORGANISM: Homo sapiens

<400> SEQUENCE: 89

Cys Ala Ser Ser Arg Ser Gly Leu Ala Gly Asn Thr Gly Glu Leu Phe
1               5                   10                  15

Phe

<210> SEQ ID NO 90
<211> LENGTH: 16
<212> TYPE: PRT
<213> ORGANISM: Homo sapiens

<400> SEQUENCE: 90

Cys Ala Ser Ser Pro Gly Gln Glu Ala Gly Ala Asn Val Leu Thr Phe
1               5                   10                  15

<210> SEQ ID NO 91
<211> LENGTH: 14
<212> TYPE: PRT
<213> ORGANISM: Homo sapiens

<400> SEQUENCE: 91

Cys Ala Ser Ser Leu Gly Asp Arg Pro Asp Thr Gln Tyr Phe
1               5                   10

<210> SEQ ID NO 92
<211> LENGTH: 13
<212> TYPE: PRT
<213> ORGANISM: Homo sapiens

<400> SEQUENCE: 92

Cys Ala Ser Ser Phe Pro Gly Gly Glu Thr Gln Tyr Phe
1               5                   10

<210> SEQ ID NO 93
<211> LENGTH: 12
<212> TYPE: PRT
<213> ORGANISM: Homo sapiens

<400> SEQUENCE: 93

Cys Ala Ser Ser Leu Glu Thr Tyr Gly Tyr Thr Phe
1               5                   10

<210> SEQ ID NO 94
<211> LENGTH: 14
<212> TYPE: PRT
<213> ORGANISM: Homo sapiens

<400> SEQUENCE: 94

Cys Ala Ser Ser Ser Gly Gln Val Gln Glu Thr Gln Tyr Phe
1               5                   10

<210> SEQ ID NO 95
<211> LENGTH: 12
<212> TYPE: PRT
<213> ORGANISM: Homo sapiens

<400> SEQUENCE: 95

Cys Ala Ser Ser Phe Asp Asn Tyr Gly Tyr Thr Phe
1               5                   10

<210> SEQ ID NO 96
<211> LENGTH: 13
<212> TYPE: PRT
<213> ORGANISM: Homo sapiens

<400> SEQUENCE: 96

Cys Ala Ser Ser Glu Gly Ala Arg Gln Pro Gln His Phe
1               5                   10

<210> SEQ ID NO 97
<211> LENGTH: 15
<212> TYPE: PRT
<213> ORGANISM: Homo sapiens

<400> SEQUENCE: 97

Cys Ala Ser Ser Leu Thr Gly Gly Arg Asn Gln Pro Gln His Phe
1               5                   10                  15

<210> SEQ ID NO 98
<211> LENGTH: 13
<212> TYPE: PRT
<213> ORGANISM: Homo sapiens

<400> SEQUENCE: 98

Cys Ala Ser Ser Leu Leu Trp Asp Gln Pro Gln His Phe
1               5                   10

<210> SEQ ID NO 99
<211> LENGTH: 16
<212> TYPE: PRT
<213> ORGANISM: Homo sapiens

<400> SEQUENCE: 99

Cys Ala Ser Ser Leu Phe Gly Thr Gly Gly Asn Thr Glu Ala Phe Phe
1               5                   10                  15

<210> SEQ ID NO 100
<211> LENGTH: 12
<212> TYPE: PRT
<213> ORGANISM: Homo sapiens

<400> SEQUENCE: 100

Cys Ala Ser Ser Ile Ser Ala Gly Glu Ala Phe Phe
1               5                   10

<210> SEQ ID NO 101
<211> LENGTH: 15
<212> TYPE: PRT
<213> ORGANISM: Homo sapiens

<400> SEQUENCE: 101

Cys Ala Ser Ser Pro Pro Ser Gly Leu Thr Asp Thr Gln Tyr Phe
1               5                   10                  15

<210> SEQ ID NO 102
<211> LENGTH: 12
<212> TYPE: PRT
<213> ORGANISM: Homo sapiens

<400> SEQUENCE: 102

Cys Ala Ser Ser Pro Leu Ser Asp Thr Gln Tyr Phe

<210> SEQ ID NO 103
<211> LENGTH: 13
<212> TYPE: PRT
<213> ORGANISM: Homo sapiens

<400> SEQUENCE: 103

Cys Ala Ser Ser Arg Gly Thr Gly Glu Leu Phe Phe
1               5                   10

<210> SEQ ID NO 104
<211> LENGTH: 12
<212> TYPE: PRT
<213> ORGANISM: Homo sapiens

<400> SEQUENCE: 104

Cys Ala Ser Ser Tyr Ala Gly Asp Gly Tyr Thr Phe
1               5                   10

<210> SEQ ID NO 105
<211> LENGTH: 14
<212> TYPE: PRT
<213> ORGANISM: Homo sapiens

<400> SEQUENCE: 105

Cys Ala Ser Ser Asp Arg Gly Asn Thr Gly Glu Leu Phe Phe
1               5                   10

<210> SEQ ID NO 106
<211> LENGTH: 11
<212> TYPE: PRT
<213> ORGANISM: Homo sapiens

<400> SEQUENCE: 106

Cys Ala Ser Ser Pro Gly Gly Thr Gln Tyr Phe
1               5                   10

<210> SEQ ID NO 107
<211> LENGTH: 15
<212> TYPE: PRT
<213> ORGANISM: Homo sapiens

<400> SEQUENCE: 107

Cys Ala Ser Ser Leu Gly Asp Arg Ala Tyr Asn Glu Gln Phe Phe
1               5                   10                  15

<210> SEQ ID NO 108
<211> LENGTH: 15
<212> TYPE: PRT
<213> ORGANISM: Homo sapiens

<400> SEQUENCE: 108

Cys Ala Ser Ser Leu Arg Gly Ser Ser Tyr Asn Glu Gln Phe Phe
1               5                   10                  15

<210> SEQ ID NO 109
<211> LENGTH: 14
<212> TYPE: PRT
<213> ORGANISM: Homo sapiens

<400> SEQUENCE: 109

Cys Ala Ser Ser Leu Thr Ala Ser Ser Tyr Glu Gln Tyr Phe
1               5                   10

<210> SEQ ID NO 110
<211> LENGTH: 10
<212> TYPE: PRT
<213> ORGANISM: Homo sapiens

<400> SEQUENCE: 110

Cys Ser Ala Ser Asp His Glu Gln Tyr Phe
1               5                   10

<210> SEQ ID NO 111
<211> LENGTH: 14
<212> TYPE: PRT
<213> ORGANISM: Homo sapiens

<400> SEQUENCE: 111

Cys Ala Ser Ser Gln Gly Arg His Thr Asp Thr Gln Tyr Phe
1               5                   10

<210> SEQ ID NO 112
<211> LENGTH: 15
<212> TYPE: PRT
<213> ORGANISM: Homo sapiens

<400> SEQUENCE: 112

Cys Ala Ser Ser Arg Pro Gly Gln Gly Asn Thr Glu Ala Phe Phe
1               5                   10                  15

<210> SEQ ID NO 113
<211> LENGTH: 12
<212> TYPE: PRT
<213> ORGANISM: Homo sapiens

<400> SEQUENCE: 113

Cys Ala Ser Ser Leu Val Gly Asp Gly Tyr Thr Phe
1               5                   10

<210> SEQ ID NO 114
<211> LENGTH: 14
<212> TYPE: PRT
<213> ORGANISM: Homo sapiens

<400> SEQUENCE: 114

Cys Ala Ser Ser Leu Gly Ala Gly Asn Gln Pro Gln His Phe
1               5                   10

<210> SEQ ID NO 115
<211> LENGTH: 13
<212> TYPE: PRT
<213> ORGANISM: Homo sapiens

<400> SEQUENCE: 115

Cys Ala Ser Ser Leu Thr Asp Thr Gly Glu Leu Phe Phe
1               5                   10

<210> SEQ ID NO 116
<211> LENGTH: 16
<212> TYPE: PRT
<213> ORGANISM: Homo sapiens

<400> SEQUENCE: 116

Cys Ala Ser Ser Leu Thr Gly Gly Asn Ser Gly Asn Thr Ile Tyr Phe
1               5                   10                  15

<210> SEQ ID NO 117

```
<211> LENGTH: 13
<212> TYPE: PRT
<213> ORGANISM: Homo sapiens

<400> SEQUENCE: 117

Cys Ala Trp Arg Gly Thr Gly Asn Ser Pro Leu His Phe
1               5                   10

<210> SEQ ID NO 118
<211> LENGTH: 12
<212> TYPE: PRT
<213> ORGANISM: Homo sapiens

<400> SEQUENCE: 118

Cys Ala Ser Ala Ser Ala Asn Tyr Gly Tyr Thr Phe
1               5                   10

<210> SEQ ID NO 119
<211> LENGTH: 14
<212> TYPE: PRT
<213> ORGANISM: Homo sapiens

<400> SEQUENCE: 119

Cys Ala Ser Ser Leu Gln Ala Gly Ala Asn Glu Gln Phe Phe
1               5                   10

<210> SEQ ID NO 120
<211> LENGTH: 14
<212> TYPE: PRT
<213> ORGANISM: Homo sapiens

<400> SEQUENCE: 120

Cys Ala Ser Ser Glu Glu Ala Gly Gly Ser Gly Tyr Thr Phe
1               5                   10

<210> SEQ ID NO 121
<211> LENGTH: 12
<212> TYPE: PRT
<213> ORGANISM: Homo sapiens

<400> SEQUENCE: 121

Cys Ala Ser Arg Thr Gly Glu Ser Gly Tyr Thr Phe
1               5                   10

<210> SEQ ID NO 122
<211> LENGTH: 11
<212> TYPE: PRT
<213> ORGANISM: Homo sapiens

<400> SEQUENCE: 122

Cys Ala Ser Ser Gly Leu Asn Glu Gln Phe Phe
1               5                   10

<210> SEQ ID NO 123
<211> LENGTH: 14
<212> TYPE: PRT
<213> ORGANISM: Homo sapiens

<400> SEQUENCE: 123

Cys Ala Ser Ser Trp Asp Arg Asp Asn Ser Pro Leu His Phe
1               5                   10

<210> SEQ ID NO 124
<211> LENGTH: 14
<212> TYPE: PRT
```

<213> ORGANISM: Homo sapiens

<400> SEQUENCE: 124

Cys Ala Ser Ser Ile Arg Thr Asn Tyr Tyr Gly Tyr Thr Phe
1               5                   10

<210> SEQ ID NO 125
<211> LENGTH: 10
<212> TYPE: PRT
<213> ORGANISM: Homo sapiens

<400> SEQUENCE: 125

Cys Ser Ala Arg Ser Pro Glu Ala Phe Phe
1               5                   10

<210> SEQ ID NO 126
<211> LENGTH: 15
<212> TYPE: PRT
<213> ORGANISM: Homo sapiens

<400> SEQUENCE: 126

Cys Ala Ser Ser Arg Gly Thr Gly Ala Thr Asp Thr Gln Tyr Phe
1               5                   10                  15

<210> SEQ ID NO 127
<211> LENGTH: 14
<212> TYPE: PRT
<213> ORGANISM: Homo sapiens

<400> SEQUENCE: 127

Cys Ala Ser Ser Pro Arg Val Ser Asn Gln Pro Gln His Phe
1               5                   10

<210> SEQ ID NO 128
<211> LENGTH: 15
<212> TYPE: PRT
<213> ORGANISM: Homo sapiens

<400> SEQUENCE: 128

Cys Ala Ile Ser Glu Ser Gln Asp Arg Gly His Glu Gln Tyr Phe
1               5                   10                  15

<210> SEQ ID NO 129
<211> LENGTH: 14
<212> TYPE: PRT
<213> ORGANISM: Homo sapiens

<400> SEQUENCE: 129

Cys Ala Ser Ser Leu Gly Arg Gly Tyr Glu Lys Leu Phe Phe
1               5                   10

<210> SEQ ID NO 130
<211> LENGTH: 13
<212> TYPE: PRT
<213> ORGANISM: Homo sapiens

<400> SEQUENCE: 130

Cys Ser Val Glu Val Arg Gly Thr Asp Thr Gln Tyr Phe
1               5                   10

<210> SEQ ID NO 131
<211> LENGTH: 13
<212> TYPE: PRT
<213> ORGANISM: Homo sapiens

<400> SEQUENCE: 131

Cys Ala Ser Arg Gly Gln Gly Ala Gly Glu Leu Phe Phe
1               5                   10

<210> SEQ ID NO 132
<211> LENGTH: 14
<212> TYPE: PRT
<213> ORGANISM: Homo sapiens

<400> SEQUENCE: 132

Cys Ala Thr Ser Arg Glu Gly Ser Gly Tyr Glu Gln Tyr Phe
1               5                   10

<210> SEQ ID NO 133
<211> LENGTH: 12
<212> TYPE: PRT
<213> ORGANISM: Homo sapiens

<400> SEQUENCE: 133

Cys Ala Ser Ser Leu Gly Trp Thr Glu Ala Phe Phe
1               5                   10

<210> SEQ ID NO 134
<211> LENGTH: 15
<212> TYPE: PRT
<213> ORGANISM: Homo sapiens

<400> SEQUENCE: 134

Cys Ala Ser Ser Leu Gly Ser Ser Ser Tyr Asn Glu Gln Phe Phe
1               5                   10                  15

<210> SEQ ID NO 135
<211> LENGTH: 13
<212> TYPE: PRT
<213> ORGANISM: Homo sapiens

<400> SEQUENCE: 135

Cys Ala Ser Ser Ser Ala Gly Ala Asp Thr Gln Tyr Phe
1               5                   10

<210> SEQ ID NO 136
<211> LENGTH: 13
<212> TYPE: PRT
<213> ORGANISM: Homo sapiens

<400> SEQUENCE: 136

Cys Ala Ser Ser Glu Arg Lys Asn Tyr Gly Tyr Thr Phe
1               5                   10

<210> SEQ ID NO 137
<211> LENGTH: 15
<212> TYPE: PRT
<213> ORGANISM: Homo sapiens

<400> SEQUENCE: 137

Cys Ala Ser Arg Asp Arg Asp Arg Val Asn Thr Glu Ala Phe Phe
1               5                   10                  15

<210> SEQ ID NO 138
<211> LENGTH: 11
<212> TYPE: PRT
<213> ORGANISM: Homo sapiens

<400> SEQUENCE: 138

Cys Ala Ser Ser Arg Val Gly Glu Gln Phe Phe
1               5                   10

<210> SEQ ID NO 139
<211> LENGTH: 13
<212> TYPE: PRT
<213> ORGANISM: Homo sapiens

<400> SEQUENCE: 139

Cys Ala Ser Ser Pro Arg Trp Gln Glu Thr Gln Tyr Phe
1               5                   10

<210> SEQ ID NO 140
<211> LENGTH: 11
<212> TYPE: PRT
<213> ORGANISM: Homo sapiens

<400> SEQUENCE: 140

Cys Ala Ser Thr Pro Gly Asp Thr Ile Tyr Phe
1               5                   10

<210> SEQ ID NO 141
<211> LENGTH: 14
<212> TYPE: PRT
<213> ORGANISM: Homo sapiens

<400> SEQUENCE: 141

Cys Ala Ser Ser Glu Asn Gly Gly Asn Gln Pro Gln His Phe
1               5                   10

<210> SEQ ID NO 142
<211> LENGTH: 12
<212> TYPE: PRT
<213> ORGANISM: Homo sapiens

<400> SEQUENCE: 142

Cys Ala Ser Ser Tyr Pro Gly Glu Thr Gln Tyr Phe
1               5                   10

<210> SEQ ID NO 143
<211> LENGTH: 39
<212> TYPE: DNA
<213> ORGANISM: Homo sapiens

<400> SEQUENCE: 143
tgtgccagca gtgggggggc aaacaccggg cagctctac                          39

<210> SEQ ID NO 144
<211> LENGTH: 12
<212> TYPE: DNA
<213> ORGANISM: Homo sapiens

<400> SEQUENCE: 144
agtggggggg ca                                                       12

<210> SEQ ID NO 145
<211> LENGTH: 39
<212> TYPE: DNA
<213> ORGANISM: Homo sapiens

<400> SEQUENCE: 145
tgtgccagca gtgggggggc gaacaccggg cagctctac                          39

<210> SEQ ID NO 146

```
<211> LENGTH: 12
<212> TYPE: DNA
<213> ORGANISM: Homo sapiens

<400> SEQUENCE: 146
agtggggggg cg                                                           12

<210> SEQ ID NO 147
<211> LENGTH: 39
<212> TYPE: DNA
<213> ORGANISM: Homo sapiens

<400> SEQUENCE: 147
tgtgccagca gcggggggc aaacaccggg cagctctac                               39

<210> SEQ ID NO 148
<211> LENGTH: 12
<212> TYPE: DNA
<213> ORGANISM: Homo sapiens

<400> SEQUENCE: 148 agcgggggg ca                                                            12

<210> SEQ ID NO 149
<211> LENGTH: 13
<212> TYPE: PRT
<213> ORGANISM: Homo sapiens

<400> SEQUENCE: 149

Cys Ala Ser Ser Gly Gly Ala Asn Thr Gly Gln Leu Tyr
1               5                   10

<210> SEQ ID NO 150
<211> LENGTH: 14
<212> TYPE: PRT
<213> ORGANISM: Homo sapiens

<400> SEQUENCE: 150

Cys Ala Ser Ser Leu Glu Ala Gly Ala Gln Pro Gln His Phe
1               5                   10

<210> SEQ ID NO 151
<211> LENGTH: 13
<212> TYPE: PRT
<213> ORGANISM: Homo sapiens

<400> SEQUENCE: 151

Cys Ala Ser Ser Ile Arg Ser Gly Val Glu Gln Tyr Phe
1               5                   10

<210> SEQ ID NO 152
<211> LENGTH: 14
<212> TYPE: PRT
<213> ORGANISM: Homo sapiens

<400> SEQUENCE: 152

Cys Ser Ala Arg Asp Arg Gly Ile Gly Asn Thr Ile Tyr Phe
1               5                   10

<210> SEQ ID NO 153
<211> LENGTH: 13
<212> TYPE: PRT
<213> ORGANISM: Homo sapiens

<400> SEQUENCE: 153
```

Cys Ala Ser Ser Gln Ser Pro Gly Gly Thr Gln Tyr Phe
1               5                   10

<210> SEQ ID NO 154
<211> LENGTH: 12
<212> TYPE: PRT
<213> ORGANISM: Homo sapiens

<400> SEQUENCE: 154

Cys Ala Ser Ser Pro Glu Thr Gly Glu Ala Phe Phe
1               5                   10

<210> SEQ ID NO 155
<211> LENGTH: 13
<212> TYPE: PRT
<213> ORGANISM: Homo sapiens

<400> SEQUENCE: 155

Cys Ala Ser Ser Leu Arg Ser Thr Gly Glu Leu Phe Phe
1               5                   10

<210> SEQ ID NO 156
<211> LENGTH: 14
<212> TYPE: PRT
<213> ORGANISM: Homo sapiens

<400> SEQUENCE: 156

Cys Ala Ser Ser Glu Asn Ser Pro His Gln Pro Gln His Phe
1               5                   10

<210> SEQ ID NO 157
<211> LENGTH: 12
<212> TYPE: PRT
<213> ORGANISM: Homo sapiens

<400> SEQUENCE: 157

Cys Ala Ser Ser Gln Glu Ala Gly Pro Gln His Phe
1               5                   10

<210> SEQ ID NO 158
<211> LENGTH: 14
<212> TYPE: PRT
<213> ORGANISM: Homo sapiens

<400> SEQUENCE: 158

Cys Ala Ser Ser Ile Arg Asp Arg Gly Gln Pro Gln His Phe
1               5                   10

<210> SEQ ID NO 159
<211> LENGTH: 13
<212> TYPE: PRT
<213> ORGANISM: Homo sapiens

<400> SEQUENCE: 159

Cys Ala Ser Ser Tyr Gln Gly Gly Asn Glu Gln Phe Phe
1               5                   10

<210> SEQ ID NO 160
<211> LENGTH: 12
<212> TYPE: PRT
<213> ORGANISM: Homo sapiens

<400> SEQUENCE: 160

Cys Ala Ser Ser Gly Gly Ala Asn Val Leu Thr Phe

```
<210> SEQ ID NO 161
<211> LENGTH: 12
<212> TYPE: PRT
<213> ORGANISM: Homo sapiens

<400> SEQUENCE: 161

Cys Ser Val Glu Asp Leu Gly Tyr Gly Tyr Thr Phe
1               5                   10

<210> SEQ ID NO 162
<211> LENGTH: 15
<212> TYPE: PRT
<213> ORGANISM: Homo sapiens

<400> SEQUENCE: 162

Cys Ala Ser Arg Arg Gly Gly Ser Ser Tyr Asn Glu Gln Phe Phe
1               5                   10                  15

<210> SEQ ID NO 163
<211> LENGTH: 11
<212> TYPE: PRT
<213> ORGANISM: Homo sapiens

<400> SEQUENCE: 163

Cys Ala Ser Arg Ser Gly Thr Glu Ala Phe Phe
1               5                   10
```

METHODS FOR DIAGNOSING INFECTIOUS DISEASE AND DETERMINING HLA STATUS USING IMMUNE REPERTOIRE SEQUENCING

CROSS REFERENCE TO RELATED APPLICATIONS

This application is the national stage of International Patent Application No. PCT/US2016/019343, filed on Feb. 24, 2016, which claims the benefit of U.S. Provisional Patent Application No. 62/120,249, filed on Feb. 24, 2015, U.S. Provisional Patent Application No. 62/157,249, filed on May 5, 2015, and U.S. Provisional Patent Application No. 62/215,630, filed on Sep. 8, 2015. The contents of each of these applications are herein incorporated by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: ADBS-024_02US_SeqList_ST25.txt, date recorded: Aug. 23, 2017, file size 31,067 bytes).

BACKGROUND OF THE INVENTION

The cellular adaptive immune system conveys broad protection against infection by pathogens through the development of a vast and highly diverse repertoire of T cell receptor (TCR) genes, which encode cell-surface T cell receptors with randomized antigen specificity. The ability of a subject's adaptive immune system to adequately address an incipient infection relies on activation of an appropriate antigen-specific T-cell receptor (TCR). TCR-antigen interaction is mediated by the cell-surface presentation of foreign peptides by pathogen-infected cells in the context of major histocompatibility complex (MEW) proteins. Specifically, CD8⁺ T cells recognize antigen in the context of MHC class I proteins. Since MHC class I proteins are encoded by the human leukocyte antigen (HLA) loci A, B, and C, which are highly polymorphic, the antigen specificity of a TCR is modulated across individuals by HLA context.

When an antigen has been encountered, activated T cells proliferate by clonal expansion and reside in the memory T cell compartment for many years as a clonal population of cells (clones) with identical-by-descent rearranged TCR genes (Arstila T P, et al. A direct estimate of the human alphabeta T cell receptor diversity. Science 286: 958-961, 1999). Protection against future exposure to disease-causing pathogens is conferred by the ability of activated T cells to form long-lasting memory responses.

The majority of TCR diversity resides in the β chain of the TCR alpha/beta heterodimer. Each T cell clone is encoded by a single TCRβ allele that has been randomly rearranged from the germ-line TCRβ locus to form a mature TCRβ gene. Immense diversity is generated by combining non-contiguous TCRβ variable (V), diversity (D), and joining (J) region gene segments, which collectively encode the CDR3 region, the primary region of the TCRβ locus for determining antigen specificity. Deletion and template-independent insertion of nucleotides during rearrangement at the Vβ-Dβ and Dβ-Jβ junctions further add to the potential diversity of receptors that can be encoded (Cabaniols J P, et al. Most alpha/beta T cell receptor diversity is due to terminal deoxynucleotidyl transferase. J Exp Med 194: 1385-1390, 2001). Typically, at a given point in time, a healthy adult expresses approximately 10 million unique TCRβ chains on their $10^{12}$ circulating T cells (Robins H S, et al. (2009) Comprehensive assessment of T-cell receptor beta-chain diversity in alpha-beta T cells. Blood 114: 4099-4107). However, observing the same TCRβ chain independently in two individuals is thousands of times more common than would be expected if all rearrangements were equally likely (Robins H S, et al. (2010) Overlap and effective size of the human CD8+ T cell receptor repertoire. Science Translational Medicine 2: 47ra64). It is expected that there are many TCRβ sequences (especially those with few or no insertions) that are present in the naïve repertoires of most individuals and that these TCRβ sequences will reliably proliferate upon exposure to their associated antigen (V. Venturi, et al., The molecular basis for public T-cell responses? Nature reviews. Immunology 8, 231-238 (2008); published online EpubMar (10.1038/nri2260)). This over-representation of specific TCRβ sequence rearrangements in the naïve T cell repertoire forms the basis for public T cell responses.

Public T-cell responses occur when T cells bearing identical T-cell receptors (TCRs) are observed to dominate the response to the same antigenic epitope in multiple individuals. Many pathogenic antigens are known to induce such a public T cell response, in which a pathogenic antigen is targeted by the same T cell receptor sequence (and found to be immunodominant) in multiple individuals with specific HLA isotypes. H. Li et al., Determinants of public T cell responses. Cell research 22, 33-42 (2012); published online EpubJan (10.1038/cr.2012.1); H. Li, et al., Recombinatorial biases and convergent recombination determine inter-individual TCRbeta sharing in murine thymocytes. Journal of immunology (Baltimore, Md.: 1950) 189, 2404-2413 (2012); published online EpubSep 1 (10.4049/jimmunol.1102087). In other words, public T cell responses are observed when the space of potential high-avidity TCRβ chains that could bind to a particular antigen-MHC complex includes one or more TCRβ chains that also have a high likelihood of existing in the naïve repertoire at any given time. Thus, sequences associated with a public T cell response will only be intermittently present in the naïve compartment of subjects that have not been exposed to a particular antigen; however, such clones should consistently appear in the T cell repertoire of subjects who have been exposed to the antigen, having undergone clonal expansion after antigen stimulation.

Previous work on public T cell responses has identified individual examples of public T cell responses to diseases (including CMV, EBV, influenza, multiple sclerosis and other disease malignancies and autoimmune conditions), (Venturi V, et al. (2008) J Immunol 181: 7853-7862). These studies were limited by sequencing depth and the size of investigational cohorts. Typically, these public T cell responses were studied in the context of single antigens in a single HLA context, usually using antigen-MHC tetramers to purify antigen-specific T cells. However, because of technical limitations, only a relatively small number of public T cell responses have been identified to date. Not surprisingly, these results have been limited to the high frequency, easily observable public T cell responses that dominate the immune response to their target antigens. Therefore, these public responses represent only TCRβ sequences that are common to the naïve T cell compartment of nearly all adult subjects (i.e., available for antigen response), and misses both rare T cell rearrangements which are present in only some antigen-experienced patients due to rarity among naïve T cell sequences and T cell responses that are not immunodominant and therefore never comprise a sufficient fraction of the total T cell repertoire to be reliably observed with limited sequencing depth.

Further, TCR-antigen interaction is mediated by the cell-surface presentation of foreign peptides by pathogen-infected cells in the context of major histocompatibility complex (MHC) class I proteins. Since MHC class I proteins are encoded by the human leukocyte antigen (HLA) loci A, B, and C, which are highly polymorphic, the antigen specificity of a TCR is modulated across individuals by HLA context.

The binding of T cell receptors to antigens is mediated by MHC proteins, which present antigen on the surface of cells. MHC are encoded in humans by the HLA loci, which are highly polymorphic. This polymorphism leads to heterogeneous T cell responses to the same antigen across individuals and to differential positive and negative selection of specific T cell receptor sequences during thymic training. Determination of an individual's HLA alleles (HLA type) has several clinical applications. One example of a clinical application for HLA typing is testing an individual's suitability as a bone marrow transplant donor.

There is a need for improved methods to diagnose and/or predict an individual's status for an infectious disease, such as CMV, EBV, HPV, small pox, and others, with increased sensitivity and accuracy. Diagnostic methods are needed that harness the information about an individual's T cell receptor sequence profile, including the presence of public T cell clones, and assess the individual's infectious disease status based on the T cell receptor sequence profile. There is also a need for inferring an individual's HLA type based on the individual's T cell receptor sequence profile. The present invention fulfills these needs and provides further related advantages.

SUMMARY OF THE INVENTION

The present disclosure is based, in part, on methods of determining or predicting the presence or absence of one or more infectious disease agents in a subject of known or unknown infection status through immunological quantification techniques combined with mathematical modeling.

The present disclosure provides a method of predicting the presence or absence of an infection in a subject of unknown infection status. In one embodiment, the genomic DNA of a sample comprising T cells obtained from the subject is subjected to amplification and high throughput sequencing to determine a T cell receptor (TCR) profile comprising unique TCR complementarity determining region 3 (CDR3) amino acid sequences. In a particular embodiment, the TCR profile is then compared against a database of previously identified diagnostic public T cell receptor sequences that are known to be statistically significantly associated with the infection. In one embodiment, a first score for the subject is then generated by determining the proportion of unique TCR sequences in the profile of the subject that match the public TCR sequences in the database. In this embodiment, the first score is input into an algorithm that compares the first score of the subject with the known infection statuses of a plurality of subjects of known infection status. In a further embodiment, an estimated probability of infection status is then determined for the subject as the algorithm output. In some embodiments, the method further comprises an initial step of obtaining a sample comprising T cells from the subject.

In particular embodiments, the present disclosure additionally provides a method of predicting the presence or absence of one or more viral infections in a subject of unknown infection status. In a further embodiment, the method comprises determining a profile of unique TCR sequences from a sample obtained from the subject (e.g., a sample comprising T cells), and inputting these unique TCR sequences into one or more algorithms. In one embodiment, the one or more algorithms are generated by determining at least 100,000 unique TCR sequences from each of a plurality of subjects of known infection status for each of the one or more infections. In some embodiments, the method further comprises an initial step of obtaining a sample from the subject. In some embodiments, unique TCR sequences are statistically identified that correlate with the presence or absence of each of the one or more infections, thus generating a score which is predictive of the presence or absence of each of the one or more infections. In these embodiments, the scores are then input into a logistic regression model trained on each of the plurality of subjects of known infection status for each of the one or more infections, the output of which is the prediction as to whether the subject is either positive or negative for each of the one or more infections.

In some embodiments the one or more infections are from a cytomegalovirus (CMV), an Epstein-Barr virus (EBV), a Herpes simplex virus (HSV) or a small pox virus.

In particular embodiments, the present disclosure also provides a method for predicting the presence or absence of a CMV infection in a subject of unknown infection status. In one embodiment, the genomic DNA of a sample comprising T cells obtained from a subject is subjected to amplification and high throughput sequencing to determine a TCR profile comprising unique CDR3 amino acid sequences. In some embodiments, the method further comprises an initial step of obtaining a sample comprising T cells from the subject. In further embodiments, the TCR profile is then compared against a database of previously identified diagnostic public T cell receptor sequences that known to be statistically significantly associated with CMV infection. In some embodiments, a CMV burden score for the subject is then generated by determining the proportion of unique TCR sequences in the profile of the subject that match the public TCR sequences in the database. In further embodiments, the calculated CMV burden score is input into a logistic regression model that compares CMV burden and CMV infection status from a plurality of subjects of known CMV infection status. In one embodiment, an estimated probability of CMV infection status is then determined for the subject as the logistic regression model output.

In some embodiments, the database of public T cell sequences are determined to be statistically associated by obtaining unique TCR sequences from a group of subjects with CMV infection and a group of subjects without CMV infection. In one embodiment, each unique TCR sequence is subjected to a one-tailed Fisher exact test based on the presence or absence of each TCR sequence in subjects of known CMV infection status. In one embodiment, the null hypothesis being that each TCR sequence is no more common in subjects with a CMV infection than in subjects without a CMV infection. In one embodiment, a nominal p value threshold is set, and the false discovery rate (FDR) is controlled by permutation of CMV infection status in each subject to generate an empirical null distribution of p-values. In a particular embodiment, a database is then generated that comprises T cell receptor sequences that are statistically significantly shared in subjects with CMV infection.

In some embodiments, the nominal p-value threshold is less than or equal to $1.0*10^{-4}$.

In some embodiments, the statistically identified unique TCR sequences that correlate with the presence or absence of CMV infection comprise one or more of SEQ ID NOs: 1 to 142. In some embodiments, the statistically identified unique TCR sequences that correlate with the presence or absence of CMV infection comprise SEQ ID NOs: 1 to 142.

In some embodiments, the step of determining the at least 100,000 unique TCRβ sequences from the sample includes amplifying the rearranged nucleic acids encoding the TCRβ CDR3 region in a multiplex PCR reaction with a mixture of forward primers specific to TCR Vβ gene segments and reverse primers specific to TCR Jβ gene segments. In some embodiments, the reads of the amplified nucleic acids are sequenced, and the sequence reads are processed to remove errors in the primary sequence of each read and to compress the data. In particular embodiments, a nearest neighbor algorithm is applied to collapse the data into unique sequences by merging closely related sequences to remove both PCR and sequencing errors.

The method also includes determining an HLA association for each unique TCR sequence in the TCR profile. In some embodiments, the unique TCR sequence is associated with an HLA-A and/or an HLA-B allele.

The method of the invention also comprises steps for predicting a human leukocyte antigen (HLA) allele status of a subject, comprising (a) determining an immune receptor profile of unique T-cell receptor (TCR) rearranged DNA sequences for each of a plurality of subjects, each subject having a known HLA allele status; (b) categorizing the plurality of subjects based on (i) said known HLA allele status of the subject and (ii) a presence or absence in the subject's immune receptor profile of a feature comprising a unique TCR rearranged DNA sequence; (c) determining a statistical score for the association between a set of features and a positive HLA allele status based on (b); (d) training a machine learning model using said set of features to define a set of classifiers for each HLA allele status; (e) inputting one or more unique TCR rearranged DNA sequences of a subject with an unknown HLA allele status into said machine learning model to identify one or more features that match the set of classifiers; and (f) predicting an HLA allele status of said subject based on said one or more matched features.

The method comprises determining an immune receptor profile by determining the total number of unique TCR sequences and the frequency of each unique TCR sequence. The method also comprises determining a statistical score comprising determining a p-value using a Fisher exact two-tailed test.

In some embodiments, the method includes determining a cutoff p-value for identifying a set of features that are significantly associated with an HLA allele status. In another embodiment, the method includes determining a false discovery rate (FDR) of the association of a feature with an HLA allele status. In other embodiments, the method includes determining a number of false-positive associations between said feature and said HLA allele status.

In some embodiments, the method includes training a machine learning model by training a logistic regression model using said set of identified features and said known HLA allele statuses of each subject. In one embodiment, the method includes training a machine learning model comprises performing a leave-one out cross validation method. In another embodiment, the method comprises performing said leave-one out cross validation method for multiple rounds. In another embodiment, the prediction is at least 80% accurate or is at least 90% accurate.

In certain embodiments, the TCR rearranged DNA sequence is a TCRA, TCRB, TCRG or TCRD rearranged DNA sequence. In other embodiments, the HLA allele is a HLA-A2 allele or a HLA-24 allele.

BRIEF DESCRIPTION OF THE DRAWINGS

A better understanding of the novel features of the invention and advantages of the present invention will be obtained by reference to the following description that sets forth illustrative embodiments, in which the principles of the invention are utilized, and the accompanying drawings of which:

Figure (FIG. 1 depicts eleven distinct CDR3β VDJ recombination events, while still yielding the same nucleotide sequence, and ultimately the same CDR3β amino acid sequence (SEQ ID NO:149). The nucleotide sequences on the left side of FIG. 1 are, in order from top to bottom, SEQ ID NO:143, SEQ ID NO: 144, SEQ ID NO: 144, SEQ ID NO: 144, SEQ ID NO: 144, SEQ ID NO: 144, SEQ ID NO:145, SEQ ID NO:146, SEQ ID NO:146, SEQ ID NO:147, SEQ ID NO:148.

FIG. 2A shows a dataset of peripheral blood samples from 640 healthy subjects (287 CMV- and 353 CMV+), which were analyzed by high-throughput TCR immune receptor profiling. In FIG. 2B, unique TCRβ sequences were identified that were present in significantly more CMV+ subjects than CMV-subjects, controlling for false determination rate (FDR) by permutation of CMV status. Presence of these CMV-associated TCRβ sequences was used to build a classification model. The top panel of FIG. 2B depicts CASSLIGVSSYNEQFF (SEQ ID NO:12). In FIG. 2C, the classification model was tested using an exhaustive leave-one-out cross-validation, in which one sample was held out of the calculations, and the process was repeated from the beginning. The resulting classification model was used to predict the CMV status of the holdout subject.

FIG. 3B shows demographic characteristics of the subjects included in this study, classified by CMV status.

FIG. 7 depicts CASSLIGVSSYNEQFF (SEQ ID NO:12).

FIG. 8 (top graph) shows data for the classification performance of all and the cross-validation (CV) datasets for each p-value threshold, measured as the area under the ROC curve (AUROC). The number above each set of data points corresponds to the number of CMV-associated TCRβ identified at that p-value threshold, and the rectangle indicates the dataset selected for downstream analysis (p-value=$10^{-4}$). FIG. 8 (bottom graph) also shows a false discovery rate (FDR) estimated for each p-value threshold used in the identification of significantly CMV-associated TCRβ sequences, using permutations of CMV status. The best performance is seen at a p-value of $10^{-4}$, which corresponds to an estimated FDR of ~20%, resulting in the identification of a set of 142 TCRβ sequences that were significantly associated with positive CMV status (listed in Table 1).

FIG. 10A shows the distribution of HLA-A alleles in this cohort. FIG. 10B shows the distribution of HLA-B alleles in this cohort. FIGS. 10A and 10B depict the following sequences:

CASSLAPGATNEKLFF, (SEQ ID NO: 8)

CASSLIGVSSYNEQFF, (SEQ ID NO: 12)

CASSPSRNTEAFF, (SEQ ID NO: 73)

CASSLQAGANEQFF, (SEQ ID NO: 119) and

CASASANYGYTF. (SEQ ID NO: 118)

Figure 11:
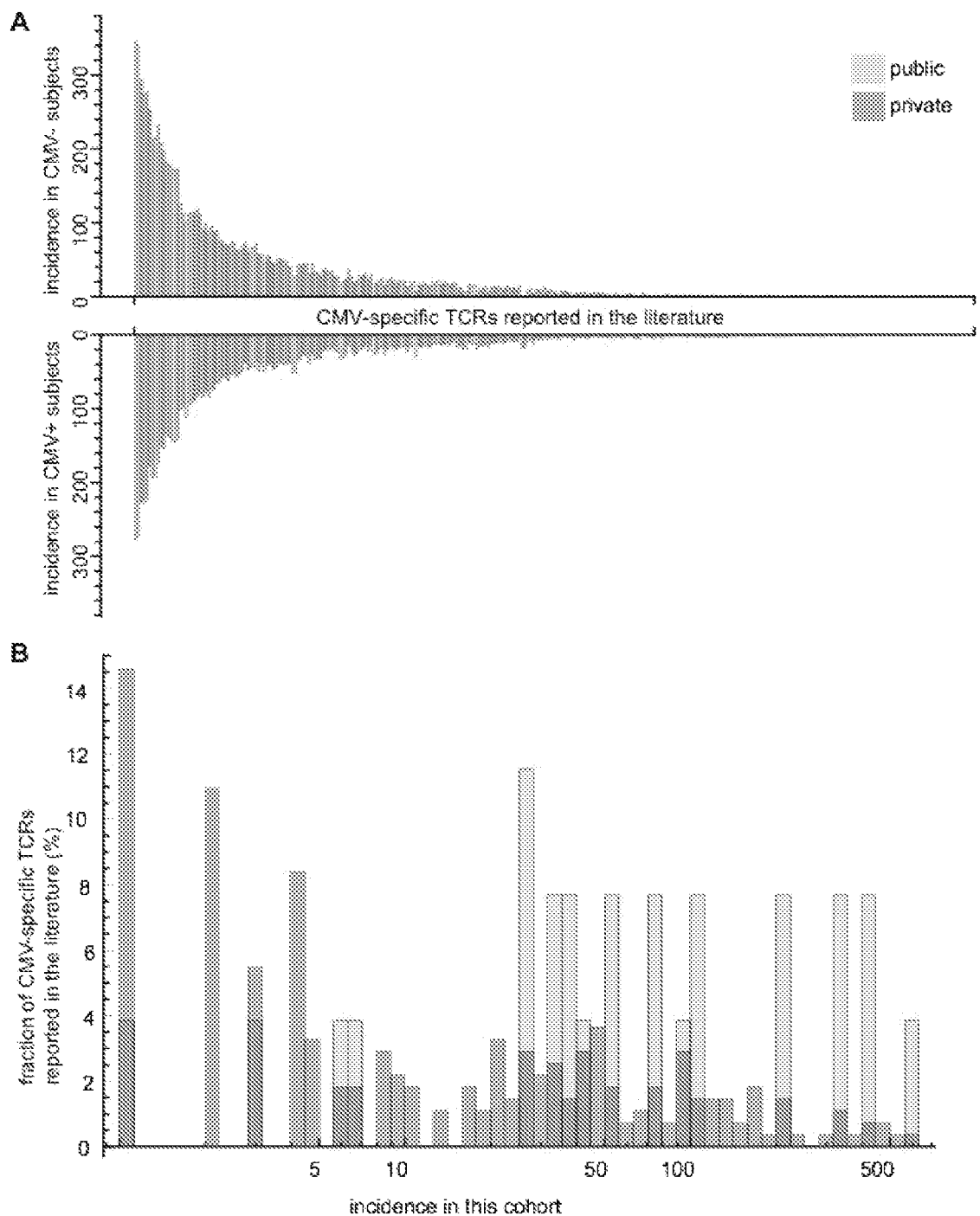

FIGS. 11A and 11B show the incidence of previously reported CMV-reactive TCRβ sequences in this cohort. FIG. 11A shows the incidence of each such TCRβ sequence in the cohort of 640 subjects plotted along the horizontal axis by decreasing total incidence, with the incidence in CMV+ subjects above the horizontal and the incidence in CMV− subjects below the horizontal. FIG. 11B shows a histogram of incidence of these TCRβ sequences in the cohort of 640 subjects plotted for each group of sequences.

FIG. 12 shows the concordance of TCRβ sequences in the cohort as compared to those in the literature. FIG. 12 depicts the following sequences: CASSLAPGATNEKLFF (SEQ ID NO:8), CASSLIGVSSYNEQFF (SEQ ID NO:12), CASSPSRNTEAFF (SEQ ID NO:73), CASSLQAGANEQFF (SEQ ID NO:119), and CASASANYGYTF (SEQ ID NO:118).

Figure 13:
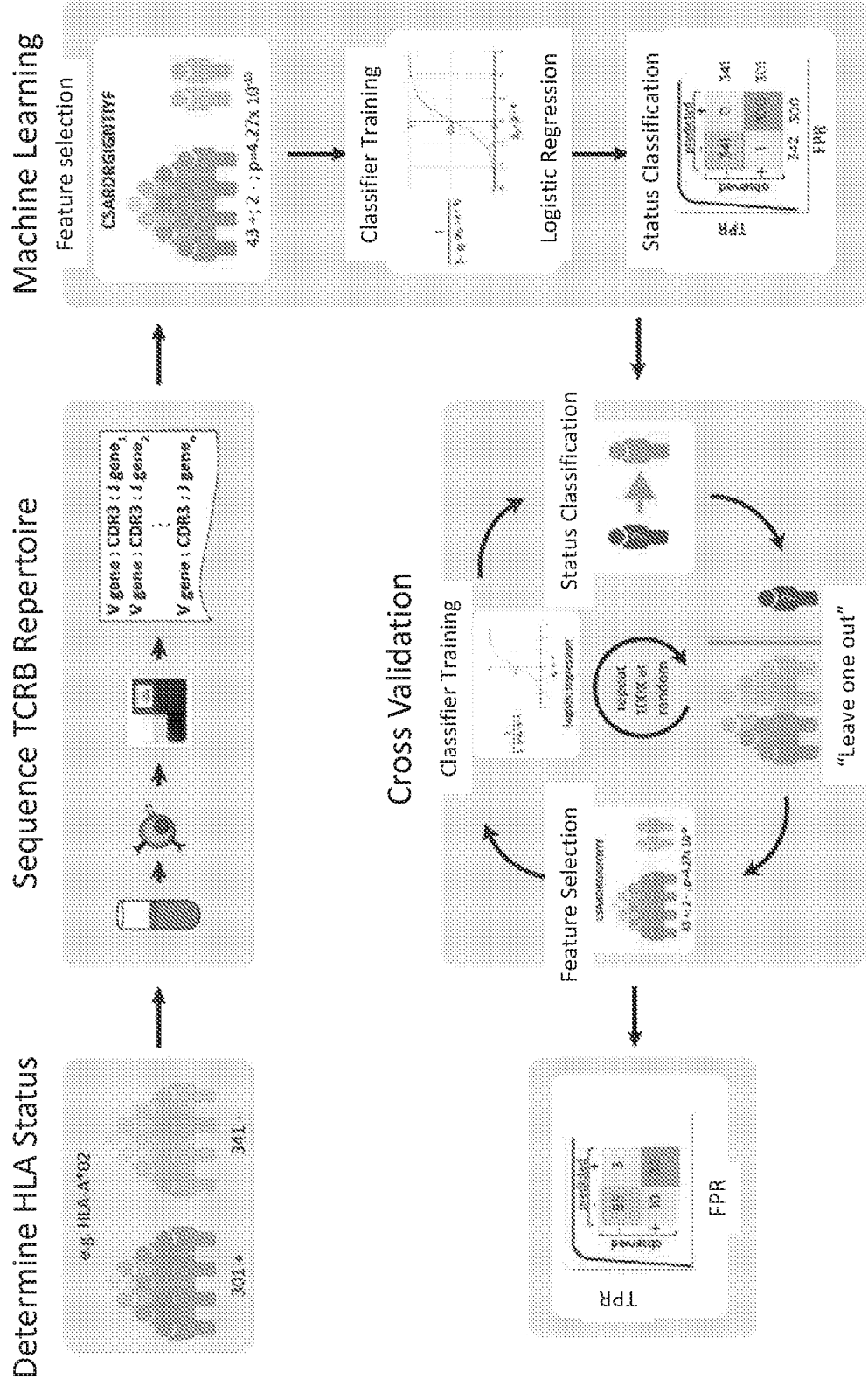

FIG. 13 depicts an overview of one embodiment of the method. FIG. 13 depicts CSARDRGIGNTIYF (SEQ ID NO:152).

Figure 14:
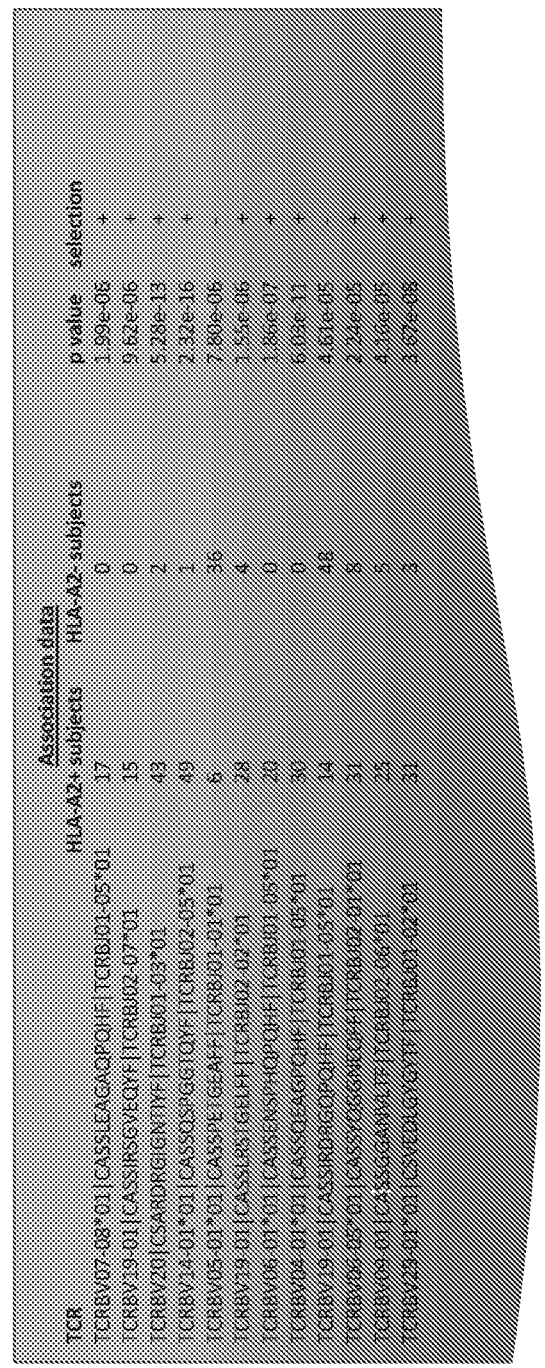

FIG. 14 depicts feature selection using a two-tailed Fisher exact test to determine statistical significance of the association between a feature (unique TCRβ sequence) and HLA allele status (HLA-A2+ or HLA-A2-), according to an embodiment of the invention. An exemplary list is shown of features (unique TCRβ sequences) and the number of subjects who have a particular feature and whether the subject is positive or negative for the HLA-A2 allele. FIG. 14 depicts, in order from top to bottom, SEQ ID NOs:150-161.

Figure 15:
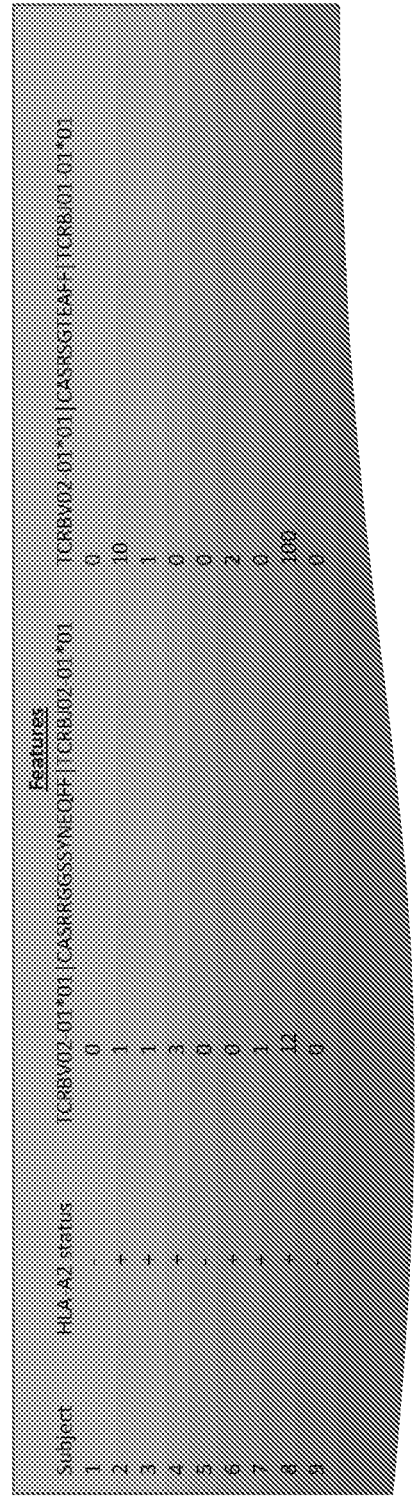

FIG. 15 depicts steps for feature selection, according to an embodiment of the invention. A p value is selected as a cutoff for identifying a set of "Feature TCRs" from the entire list of possible TCR sequences. Defining a p-value threshold and permuting the allele status across individuals provides an estimate of false discovery rate. This is performed for each HLA allele, resulting in a set of allele-associated TCRβ sequences for each HLA allele. A p value cutoff of $p \leq 10^{-4}$ and an FDR of 0.1 was used to identify 288 TCRβ sequences that are positively associated with HLA-A2. For each of the allele-associated TCRβ sequences, the frequency of the sequence is also determined in each subject. FIG. 15 depicts, in order from left to right, SEQ ID NOs:162 and 163.

Figure 16:
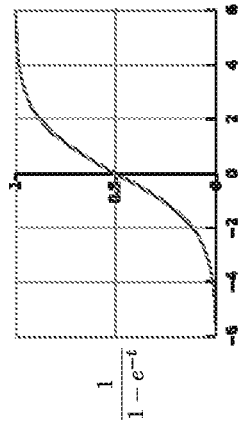

FIG. 16 depicts a machine learning process for fitting a logistic regression model, according to an embodiment of the invention.

FIG. 17 depicts an exhaustive leave-one-out cross validation, according to an embodiment of the invention.

Figure 18:
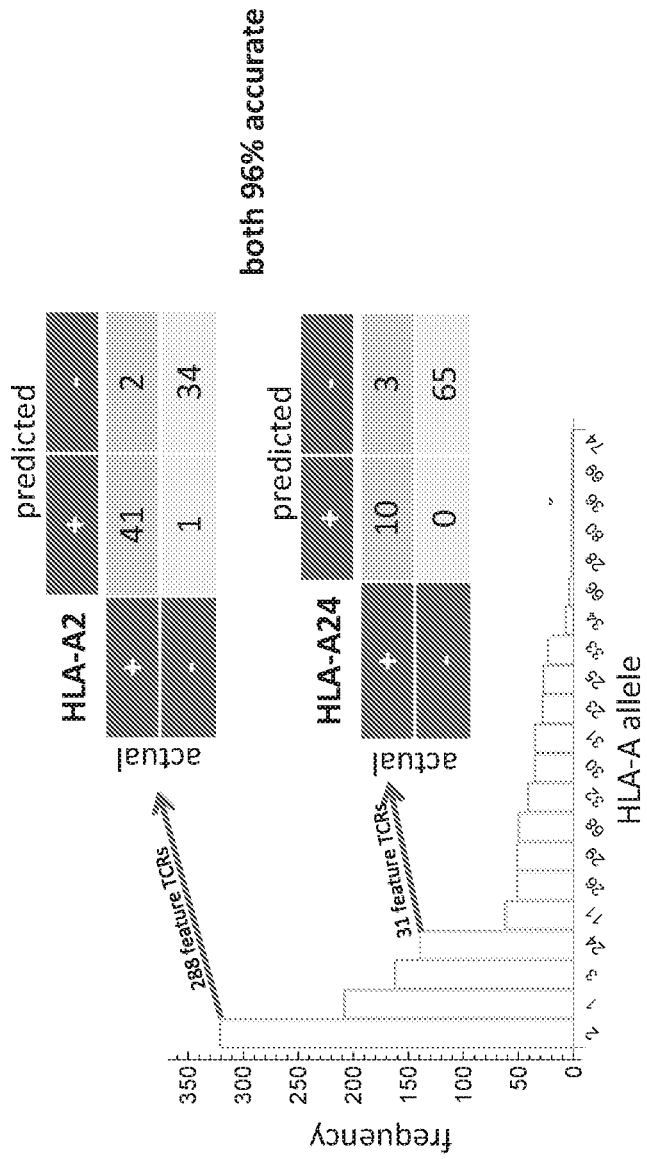

FIG. 18 shows the results of the cross-validation experiment and illustrates the accuracy of the method.

DETAILED DESCRIPTION OF THE INVENTION

The invention provides methods for predicting and diagnosing infectious disease in a subject that are disease-specific (specific for each particular disease state), have a universal platform (do not require different processes/reagents for each disease state), and multiplexed (are able to assay multiple disease states simultaneously).

In one embodiment, the method includes steps for high-throughput immunosequencing of rearranged TCR genes in healthy subjects with known CMV status. Using the immunosequencing results, the method includes searching for TCRβ sequences that are present in multiple subjects, and identifying a set of TCRβ sequences that are significantly associated with positive CMV status. The method also includes calculating a p-value for the association of each TCRβ sequence with CMV status using a Fisher exact test, controlling the false discovery rate (FDR) by permutation of the CMV status, and identifying a list of CMV-associated TCRβ sequences (for a certain FDR and p-value). A CMV score is calculated for each subject as the proportion of all that subject's TCRβ sequences that are represented in the catalog of CMV-associated TCRβ sequences. The CMV score is used to distinguish between CMV+ and CMV− subjects.

Infectious agents include pathogens, viruses, bacteria, parasites and/or microorganisms. In some embodiments, viruses include, but are not limited to, members of the herpes virus family (such as herpes simplex viruses 1 and 2, varicella-zoster virus, EBV (Epstein-Barr virus), human cytomegalovirus (CMV), human herpesvirus 6, human herpesvirus 7, and Kaposi's sarcoma-associated herpesvirus), Hepatitis B virus (HBV), Hepatitis C virus (HCV), human immunodeficiency viruses (HIV) I and II, influenza A virus, influenza B virus, respiratory syncytial viruses (RSV) A and B, and human metapneumovirus (MPV). Other examples include human T-cell lymphocytotrophic virus, human papillomaviruses, orthomyxo viruses, paramyxo viruses, adenoviruses, corona viruses, rhabdo viruses, polio viruses, toga viruses, bunya viruses, arena viruses, rubella viruses, reo viruses, Norovirus, human metapneumovirus (MPV), West Nile virus, Yellow fever virus, Rabies virus, Rhinovirus, Rift Valley fever virus, Marburg virus, mumps virus, measles virus, human papilloma virus (HPV), Ebola virus, Colorado tick fever virus (CTFV), and/or rhinoviruses.

Other infectious organisms include *Escherichia coli, Salmonella, Shigella, Campylobacter, Klebsiella, Pseudomonas, Listeria monocytogenes, Mycobacterium tuberculosis, Mycobacterium avium-intracellulare, Yersinia, Francisella, Pasteurella, Brucella, Clostridia, Bordetella pertussis, Bacteroides, Staphylococcus aureus, Streptococcus pneumonia*, B-Hemolytic strep., *Corynebacteria, Legionella, Mycoplasma, Ureaplasma, Chlamydia, Clostridium difficile, Gardnerella, Trichomonas vaginalis, Neisseria gonorrhea, Neisseria meningitides, Hemophilus influenza, Enterococcus faecalis, Proteus vulgaris, Proteus mirabilis, Helicobacter pylori, Treponema palladium, Borrelia burgdorferi, Borrelia recurrentis, Rickettsial pathogens, Nocardia, Acitnomycetes* and/or *Acinetobacter*.

In still other embodiments, fungal infectious agents include, but are not limited to, *Cryptococcus neoformans, Blastomyces dermatitidis, Histoplasma capsulatum, Coccidioides immitis, Paracoccicioides brasiliensis, Candida albicans, Aspergillus fumigautus, Phycomycetes (Rhizopus), Sporothrix schenckii, Chromomycosis*, and/or *Maduromycosis*.

In more embodiments, parasitic agents include, but are not limited to, *Plasmodium falciparum, Plasmodium malaria, Plasmodium vivax, Plasmodium ovale, Onchoverva volvulus, Leishmania, Trypanosoma* spp., *Schistosoma* spp., *Entamoeba histolytica, Cryptosporidium, Giardia* spp., *Trichimonas* spp., *Balatidium coli, Wuchereria bancrofti, Toxoplasma* spp., *Enterobius vermicularis, Ascaris lumbricoides, Trichuris trichiura, Dracunculus medinesis, trematodes, Diphyllobothrium latum, Taenia* spp., *Pneumocystis carinii*, and/or *Necator americans*.

The major histocompatibility complex (MHC) is a set of cell surface molecules encoded by a large gene family which controls a major part of the immune system in all vertebrates. The major function of major histocompatibility complexes is to bind to peptide fragments derived from pathogens and display them on the cell surface for recognition by the appropriate T-cells.

The major histocompatibility complex (MHC) contains two types of polymorphic MHC genes, the class I and class II genes, which encode two groups of structurally distinct but homologous proteins, and other nonpolymorphic genes whose products are involved in antigen presentation.

The human MHC is called human leukocyte antigen (HLA). HLA proteins are encoded by genes of the MHC. HLA class I antigens include HLA-A, HLA-B, and HLA-C. HLA class II antigens include HLA-DR, HLA-DQ, HLA-DP, HLA-DM, HLA-DOA, HLA-DOB. HLA's corresponding to MHC class I (A, B, and C) present peptides from inside the cell. HLA's corresponding to MHC class II (DP, DM, DOA, DOB, DQ, and DR) present antigens from outside of the cell to T-lymphocytes. MHC molecules mediate the binding of a given T cell receptor to a given antigen, so MHC polymorphism across individuals modulates the T cell response to a given antigen. Clinical applications of HLA typing include vaccine trials, disease associations, adverse drug reactions, platelet transfusion, and transplantation of organs and stem cells.

There are numerous alleles at each HLA gene locus (A1, A2, A3, etc.). Each person inherits one complete set of HLA alleles (haplotype) from each parent, and this combination of encoded proteins constitutes a person's HLA type (e.g., different antigens of A23, A31, B7, B44, C7, C8, DR4, DR7, DQ2, DQ7, DP2, DP3). There are more than 50,000 different known HLA types.

As used herein, adaptive immune receptor (AIR) refers to an immune cell receptor, e.g., a T cell receptor (TCR) or an Immunoglobulin (Ig) receptor found in mammalian cells. In certain embodiments, the adaptive immune receptor is encoded by a TCRB, TCRG, TCRA, TCRD, IGH, IGK, and IGL gene or gene segment.

The term "primer," as used herein, refers to an oligonucleotide sequence capable of acting as a point of initiation of DNA synthesis under suitable conditions. Such conditions include those in which synthesis of a primer extension product complementary to a nucleic acid strand is induced in the presence of four different nucleoside triphosphates and an agent for extension (e.g., a DNA polymerase or reverse transcriptase) in an appropriate buffer and at a suitable temperature.

As used herein, the term "gene" refers to the segment of DNA involved in producing a polypeptide chain, such as all or a portion of a TCR or Ig polypeptide (e.g., a CDR3-containing polypeptide); it includes regions preceding and following the coding region "leader and trailer" as well as intervening sequences (introns) between individual coding segments (exons), and can also include regulatory elements (e.g., promoters, enhancers, repressor binding sites and the like), and can also include recombination signal sequences (RSSs), as described herein.

The nucleic acids of the present embodiments, also referred to herein as polynucleotides, and including oligonucleotides, can be in the form of RNA or in the form of DNA, including cDNA, genomic DNA, and synthetic DNA. The DNA can be double-stranded or single-stranded, and if single stranded can be the coding strand or non-coding (anti-sense) strand. A coding sequence which encodes a TCR or an immunoglobulin or a region thereof (e.g., a V region, a D segment, a J region, a C region, etc.) for use according to the present embodiments can be identical to the coding sequence known in the art for any given TCR or immunoglobulin gene regions or polypeptide domains (e.g., V-region domains, CDR3 domains, etc.), or can be a different coding sequence, which, as a result of the redundancy or degeneracy of the genetic code, encodes the same TCR or immunoglobulin region or polypeptide.

Unless specific definitions are provided, the nomenclature utilized in connection with, and the laboratory procedures and techniques of, molecular biology, analytical chemistry, synthetic organic chemistry, and medicinal and pharmaceutical chemistry described herein are those well-known and commonly used in the art. Standard techniques can be used for recombinant technology, molecular biological, microbiological, chemical syntheses, chemical analyses, pharmaceutical preparation, formulation, and delivery, and treatment of patients.

Unless the context requires otherwise, throughout the present specification and claims, the word "comprise" and variations thereof, such as, "comprises" and "comprising" are to be construed in an open, inclusive sense, that is, as "including, but not limited to." By "consisting of" is meant including, and typically limited to, whatever follows the phrase "consisting of" By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are required and can or cannot be present depending upon whether or not they affect the activity or action of the listed elements.

In this specification and the appended claims, the singular forms "a," "an" and "the" include plural references unless the content clearly dictates otherwise.

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics can be combined in any suitable manner in one or more embodiments.

Methods of the Invention

Cells

A sample containing lymphoid nucleic acid molecules (genomic DNA, cDNA or alternatively, messenger RNA) from a subject can be obtained. The subject is a mammalian subject, such as a human.

Lymphocytes (B cells and/or T cells) can be obtained from a biological sample, such as from a variety of tissue and biological fluid samples. These include but are not limited to bone marrow, thymus, lymph glands, lymph nodes, peripheral tissues and blood, or solid tissue samples. Any peripheral tissue can be sampled for the presence of B and T cells and is therefore contemplated for use in the methods described herein. Peripheral blood mononuclear cells (PBMC) are isolated by techniques known to those of skill in the art, e.g., by Ficoll-Hypaque® density gradient separation. In certain embodiments, whole PBMCs are used for analysis.

Nucleic Acid Extraction

Total genomic DNA can be extracted from cells by methods known to those of skill in the art. Examples include using the QIAamp® DNA blood Mini Kit (QIAGEN®) or a Qiagen DNeasy Blood extraction Kit (Qiagen, Gaithersburg, Md., USA). The approximate mass of a single haploid genome is 3 pg. Preferably, at least 100,000 to 200,000 cells are used for analysis of diversity, i.e., about 0.6 to 1.2 µg DNA from diploid T cells. Using PBMCs as a source, the number of T cells can be estimated to be about 30% of total cells. Alternatively, total nucleic acid can be isolated from cells, including both genomic DNA and mRNA. In other embodiments, cDNA is transcribed from mRNA and then used as templates for amplification.

Multiplex Quantitative PCR

Multiplex quantitative PCR was performed as described herein and in Robins et al., 2009 *Blood* 114, 4099; Robins et al., 2010 *Sci. Translat. Med.* 2:47ra64; Robins et al., 2011 *J. Immunol. Meth.* doi:10.1016/jim.2011.09. 001; Sherwood et al. 2011 *Sci. Translat. Med.* 3:90ra61; US 2012/0058902, US 2010/0330571, WO/2010/151416, WO/2011/106738 (PCT/US2011/026373), US 2015/0299785, WO2012/027503 (PCT/US2011/049012), US 2013/0288237, U.S. Pat. Nos. 9,181,590, 9,181,591, and US 2013/0253842, which are incorporated by reference in their entireties. The present methods involve a multiplex PCR method using a set of forward primers that specifically hybridize to V segments and a set of reverse primers that specifically hybridize to the J segments of a TCR or Ig locus, where a multiplex PCR reaction using the primers allows amplification of all the possible VJ (and VDJ) combinations within a given population of T or B cells.

Exemplary V segment primers and J segment primers are described in US 2012/0058902, US 2010/033057, WO/2010/151416, WO/2011/106738 (PCT/US2011/026373), US 2015/0299785, WO2012/027503 (PCT/US2011/049012), US 2013/0288237, U.S. Pat. Nos. 9,181,590, 9,181,591, US 2013/0253842, WO 2013/188831 (PCT/US2013/045994), which are incorporated by reference in their entireties.

A multiplex PCR system can be used to amplify rearranged adaptive immune cell receptor loci. In certain embodiments, the CDR3 region is amplified from a TCRA, TCRB, TCRG or TCRD CDR3 region or similarly from an IgH or IgL (lambda or kappa) locus. A plurality of V-segment and J-segment primers are used to amplify substantially all (e.g., greater than 90%, 91%, 92%, 93%, 94%, 95%, 96%, 97%, 98% or 99%) rearranged adaptive immune receptor CDR3-encoding regions to produce a multiplicity of amplified rearranged DNA molecules. In certain embodiments, primers are designed so that each amplified rearranged DNA molecule is less than 600 nucleotides in length, thereby excluding amplification products from non-rearranged adaptive immune receptor loci.

In some embodiments, two pools of primers are used in a single, highly multiplexed PCR reaction. The "forward" pool of primers can include a plurality of V segment oligonucleotide primers and the reverse pool can include a plurality of J segment oligonucleotide primers. In some embodiments, there is a primer that is specific to (e.g., having a nucleotide sequence complementary to a unique sequence region of) each V region segment and to each J region segment in the respective TCR or Ig gene locus. In other embodiments, a primer can hybridize to one or more V segments or J segments, thereby reducing the number of primers required in the multiplex PCR. In certain embodiments, the J-segment primers anneal to a conserved sequence in the joining ("J") segment.

Each primer can be designed such that a respective amplified DNA segment is obtained that includes a sequence portion of sufficient length to identify each J segment unambiguously based on sequence differences amongst known J-region encoding gene segments in the human genome database, and also to include a sequence portion to which a J-segment-specific primer can anneal for resequencing. This design of V- and J-segment-specific primers enables direct observation of a large fraction of the somatic rearrangements present in the adaptive immune receptor gene repertoire within an individual.

In one embodiment, the present disclosure provides a plurality of V-segment primers and a plurality of J-segment primers. The plurality of V-segment primers and the plurality of J-segment primers amplify all or substantially all combinations of the V- and J-segments of a rearranged immune receptor locus. In some embodiments, the method provides amplification of substantially all of the rearranged AIR sequences in a lymphoid cell and is capable of quantifying the diversity of the TCR or IG repertoire of at least $10^6$, $10^5$, $10^4$, or $10^3$ unique rearranged AIR sequences in a sample. "Substantially all combinations" can refer to at least 80%, 85%, 90%, 91%, 92%, 93%, 94%, 95%, 96%, 97%, 98%, 99% or more of all the combinations of the V- and J-segments of a rearranged immune receptor locus. In certain embodiments, the plurality of V-segment primers and the plurality of J-segment primers amplify all of the combinations of the V- and J-segments of a rearranged immune receptor locus.

In general, a multiplex PCR system can use 2, 3, 4, 5, 6, 7, 8, 9, 10, 11, 12, 13, 14, 15, 16, 17, 18, 19, 20, 21, 22, 23, 24, or 25, and in certain embodiments, at least 26, 27, 28, 29, 30, 31, 32, 33, 34, 35, 36, 37, 38, or 39, and in other embodiments 40, 41, 42, 43, 44, 45, 46, 47, 48, 49, 50, 51, 52, 53, 54, 55, 56, 57, 58, 59, 60, 65, 70, 75, 80, 85, or more forward primers, in which each forward primer specifically hybridizes to or is complementary to a sequence corresponding to one or more V region segments. The multiplex PCR system also uses at least 2, 3, 4, 5, 6, or 7, and in certain embodiments, 8, 9, 10, 11, 12 or 13 reverse primers, or 14, 15, 16, 17, 18, 19, 20, 21, 22, 23, 24, or 25 or more primers, in which each reverse primer specifically hybridizes to or is complementary to a sequence corresponding to one or more J region segments. Various combinations of V and J segment primers can be used to amplify the full diversity of TCR and IG sequences in a repertoire. For details on the multiplex PCR system, including primer oligonucleotide sequences for amplifying TCR and IG sequences, see, e.g., Robins et al., 2009 *Blood* 114, 4099; Robins et al., 2010 *Sci. Translat. Med.* 2:47ra64; Robins et al., 2011 *J. Immunol. Meth.* doi:10.1016/j.jim.2011.09. 001; Sherwood et al. 2011 *Sci. Translat. Med.* 3:90ra61; US 2012/0058902, US 2010/033057, WO/2010/151416, WO/2011/106738 (PCT/US2011/026373), US 2015/0299785, WO2012/027503 (PCT/US2011/049012), US 2013/0288237, U.S. Pat. Nos. 9,181,590, 9,181,591, US 2013/0253842, WO 2013/188831 (PCT/US2013/045994), which is each incorporated by reference in its entirety.

Oligonucleotides or polynucleotides that are capable of specifically hybridizing or annealing to a target nucleic acid sequence by nucleotide base complementarity can do so under moderate to high stringency conditions. In one embodiment, suitable moderate to high stringency conditions for specific PCR amplification of a target nucleic acid sequence can be between 25 and 80 PCR cycles, with each cycle consisting of a denaturation step (e.g., about 10-30 seconds (s) at greater than about 95° C.), an annealing step (e.g., about 10-30 s at about 60-68° C.), and an extension step (e.g., about 10-60 s at about 60-72° C.), optionally according to certain embodiments with the annealing and extension steps being combined to provide a two-step PCR. As would be recognized by the skilled person, other PCR reagents can be added or changed in the PCR reaction to increase specificity of primer annealing and amplification, such as altering the magnesium concentration, optionally adding DMSO, and/or the use of blocked primers, modified nucleotides, peptide-nucleic acids, and the like.

A primer is preferably a single-stranded DNA. The appropriate length of a primer depends on the intended use of the primer but typically ranges from 6 to 50 nucleotides, or in certain embodiments, from 15-35 nucleotides in length. Short primer molecules generally require cooler temperatures to form sufficiently stable hybrid complexes with the template. A primer need not reflect the exact sequence of the template nucleic acid, but must be sufficiently complementary to hybridize with the template. The design of suitable primers for the amplification of a given target sequence is well known in the art and described in the literature cited herein.

In some embodiments, the V- and J-segment primers are used to produce a plurality of amplicons from the multiplex PCR reaction. In certain embodiments, the amplicons range in size from 10, 20, 30, 40, 50, 75, 100, 200, 300, 400, 500, 600, 700, 800 or more nucleotides in length. In preferred embodiments, the amplicons have a size between 50-600 nucleotides in length.

According to non-limiting theory, these embodiments exploit current understanding in the art (also described above) that once an adaptive immune cell (e.g., a T or B lymphocyte) has rearranged its adaptive immune receptor-encoding (e.g., TCR or Ig) genes, its progeny cells possess the same adaptive immune receptor-encoding gene rearrangement, thus giving rise to a clonal population (clones) that can be uniquely identified by the presence therein of rearranged (e.g., CDR3-encoding) V- and J-gene segments that can be amplified by a specific pairwise combination of V- and J-specific oligonucleotide primers as herein disclosed.

In some embodiments, the V segment primers and J segment primers each include a second sequence at the 5'-end of the primer that is not complementary to the target V or J segment. The second sequence can comprise an oligonucleotide having a sequence that is selected from (i) a universal adaptor oligonucleotide sequence, and (ii) a sequencing platform-specific oligonucleotide sequence that is linked to and positioned 5' to a first universal adaptor oligonucleotide sequence. Examples of universal adaptor oligonucleotide sequences can be pGEX forward and pGEX reverse adaptor sequences.

In some embodiments, the resulting amplicons using the V-segment and J-segment primers described above include amplified V and J segments and the universal adaptor oligonucleotide sequences. The universal adaptor sequence can be complementary to an oligonucleotide sequence found in a tailing primer. Tailing primers can be used in a second PCR reaction to generate a second set of amplicons. In some embodiments, tailing primers can have the general formula:

$$5'\text{-P--S--B--U-}3' \tag{III}$$

wherein P comprises a sequencing platform-specific oligonucleotide, wherein S comprises a sequencing platform tag-containing oligonucleotide sequence;

wherein B comprises an oligonucleotide barcode sequence and wherein said oligonucleotide barcode sequence can be used to identify a sample source, and wherein U comprises a sequence that is complementary to the universal adaptor oligonucleotide sequence or is the same as the universal adaptor oligonucleotide sequence.

Additional description about universal adaptor oligonucleotide sequences, barcodes, and tailing primers are found in WO 2013/188831 (PCT/US13/45994), which is incorporated by reference in its entirety.

Amplification Bias Control

Multiplex PCR assays can result in a bias in the total numbers of amplicons produced from a sample, given that certain primer sets are more efficient in amplification than others. To overcome the problem of such biased utilization of subpopulations of amplification primers, methods can be used that provide a template composition for standardizing the amplification efficiencies of the members of an oligonucleotide primer set, where the primer set is capable of amplifying rearranged DNA encoding a plurality of adaptive immune receptors (TCR or Ig) in a biological sample that comprises DNA from lymphoid cells.

In some embodiments, a template composition is used to standardize the various amplification efficiencies of the primer sets. The template composition can comprise a plurality of diverse template oligonucleotides of general formula (I):

$$5'\text{-U1-B1-V-B2-R-J-B3-U2-}3' \tag{I}$$

The constituent template oligonucleotides are diverse with respect to the nucleotide sequences of the individual template oligonucleotides. The individual template oligonucleotides can vary in nucleotide sequence considerably from one another as a function of significant sequence variability among the large number of possible TCR or BCR variable (V) and joining (J) region polynucleotides. Sequences of individual template oligonucleotide species can also vary from one another as a function of sequence differences in U1, U2, B (B1, B2 and B3) and R oligonucleotides that are included in a particular template within the diverse plurality of templates.

In certain embodiments, V is a polynucleotide comprising at least 20, 30, 60, 90, 120, 150, 180, or 210, and not more than 1000, 900, 800, 700, 600 or 500 contiguous nucleotides of an adaptive immune receptor variable (V) region encoding gene sequence, or the complement thereof, and in each of the plurality of template oligonucleotide sequences V comprises a unique oligonucleotide sequence.

In some embodiments, J is a polynucleotide comprising at least 15-30, 31-60, 61-90, 91-120, or 120-150, and not more than 600, 500, 400, 300 or 200 contiguous nucleotides of an adaptive immune receptor joining (J) region encoding gene sequence, or the complement thereof, and in each of the plurality of template oligonucleotide sequences J comprises a unique oligonucleotide sequence.

U1 and U2 can be each either nothing or each comprise an oligonucleotide having, independently, a sequence that is selected from (i) a universal adaptor oligonucleotide sequence, and (ii) a sequencing platform-specific oligonucleotide sequence that is linked to and positioned 5' to the universal adaptor oligonucleotide sequence.

B1, B2 and B3 can be each either nothing or each comprise an oligonucleotide B that comprises a first and a second oligonucleotide barcode sequence of 3, 4, 5, 6, 7, 8, 9, 10, 11, 12, 13, 14, 15, 16, 17, 18, 19, 20, 25, 30, 35, 40, 45, 50, 60, 70, 80, 90, 100, 200, 300, 400, 500, 600, 700, 800, 900 or 1000 contiguous nucleotides (including all integer values therebetween), wherein in each of the plurality of template oligonucleotide sequences B comprises a unique oligonucleotide sequence in which (i) the first barcode sequence uniquely identifies the unique V oligonucleotide sequence of the template oligonucleotide and (ii) the second barcode sequence uniquely identifies the unique J oligonucleotide sequence of the template oligonucleotide.

R can be either nothing or comprises a restriction enzyme recognition site that comprises an oligonucleotide sequence that is absent from V, J, U1, U2, B1, B2 and B3.

Methods are used with the template composition for determining non-uniform nucleic acid amplification potential among members of a set of oligonucleotide amplification primers that are capable of amplifying productively rearranged DNA encoding one or a plurality of adaptive immune receptors in a biological sample that comprises DNA from lymphoid cells of a subject. The method can include the steps of: (a) amplifying DNA of a template composition for standardizing amplification efficiency of an oligonucleotide primer set in a multiplex polymerase chain reaction (PCR) that comprises: (i) the template composition (I) described above, wherein each template oligonucleotide in the plurality of template oligonucleotides is present in a substantially equimolar amount; (ii) an oligonucleotide amplification primer set that is capable of amplifying productively rearranged DNA encoding one or a plurality of adaptive immune receptors in a biological sample that comprises DNA from lymphoid cells of a subject.

The primer set can include: (1) in substantially equimolar amounts, a plurality of V-segment oligonucleotide primers that are each independently capable of specifically hybridizing to at least one polynucleotide encoding an adaptive immune receptor V-region polypeptide or to the complement thereof, wherein each V-segment primer comprises a nucleotide sequence of at least 15 contiguous nucleotides that is complementary to at least one functional adaptive immune receptor V region-encoding gene segment and wherein the plurality of V-segment primers specifically hybridize to substantially all functional adaptive immune receptor V region-encoding gene segments that are present in the template composition, and (2) in substantially equimolar amounts, a plurality of J-segment oligonucleotide primers that are each independently capable of specifically hybridizing to at least one polynucleotide encoding an adaptive immune receptor J-region polypeptide or to the complement thereof, wherein each J-segment primer comprises a nucleotide sequence of at least 15 contiguous nucleotides that is complementary to at least one functional adaptive immune receptor J region-encoding gene segment and wherein the plurality of J-segment primers specifically hybridize to substantially all functional adaptive immune receptor J region-encoding gene segments that are present in the template composition.

The V-segment and J-segment oligonucleotide primers are capable of promoting amplification in said multiplex polymerase chain reaction (PCR) of substantially all template oligonucleotides in the template composition to produce a multiplicity of amplified template DNA molecules, said multiplicity of amplified template DNA molecules being sufficient to quantify diversity of the template oligonucleotides in the template composition, and wherein each amplified template DNA molecule in the multiplicity of amplified template DNA molecules is less than 1000, 900, 800, 700, 600, 500, 400, 300, 200, 100, 90, 80 or 70 nucleotides in length.

The method also includes steps of: (b) sequencing all or a sufficient portion of each of said multiplicity of amplified template DNA molecules to determine, for each unique template DNA molecule in said multiplicity of amplified template DNA molecules, (i) a template-specific oligonucleotide DNA sequence and (ii) a relative frequency of occurrence of the template oligonucleotide; and (c) comparing the relative frequency of occurrence for each unique template DNA sequence from said template composition, wherein a non-uniform frequency of occurrence for one or more template DNA sequences indicates non-uniform nucleic acid amplification potential among members of the set of oligonucleotide amplification primers.

Further description about bias control methods are provided in US 2013/0253842, U.S. Pat. No. 9,150,905, US 2015/0203897, and WO 2013/169957 (PCT/US2013/040221), which are incorporated by reference in their entireties.

Sequencing

Sequencing can be performed using any of a variety of available high throughput single molecule sequencing machines and systems. Illustrative sequence systems include sequence-by-synthesis systems, such as the Illumina Genome Analyzer and associated instruments (Illumina HiSeq) (Illumina, Inc., San Diego, Calif.), Helicos Genetic Analysis System (Helicos BioSciences Corp., Cambridge, Mass.), Pacific Biosciences PacBio RS (Pacific Biosciences, Menlo Park, Calif.), or other systems having similar capabilities. Sequencing is achieved using a set of sequencing platform-specific oligonucleotides that hybridize to a defined region within the amplified DNA molecules. The sequencing platform-specific oligonucleotides are designed to sequence up amplicons, such that the V- and J-encoding gene segments can be uniquely identified by the sequences that are generated. See, e.g., US 2012/0058902; US 2010/033057; WO 2011/106738 (PCT/US2011/026373); US 2015/0299785; or WO 2012/027503 (PCT/US2011/049012), which is each incorporated by reference in its entirety.

In some embodiments, the raw sequence data is preprocessed to remove errors in the primary sequence of each read and to compress the data. A nearest neighbor algorithm can be used to collapse the data into unique sequences by merging closely related sequences, to remove both PCR and sequencing errors. See, e.g., US 2012/0058902; US 2010/033057; WO 2011/106738 (PCT/US2011/026373); US 2015/0299785; or WO 2012/027503 (PCT/US2011/049012), which is each incorporated by reference in its entirety.

PCR Template Abundance Estimation

To estimate the average read coverage per input template in the multiplex PCR and sequencing approach, a set of synthetic TCR (or BCR) templates (as described above) can be used, comprising each combination of Vβ and Jβ gene segments. These synthetic molecules can be those described in general formula (I) above, and in US 2013/0253842, U.S. Pat. No. 9,150,905, US 2015/0203897, and WO 2013/169957 (PCT/US2013/040221), which are incorporated by reference in their entireties.

These synthetic molecules can be included in each PCR reaction at very low concentration so that only some of the synthetic templates are observed. Using the known concentration of the synthetic template pool, the relationship between the number of observed unique synthetic molecules and the total number of synthetic molecules added to reaction can be simulated (this is very nearly one-to-one at the low concentrations that were used). The synthetic molecules allow calculation for each PCR reaction the mean number of sequencing reads obtained per molecule of PCR template, and an estimation of the number of T cells in the input material bearing each unique TCR rearrangement.

Discovery of Diagnostic Public T Cell Responses

Given a large population of subjects with and without a given infectious disease, public T cell responses diagnostic for the disease state can be determined by applying the following statistical method. An immune receptor repertoire of unique T cell receptor sequences is determined, using the methods described above, for a group of subjects who have been identified as having or not having an infectious disease, such as CMV or small pox. It is possible, then, to determine which of those T cell receptor sequences are significantly more common (i.e., present in more individuals) among subjects with the disease state than in subjects without the disease state. When a common TCR binds to an antigen, it is called a public T cell response. Public T cell responses are specific for a particular disease or antigen, are present in many individuals, and are encoded in a common format (specific rearranged receptor sequences) regardless of disease.

A one-tailed Fisher exact test is used, using presence or absence of T cell receptor sequence in question vs. with or without disease state to construct a 2×2 contingency table (shown below) and with FDR (false discovery rate) controlled using an empirical distribution of null p-values determined by permutations of disease state. Since many clones are unique to a single subject (and consequently unique to either the positive or negative disease status classes), it is vital to control false discovery rate in feature selection to avoid over-fitting to the many spurious associations of unique TCRβs with positive infectious disease status. This process generates a list of T cell receptor sequences significantly more common in subjects with the disease state of interest.

|  | Disease+ | Disease− |
| --- | --- | --- |
| clone i present | $n_{i+}$ | $n_{i-}$ |
| clone i not present | $N_+ - n_{i+}$ | $N_- - n_{i-}$ |

Use of Diagnostic Public T Cell Responses to Infer Disease Status

Given a large population of subjects with and without a given infectious disease, and given a list of diagnostic public T cell responses generated as described above, it is possible to infer disease status in a subject of unknown disease status.

First, a 'disease burden' or quantitative measure of the presence and/or abundance of said diagnostic public T cell responses is calculated for each subject (those with known status as well as the subject of unknown status). The disease burden or quantitative measure is the proportion of unique T cell receptor sequences in each subject that are among the list of diagnostic public T cell responses.

Once this measure has been calculated, it is then determined whether the subject of unknown status has a disease burden consistent with known subjects who have the disease state of interest or with known subjects who do not have the disease state of interest. Herein, the method of comparison is to train a logistic regression model of (disease burden vs. presence of disease state) in all subjects of known disease status, and use that model to assign to the subject of unknown status a probability of having the disease status of interest.

In some embodiments, the method comprises a classification model using an exhaustive leave-one-out cross-validation, in which the immune profile dataset from an individual is held out of the calculations, and the process is repeated from the beginning. In one aspect, cross-validation is used to assess the accuracy of a classification model. The resulting classification model is used to predict the infectious disease status of the holdout subject.

These methods can be performed for determining disease status for various types of disease, including but not limited to CMV, EBV, HPV, HIV, small pox, other infectious diseases, or even non-infectious diseases, like autoimmune diseases and malignancies.

HLA Typing

HLA typing of bone marrow donor subjects was performed according to standard protocol by the Fred Hutchinson Cancer Research Center, and can be performed by methods known to those of skill in the art.

Method of Determining HLA Status of Unknown Subjects

FIG. 13 shows an overview of the method for inferring HLA status. This method can be applied to any HLA allele type and any profile of TCR sequences, including TCRA, TCRB, TCRG, or TCRD gene sequences.

First, the HLA allele type is determined for each subject in a group, according to standard methods in the art for HLA typing. Then, a locus of the subject's immune repertoire is sequenced. For example, the TCRβ locus is amplified and sequenced, using the methods described above.

For each subject, the total number of unique TCRβ sequences and the frequency of each unique TCRβ sequence are determined. For a given HLA allele, it is determined which TCRβ sequences are significantly associated with the HLA allele. In one embodiment, for each unique TCRβ sequence, it is determined how many subjects who are positive for an HLA allele have the TCRβ sequence and how many subjects who are negative for the HLA allele have the TCRβ sequence. In addition, it can be determined the number of subjects who are positive for an HLA allele and negative for the TCRβ sequence and the number of subjects who are negative for the HLA allele and positive for the TCRβ sequence. The table below shows categorization of subjects by the presence or absence of a TCRB sequence and the presence or absence of an HLA allele, HLA-A2.

|  | HLA-A2+ | HLA-A2− |
| --- | --- | --- |
| TCRβ sequence i present | $n_{i+}$ | $n_{i-}$ |
| TCRβ sequence i not present | $N_+ - n_{i+}$ | $N_- - n_{i-}$ |

FIG. 14 shows a list of exemplary unique TCRβ sequences and the number of subjects who are positive or negative for an HLA-A2 allele that have a particular TCRB sequence.

A p-value is determined for the association of each TCRβ sequence with an HLA status using a Fisher exact test (two-tailed). The p value for association of each TCR with allele status using a Fisher exact test (two tailed) is calculated as follows:

$$Pr(\text{table}) = \frac{\binom{n_+ + n_-}{n_+}\binom{N_+ + N_- - n_+ - n_-}{n_+ + n_-}}{\binom{N_+ + N_-}{N_+}}$$

FIG. 14 also shows exemplary p values that are calculated for the association of a particular TCRβ sequence with an HLA type (HLA-A2).

As shown in FIG. 15, a p value is selected as a cutoff for identifying a set of "Feature TCRS" from the entire list of possible TCR sequences. Defining a p-value threshold and permuting the allele status across individuals provides an estimate of false discovery rate. This is performed for each HLA allele, resulting in a set of allele-associated TCRβ sequences for each HLA allele present in the training data. In FIG. 15, a p value cutoff of $p \leq 10^{-4}$ and an FDR of 0.1 is used to identify 288 TCRβ sequences that are positively associated with HLA-A2. For each of the allele-associated TCRβ sequences, the frequency of the sequence is also determined in each subject.

The feature selection step is followed by a machine learning process. As shown in FIG. 16, for each HLA allele, a logistic regression model is trained using the set of feature vectors over all subjects, along with the known status for presence of that allele.

As shown in FIG. 17, an exhaustive leave-one-out cross validation is performed where one subject is removed from the analysis, and the HLA status of the subject is inferred based on feature selection and training from only the remaining subjects. The result is a set of classifiers (one for each HLA allele) that estimate the probability of positive status for each HLA allele, taking as input the feature vector for each allele.

Equipped with these classifiers, the HLA type of a new subject can be assessed by: 1. immune repertoire sequencing, 2. computing feature vectors for each allele, and 3. defining a probability threshold for positive status that will be applied to the output from each classifier. In this manner, an HLA status can be inferred for a new subject with an unknown HLA status.

In an embodiment, given the results of the feature selection scheme, a one-dimension allele score is determined as the fraction of an individual's unique TCRβ sequences that appear in the set of TCRβ sequences associated with a given allele. This single quantity, rather than a vector of features, may also be used for training a classifier and diagnosing novel individuals with similar accuracy.

Additionally, the specific classifier described (logistic regression) can be replaced with any of a number of other binary classifiers and gives substantially similar results. These include: k-nearest neighbors, random forests, artificial neural network, naïve Bayes, and support vector machine.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992).

Example 1: Identification of Cytomegalovirus (CMV)-Associated TCRs and Classification of CMV Status From Immunosequencing Data The first aim of the study was to create a comprehensive catalog of CMV-specific T cell receptor sequences. The goal was to identify both common and rare, shared TCRβ sequences enriched in CMV seropositive individuals relative to CMV seronegative individuals. CMV was used as a model because it provides an ideal test bed for the development of T cell biomarkers. CMV serostatus is widely available and easy access to near-equal numbers of seropositive (cases) and seronegative (control) individuals among healthy adults provides good statistical power for a rigorous analysis.

Figure 1:
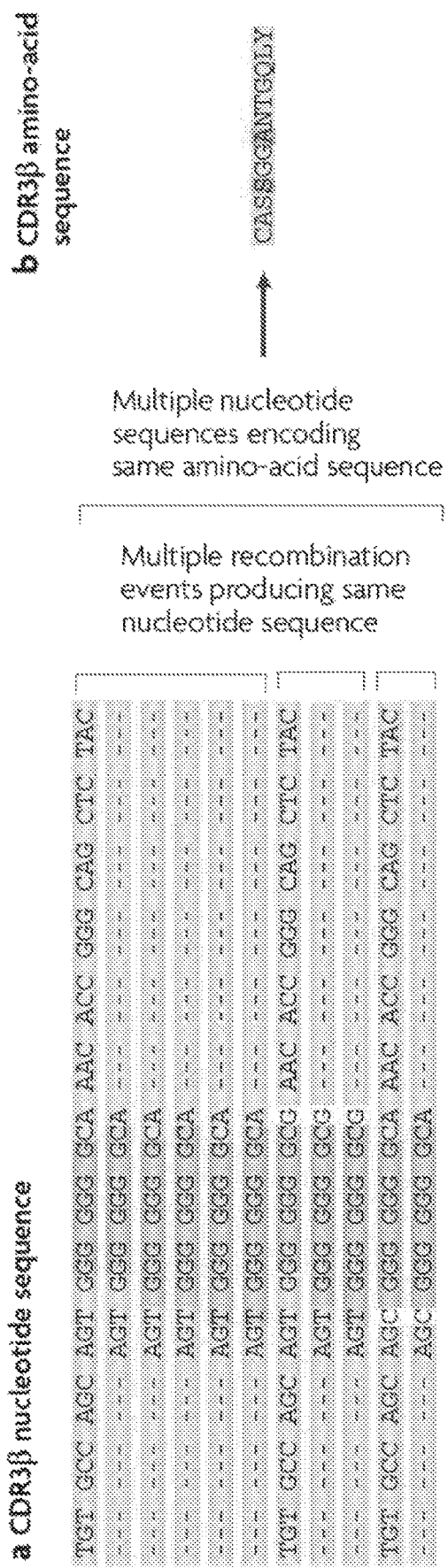

There are many possible TCR sequences generated during VDJ recombination ($\sim 10^{12}$ easily accessible by VDJ recombination). As shown in FIG. 1, different VDJ recombination events may result in the same nucleotide sequence. Moreover, it is possible that VDJ recombination can result in different nucleotide sequences that are translated into the same amino acid sequence. See Venturi, Price, Douek and Davenport 2008. The molecular basis for public T-cell responses? *Nature Reviews Immunology*. Certain TCRs are common rearrangements and shared by more than one individual. When a common TCR binds to an antigen, it is called a public T cell response. Public T cell responses are specific for a particular disease or antigen, are present in many individuals, and are encoded in a common format (specific rearranged receptor sequences) regardless of disease.

In this study, the public T cell response to cytomegalovirus (CMV) was examined by sequencing of rearranged T cell receptor genes (TCRs) obtained from 640 subjects. CMV is a life-long infection, usually asymptomatic, that afflicts most adults and elicits a robust memory T cell response.

Figure 2:
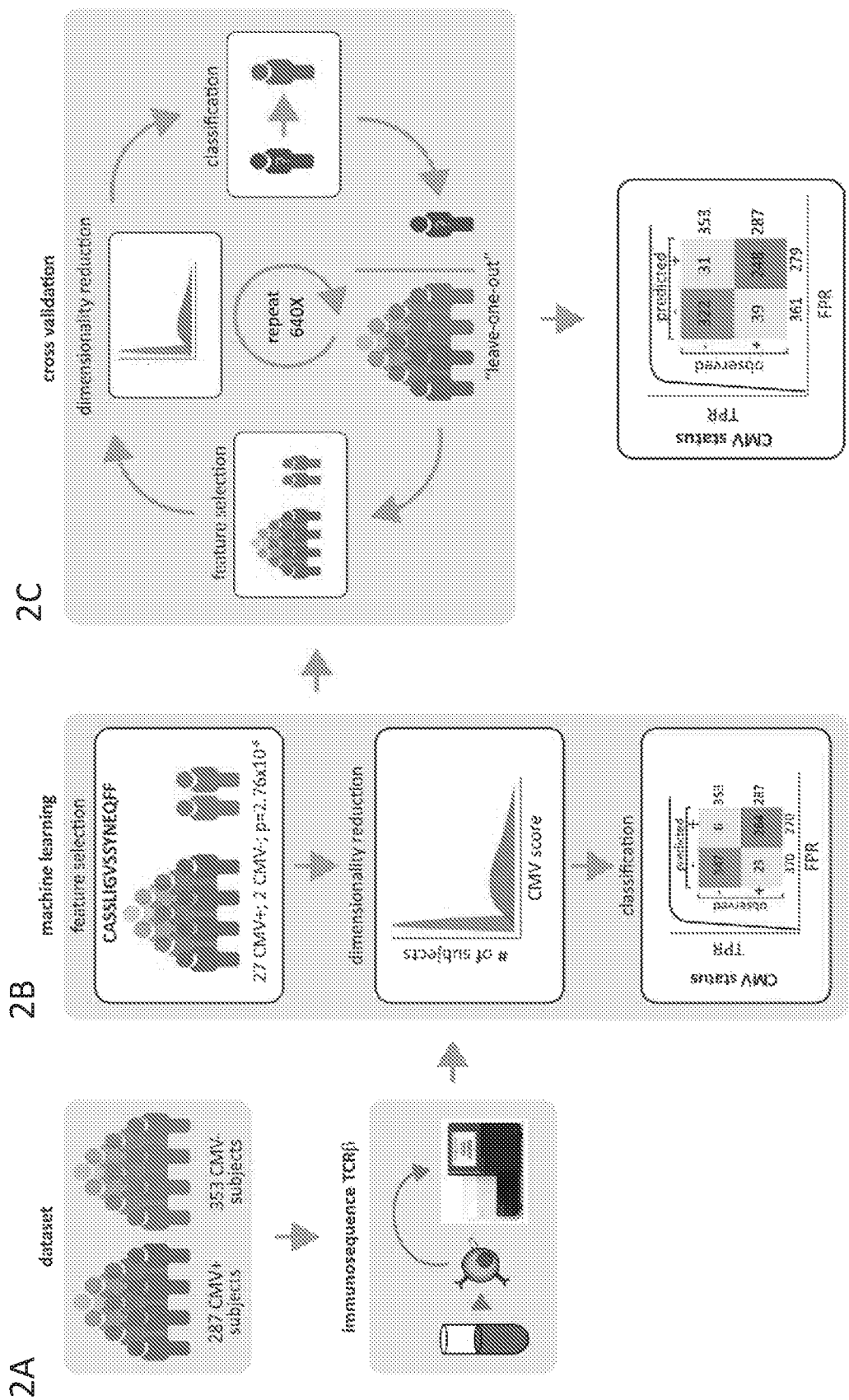
FIGS. 2A, 2B and 2C provide an overview of the method for predicting disease status of an individual, according to one embodiment of the invention.

FIGS. 2A, 2B and 2C provide an overview of the method, according to one embodiment of the invention. FIG. 2A shows a dataset of peripheral blood samples from 640 healthy subjects (287 CMV− and 353 CMV+), which were analyzed by high-throughput TCR profiling. In FIG. 2B, unique TCRβ sequences were identified that were present in significantly more CMV+ subjects than CMV− subjects, controlling false determination rate (FDR) by permutation of CMV status. Presence of these CMV-associated TCRβ sequences was used to build a classification model. In FIG. 2C, the classification model was tested using exhaustive leave-one-out cross-validation, in which one sample was held out of the calculations, and the process was repeated from the beginning. The resulting classification model was used to predict the CMV status of the holdout subject.

Human peripheral blood samples were obtained from the Fred Hutchinson Cancer Research Center Research Cell Bank biorepository of healthy bone marrow donors under a protocol following written informed consent approved and supervised by the Fred Hutchinson Cancer Research Center Institutional Review Board. This biorepository houses an inventory of PBMC, B-LCL and DNA from hematopoietic cell transplant (HCT) patients, donors and family members along with cell lines and DNA derived from stem cell transplant patients, donors and selected family members from 7,800 stem cell transplant patients and 7,300 donors (from which samples were drawn). The DNA for this study was extracted from peripheral blood of HCT donors and extensively typed for HLA antigens and alleles along with other defining phenotypes needed for donor-patient matching or donor inclusion/exclusion. Among these are cytomegalovirus (CMV), Epstein-Barr virus (EBV), Herpes Simplex Virus (HSV), hepatitis, and diabetes mellitus.

Figure 3A:
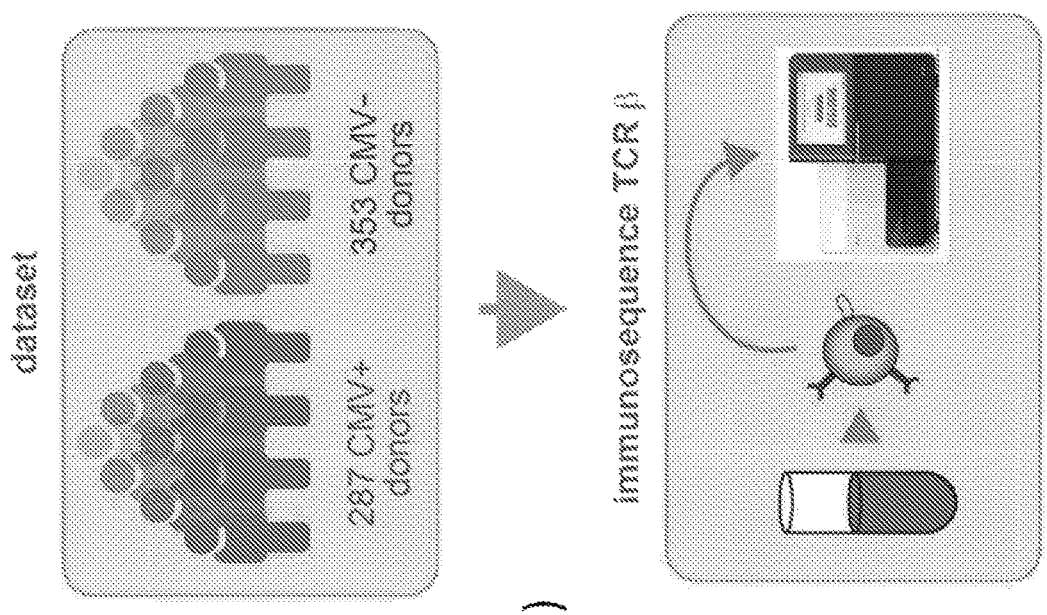
FIG. 3A depicts a graphical representation of a subject data set, where 640 subjects were specifically phenotyped for HLA type and CMB status for eligibility as an HCT donor, and segregated between 287 CMV+ donors and 353 CMV- donors. There were roughly equal numbers of seropositive and seronegative samples for the investigation of public T cell responses.

As shown in FIG. 3A, 640 subjects were specifically phenotyped for HLA type and CMV status for eligibility as a HCT donor, and segregated between 287 CMV+ donors and 353 CMV− donors. The CMV seropositive rate was approximately 45% (roughly equal numbers of seropositive and seronegative samples for the investigation of public T cell responses).

FIG. 3B shows demographic characteristics of the subjects included in this study, classified by CMV status.

High-Throughput TCRβ Sequencing:

Genomic DNA was extracted from peripheral blood samples using the Qiagen DNeasy Blood extraction Kit (Qiagen, Gaithersburg, Md., USA). The CDR3 regions of rearranged TCRβ genes were sequenced; the TCRβ CDR3 region was defined according to the IMGT collaboration[28, 20]. TCRβ CDR3 regions were amplified and sequenced using methods described above and in previously described protocols[5, 29]. The multiplexed PCR method used a mixture of 60 forward primers specific to TCR Vβ gene segments and 13 reverse primers specific to TCR Jβ gene segments. The resulting amplicons were sequenced using the methods described above. Reads of 87 bp were obtained using the Illumina HiSeq System. Raw HiSeq sequence data were preprocessed to remove errors in the primary sequence of each read, and to compress the data. A nearest neighbor algorithm was used to collapse the data into unique sequences by merging closely related sequences, to remove both PCR and sequencing errors.

In order to ensure adequate coverage of each T cell rearrangement, 8-10× sequence coverage, or ~6-10 million sequencing reads per sample, was generated using approximately eight full sequencing runs. All sequencing reads were processed using a standardized bioinformatics pipeline to 1) demultiplex reads to specific samples, 2) eliminate low quality sequence and remove potential contaminants, 3) align and identify specific TCRβ V and J gene segments and CDR3 regions, 4) cluster highly similar sequences to account for PCR and sequencing errors, 5) normalize data to remove PCR amplification bias, 6) estimate total T-cell input, and 7) generate TCRβ unique sequence counts and distributions.

Here, approximately 250,000 rearranged T cell receptor genes were sequenced from peripheral blood of each subject.

Feature Selection:

Across 640 subjects, there were 185,204 (+/−84,171) unique TCRβs per subject, and 83,727,796 unique TCRβs in aggregate. Rather than attempting high dimensional CMV classification using all unique TCRβs as potential features, a novel feature selection scheme was developed. Feature selection was selection of a particular amino acid sequence to identify common TCRs among individuals with CMV.

Since many clones were unique to a single subject (and consequently unique to either the CMV+ or CMV− classes), it was vital to control false discovery rate in feature selection to avoid over-fitting to the many spurious associations of unique TCRβs with CMV status.

Each unique TCRβ rearrangement, identified by V and J gene assignment and CDR3 amino acid sequence, was tested for CMV association. Each of these was subjected to a one-tailed Fisher exact test for its incidence in CMV− and CMV+ subjects. Specifically, letting $n_{ij}$ denote the number of subjects with CMV status j (with j− or +) and clone i present, a p-value $p_i$ was computed by performing Fisher's exact test on the contingency table.

|  | CMV+ | CMV− |
| --- | --- | --- |
| TCRβ sequence i present | $n_{i+}$ | $n_{i-}$ |
| TCRβ sequence i not present | $N_+ - n_{i+}$ | $N_- - n_{i-}$ | where $N_+$ and $N_-$ denote the total number of subjects having each CMV status (CMV+ and CMV− respectively).

To characterize a rejection region in the presence of many weakly dependent hypotheses (one for each unique TCRβ), CMV status assignments were randomly permuted 100 times, and statistics on the number of rejections at the nominal p-value threshold were calculated. Approximating the total fraction of true null hypotheses as unity, this allowed estimation of the false discovery rate (FDR) as the ratio of the mean number of rejections under permutation to the actual number of rejections.

Figure 4:
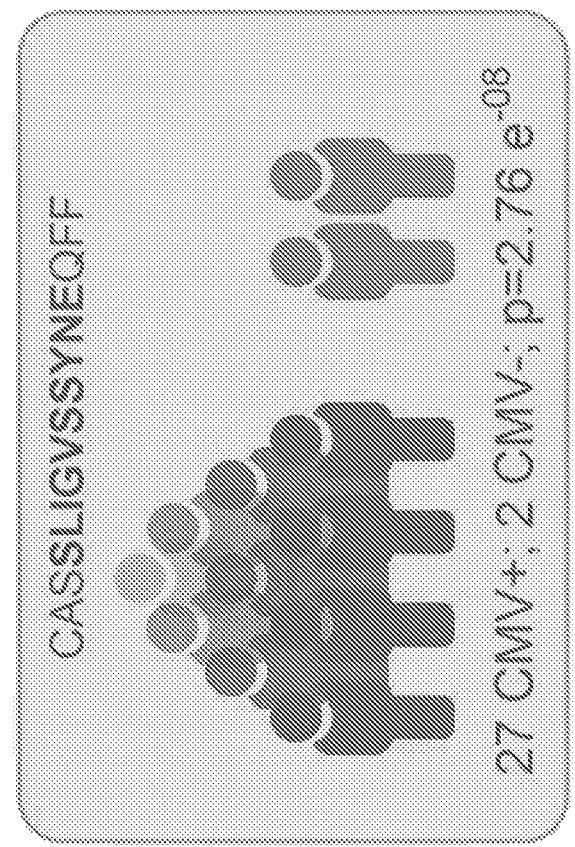
FIG. 4 depicts a test for CMV-association of TCRs, where the TCR amino acid sequence CASSLIGVSSYNEQFF (SEQ ID NO:12) was selected and identified in 27 of the CMV+ subjects, and only 2 of the CMV- subjects, with a p-value of $2.8E^{-08}$.

As shown by example in FIG. 4, the TCR amino acid sequence "CASSLIGVSSYNEQFF" (SEQ ID NO:12) was selected and was identified in 27 CMV+ subjects and 2 CMV− subjects (p=2.8E-08).

Figure 5:
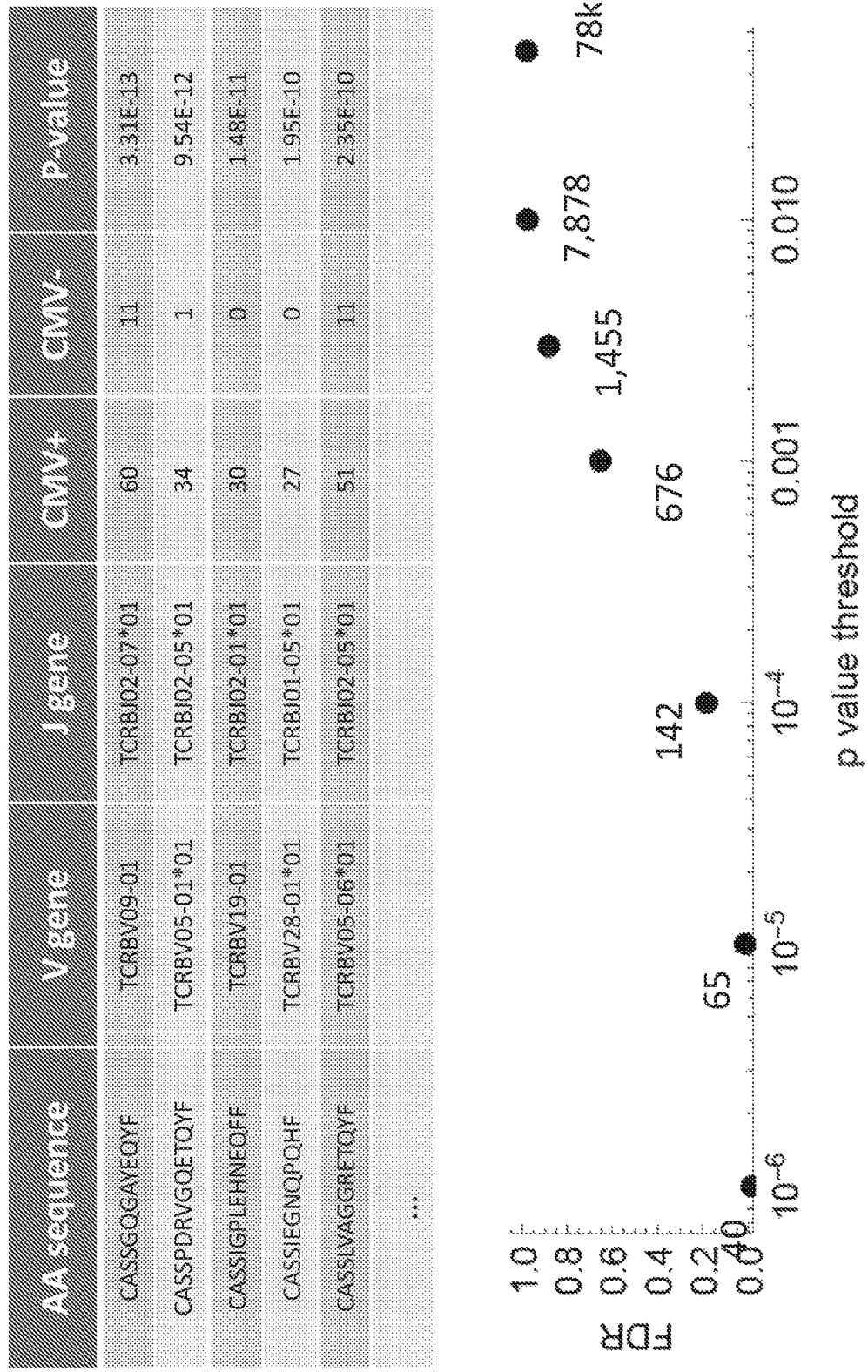
FIG. 5 depicts exemplary TCR amino acid sequences identified in CMV+ subjects with a p-value threshold chosen at $10^{-4}$. In order from top to bottom, these are SEQ ID NOs: 1-5. One can see that at a lower p-value, larger numbers of CMB-associated TCRβ sequences can be identified.

FIG. 5 shows exemplary TCR amino acid sequences identified in CMV+ subjects. As shown in Table 1, at a selected p value of $10^{-4}$, 142 public T cell clones were identified as associated with CMV+ subjects. The p value was chosen at $10^{-4}$, but as one can see, at a lower p value, larger numbers of CMV associated TCRβ sequences can be identified.

Table 1:

Each of the 142 TCRβ sequences significantly associated with CMV status (p≤1×$10^{-4}$, FDR~20%) in the cohort was included. Sequences were defined using the amino acid sequence of the CDR3 region along with V and J gene segments. The number of CMV+ and CMV− subjects in which each sequence was observed is given, as well as the p-value from a Fisher exact test for association with CMV status, and any HLA-A or HLA-B alleles that were significantly associated (p≤1×$10^{-3}$) with the presence of each sequence.

TABLE 1

Exemplary CMV-Associated TCRβ Sequences

| SEQ ID NO: | AA sequence | V gene | J gene | CMV+/CMV− | Fisher p value | HLA association(s) |
|---|---|---|---|---|---|---|
| 1 | CASSGQGAYEQYF | TCRBV09-01 | TCRBJ02-07*03 | 60/11 | 3.3142E-13 | A29, B13 |
| 2 | CASSPDRVGQETQYF | TCRBV05-01*01 | TCRBJ02-05*03 | 34/1 | 9.5395E-12 | None |
| 3 | CASSIGPLEHNEQFF | TCRBV19-01 | TCRBJ02-01*03 | 30/0 | 1.4752E-11 | A1, B8 |
| 4 | CASSIEGNQPQHF | TCRBV28-01*01 | TCRBJ01-05*03 | 27/0 | 1.9463E-10 | None |
| 5 | CASSLVAGGRETQYF | TCRBV05-06*01 | TCRBJ02-05*03 | 51/11 | 2.3538E-10 | B8 |
| 6 | CASSLEAEYEQYF | TCRBV07-02*01 | TCRBJ02-07*03 | 30/1 | 2.7085E-10 | B8 |
| 7 | CATSDGDEQFF | TCRBV24 | TCRBJ02-01*03 | 41/6 | 4.7339E-10 | A1 |
| 8 | CASSLAPGATNEKLFF | TCRBV07-06*01 | TCRBJ01-04*03 | 36/4 | 9.134E-10 | A2 |
| 9 | CASSRGRQETQYF | TCRBV07-06*01 | TCRBJ02-05*03 | 37/5 | 2.1095E-09 | None |
| 10 | CASSAGQGVTYEQYF | TCRBV09-01 | TCRBJ02-07*03 | 23/0 | 5.8832E-09 | A1, B8 |
| 11 | CASSLRREKLFF | TCRBV05-06*01 | TCRBJ01-04*03 | 28/2 | 1.2553E-08 | A29, B50 |
| 12 | CASSLIGVSSYNEQFF | TCRBV07-09 | TCRBJ02-01*03 | 27/2 | 2.7588E-08 | A3, B7 |
| 13 | CASSFPTSGQETQYF | TCRBV07-09 | TCRBJ02-05*03 | 27/2 | 2.7588E-08 | A24 |
| 14 | CASSPQRNTEAFF | TCRBV04-03*01 | TCRBJ01-01*03 | 27/2 | 2.7588E-08 | A3, B7 |
| 15 | CSVRDNFNQPQHF | TCRBV29-01*01 | TCRBJ01-05*03 | 21/0 | 3.1927E-08 | None |
| 16 | CATSRDSQGSYGYTF | TCRBV15-01*01 | TCRBJ01-02*03 | 21/0 | 3.1927E-08 | None |
| 17 | CASSPGDEQYF | TCRBV25-01*01 | TCRBJ02-07*03 | 24/1 | 3.7138E-08 | B7 |
| 18 | CASSQTGGRNQPQHF | TCRBV12 | TCRBJ01-05*03 | 26/2 | 6.0357E-08 | A2 |
| 19 | CASSQNRGQETQYF | TCRBV14-01*01 | TCRBJ02-05*03 | 26/2 | 6.0357E-08 | None |
| 20 | CASSLVIGGDTEAFF | TCRBV05-01*01 | TCRBJ01-01*03 | 26/2 | 6.0357E-08 | B8 |
| 21 | CASSFHGFNQPQHF | TCRBV05-06*01 | TCRBJ01-05*03 | 20/0 | 7.4139E-08 | A1, B8 |
| 22 | CASSRLAGGTDTQYF | TCRBV07-03*01 | TCRBJ02-03*03 | 50/16 | 7.5065E-08 | A1, B8 |
| 23 | CASSLPSGLTDTQYF | TCRBV28-01*01 | TCRBJ02-03*03 | 25/2 | 1.3144E-07 | None |
| 24 | CATSRDTQGSYGYTF | TCRBV15-01*01 | TCRBJ01-02*03 | 19/0 | 1.7179E-07 | None |
| 25 | CATSDGDTQYF | TCRBV24 | TCRBJ02-03*03 | 51/18 | 2.2203E-07 | A1, B8 |
| 26 | CASSLVASGRETQYF | TCRBV05-06*01 | TCRBJ02-05*03 | 24/2 | 2.8483E-07 | None |
| 27 | CASSIWGLDTEAFF | TCRBV19-01 | TCRBJ01-01*03 | 28/4 | 3.6207E-07 | None |
| 28 | CASSPGDEQFF | TCRBV25-01*01 | TCRBJ02-01*03 | 28/4 | 3.6207E-07 | B7 |
| 29 | CASSPSTGTEAFF | TCRBV05-06*01 | TCRBJ01-01*03 | 18/0 | 3.9723E-07 | None |
| 30 | CSVEEDEGIYGYTF | TCRBV29-01*01 | TCRBJ01-02*03 | 18/0 | 3.9723E-07 | None |
| 31 | CASSEIPNTEAFF | TCRBV06-04 | TCRBJ01-01*03 | 18/0 | 3.9723E-07 | A24 |
| 32 | CASSQVPGQGDNEQFF | TCRBV14-01*01 | TCRBJ02-01*03 | 21/1 | 4.1428E-07 | A1, B8 |

TABLE 1-continued

Exemplary CMV-Associated TCRβ Sequences

| SEQ ID NO: | AA sequence | V gene | J gene | CMV+/CMV- | Fisher p value | HLA association(s) |
|---|---|---|---|---|---|---|
| 33 | CASSPAGLNTEAFF | TCRBV19-01 | TCRBJ01-01*03 | 21/1 | 4.1428E-07 | None |
| 34 | CASSLGLKGTQYF | TCRBV12 | TCRBJ02-05*03 | 21/1 | 4.1428E-07 | None |
| 35 | CASSGDRLYEQYF | TCRBV02-01*01 | TCRBJ02-07*03 | 23/2 | 6.1415E-07 | None |
| 36 | CSVRDNYNQPQHF | TCRBV29-01*01 | TCRBJ01-05*03 | 23/2 | 6.1415E-07 | None |
| 37 | CASSYGGLGSYEQYF | TCRBV06-05*01 | TCRBJ02-07*03 | 23/2 | 6.1415E-07 | None |
| 38 | CASNRDRGRYEQYF | TCRBV06-01*01 | TCRBJ02-07*03 | 20/1 | 9.1836E-07 | B45 |
| 39 | CASMGGASYEQYF | TCRBV27-01*01 | TCRBJ02-07*03 | 20/1 | 9.1836E-07 | A2 |
| 40 | CASSLGVGPYNEQFF | TCRBV07-02*01 | TCRBJ02-01*03 | 20/1 | 9.1836E-07 | B7 |
| 41 | CASSLGGAGDTQYF | TCRBV12 | TCRBJ02-03*03 | 44/15 | 1.1802E-06 | None |
| 42 | CATSRGTVSYEQYF | TCRBV15-01*01 | TCRBJ02-07*03 | 30/6 | 1.2303E-06 | None |
| 43 | CATSDGETQYF | TCRBV24 | TCRBJ02-05*03 | 70/36 | 1.3031E-06 | A1, B52 |
| 44 | CASSEARGGVEKLFF | TCRBV06-01*01 | TCRBJ01-04*03 | 22/2 | 1.3173E-06 | None |
| 45 | CASSLNRGQETQYF | TCRBV14-01*01 | TCRBJ02-05*03 | 19/1 | 2.0272E-06 | None |
| 46 | CSVRDNHNQPQHF | TCRBV29-01*01 | TCRBJ01-05*03 | 19/1 | 2.0272E-06 | None |
| 47 | CASSESGHRNQPQHF | TCRBV10-02*01 | TCRBJ01-05*03 | 16/0 | 2.1105E-06 | None |
| 48 | CSASPGQGASYGYTF | TCRBV20 | TCRBJ01-02*03 | 16/0 | 2.1105E-06 | None |
| 49 | CASSEARTRAFF | TCRBV06-01*01 | TCRBJ01-01*03 | 16/0 | 2.1105E-06 | None |
| 50 | CASRPTGYEQYF | TCRBV06-01*01 | TCRBJ02-07*03 | 21/2 | 2.8099E-06 | B39 |
| 51 | CASSVTGGTDTQYF | TCRBV09-01 | TCRBJ02-03*03 | 74/41 | 2.8214E-06 | A1, B8 |
| 52 | CASSRLAASTDTQYF | TCRBV07-03*01 | TCRBJ02-03*03 | 23/3 | 3.1389E-06 | A1, B8 |
| 53 | CATSDSVTNTGELFF | TCRBV24 | TCRBJ02-02*03 | 18/1 | 4.4551E-06 | B8 |
| 54 | CASSRNRESNQPQHF | TCRBV06-05*01 | TCRBJ01-05*03 | 18/1 | 4.4551E-06 | None |
| 55 | CASSAQGAYEQYF | TCRBV09-01 | TCRBJ02-07*03 | 28/6 | 4.717E-06 | None |
| 56 | CASSIQGYSNQPQHF | TCRBV05-08*01 | TCRBJ01-05*03 | 15/0 | 4.8494E-06 | B8 |
| 57 | CASSYNPYSNQPQHF | TCRBV06-06 | TCRBJ01-05*03 | 15/0 | 4.8494E-06 | None |
| 58 | CASSLGHRDPNTGELFF | TCRBV05-01*01 | TCRBJ02-02*03 | 15/0 | 4.8494E-06 | B13 |
| 59 | CASSTTGGDGYTF | TCRBV19-01 | TCRBJ01-02*03 | 26/5 | 5.5727E-06 | None |
| 60 | CASSVLAGPTDTQYF | TCRBV09-01 | TCRBJ02-03*03 | 26/5 | 5.5727E-06 | A1 |
| 61 | CASSYRQETQYF | TCRBV06-05*01 | TCRBJ02-05*03 | 20/2 | 5.9592E-06 | None |
| 62 | CASSSGQVYGYTF | TCRBV05-06*01 | TCRBJ01-02*03 | 22/3 | 6.4736E-06 | A1, B8 |
| 63 | CASGRDTYEQYF | TCRBV02-01*01 | TCRBJ02-07*03 | 17/1 | 9.7453E-06 | None |
| 64 | CATSDSRTGGQETQYF | TCRBV24 | TCRBJ02-05*03 | 17/1 | 9.7453E-06 | B8 |
| 65 | CASSSPGRSGANVLTF | TCRBV28-01*01 | TCRBJ02-06*03 | 17/1 | 9.7453E-06 | None |
| 66 | CASSYGGEGYTF | TCRBV06-05*01 | TCRBJ01-02*03 | 36/12 | 1.059E-05 | None |
| 67 | CASSLAGVDYEQYF | TCRBV07-09 | TCRBJ02-07*03 | 25/5 | 1.0951E-05 | B8 |
| 68 | CASSLQGADTQYF | TCRBV07-08*01 | TCRBJ02-03*03 | 14/0 | 1.112E-05 | None |
| 69 | CASSLEAENEQFF | TCRBV07-02*01 | TCRBJ02-01*03 | 14/0 | 1.112E-05 | A11, B8 |
| 70 | CASSEAPSTSTDTQYF | TCRBV02-01*01 | TCRBJ02-03*03 | 14/0 | 1.112E-05 | None |

TABLE 1-continued

Exemplary CMV-Associated TCRβ Sequences

| SEQ ID NO: | AA sequence | V gene | J gene | CMV+/CMV- | Fisher p value | HLA association(s) |
|---|---|---|---|---|---|---|
| 71 | CASSLEGQQPQHF | TCRBV28-01*01 | TCRBJ01-05*03 | 14/0 | 1.112E-05 | None |
| 72 | CASSLGHRDSSYEQYF | TCRBV05-01*01 | TCRBJ02-07*03 | 14/0 | 1.112E-05 | A29, B57 |
| 73 | CASSPSRNTEAFF | TCRBV04-03*01 | TCRBJ01-01*03 | 19/2 | 1.2561E-05 | A3, B7 |
| 74 | CSALGHSNQPQHF | TCRBV20 | TCRBJ01-05*03 | 19/2 | 1.2561E-05 | None |
| 75 | CASSHRDRNYEQYF | TCRBV07-09 | TCRBJ02-07*03 | 19/2 | 1.2561E-05 | A24 |
| 76 | CASSPPGQGSDTQYF | TCRBV18-01*01 | TCRBJ02-03*03 | 28/7 | 1.3913E-05 | None |
| 77 | CASSLQGYSNQPQHF | TCRBV05-08*01 | TCRBJ01-05*03 | 34/11 | 1.4711E-05 | B8 |
| 78 | CASSYVRTGGNYGYTF | TCRBV06-05*01 | TCRBJ01-02*03 | 31/9 | 1.5052E-05 | None |
| 79 | CASSRDRNYGYTF | TCRBV06-04 | TCRBJ01-02*03 | 29/8 | 2.0024E-05 | None |
| 80 | CASSTGTSGSYEQYF | TCRBV06-01*01 | TCRBJ02-07*03 | 16/1 | 2.1213E-05 | B54 |
| 81 | CASRSDSGANVLTF | TCRBV06-04 | TCRBJ02-06*03 | 16/1 | 2.1213E-05 | None |
| 82 | CATSRVAGETQYF | TCRBV15-01*01 | TCRBJ02-05*03 | 24/5 | 2.1345E-05 | B7 |
| 83 | CASSEEGIQPQHF | TCRBV02-01*01 | TCRBJ01-05*03 | 22/4 | 2.4814E-05 | None |
| 84 | CASSLGGPGDTQYF | TCRBV12 | TCRBJ02-03*03 | 22/4 | 2.4814E-05 | None |
| 85 | CASSLVAAGRETQYF | TCRBV05-06*01 | TCRBJ02-05*03 | 13/0 | 2.5446E-05 | B8 |
| 86 | CASRGQGWDEKLFF | TCRBV06-05*01 | TCRBJ01-04*03 | 13/0 | 2.5446E-05 | None |
| 87 | CASSLEGQGFGYTF | TCRBV05-01*01 | TCRBJ01-02*03 | 13/0 | 2.5446E-05 | None |
| 88 | CASRDWDYTDTQYF | TCRBV02-01*01 | TCRBJ02-03*03 | 13/0 | 2.5446E-05 | None |
| 89 | CASSRSGLAGNTGELFF | TCRBV06 | TCRBJ02-02*03 | 13/0 | 2.5446E-05 | None |
| 90 | CASSPGQEAGANVLTF | TCRBV05-01*01 | TCRBJ02-06*03 | 13/0 | 2.5446E-05 | None |
| 91 | CASSLGDRPDTQYF | TCRBV11-02*02 | TCRBJ02-03*03 | 13/0 | 2.5446E-05 | None |
| 92 | CASSFPGGETQYF | TCRBV11-01*01 | TCRBJ02-05*03 | 18/2 | 2.6306E-05 | None |
| 93 | CASSLETYGYTF | TCRBV05-06*01 | TCRBJ01-02*03 | 18/2 | 2.6306E-05 | B78 |
| 94 | CASSSGQVQETQYF | TCRBV11-02*02 | TCRBJ02-05*03 | 18/2 | 2.6306E-05 | B51 |
| 95 | CASSFDNYGYTF | TCRBV05-04*01 | TCRBJ01-02*03 | 18/2 | 2.6306E-05 | None |
| 96 | CASSEGARQPQHF | TCRBV10-02*01 | TCRBJ01-05*03 | 18/2 | 2.6306E-05 | None |
| 97 | CASSLTGGRNQPQHF | TCRBV12 | TCRBJ01-05*03 | 33/11 | 2.6324E-05 | A2 |
| 98 | CASSLLWDQPQHF | TCRBV05-05*01 | TCRBJ01-05*03 | 20/3 | 2.6954E-05 | None |
| 99 | CASSLFGTGGNTEAFF | TCRBV05-06*01 | TCRBJ01-01*03 | 20/3 | 2.6954E-05 | B44 |
| 100 | CASSISAGEAFF | TCRBV19-01 | TCRBJ01-01*03 | 20/3 | 2.6954E-05 | None |
| 101 | CASSPPSGLTDTQYF | TCRBV28-01*01 | TCRBJ02-03*03 | 20/3 | 2.6954E-05 | None |
| 102 | CASSPLSDTQYF | TCRBV07-09 | TCRBJ02-03*03 | 30/9 | 2.752E-05 | None |
| 103 | CASSSRGTGELFF | TCRBV28-01*01 | TCRBJ02-02*03 | 25/6 | 3.3358E-05 | None |
| 104 | CASSYAGDGYTF | TCRBV06-05*01 | TCRBJ01-02*03 | 31/10 | 3.6414E-05 | B8 |
| 105 | CASSDRGNTGELFF | TCRBV04-01*01 | TCRBJ02-02*03 | 31/10 | 3.6414E-05 | A68, B41 |
| 106 | CASSPGGTQYF | TCRBV12 | TCRBJ02-05*03 | 28/8 | 3.6921E-05 | None |
| 107 | CASSLGDRAYNEQFF | TCRBV05-06*01 | TCRBJ02-01*03 | 28/8 | 3.6921E-05 | None |

TABLE 1-continued

Exemplary CMV-Associated TCRβ Sequences

| SEQ ID NO: | AA sequence | V gene | J gene | CMV+/CMV- | Fisher p value | HLA association(s) |
|---|---|---|---|---|---|---|
| 108 | CASSLRGSSYNEQFF | TCRBV05-08*01 | TCRBJ02-01*03 | 23/5 | 4.1254E-05 | None |
| 109 | CASSLTASSYEQYF | TCRBV05-01*01 | TCRBJ02-07*03 | 23/5 | 4.1254E-05 | None |
| 110 | CSASDHEQYF | TCRBV20-01*01 | TCRBJ02-07*03 | 23/5 | 4.1254E-05 | None |
| 111 | CASSQGRHTDTQYF | TCRBV14-01*01 | TCRBJ02-03*03 | 15/1 | 4.5934E-05 | A68 |
| 112 | CASSRPGQGNTEAFF | TCRBV12 | TCRBJ01-01*03 | 26/7 | 4.8714E-05 | None |
| 113 | CASSLVGDGYTF | TCRBV07-08*01 | TCRBJ01-02*03 | 36/14 | 4.9771E-05 | None |
| 114 | CASSLGAGNQPQHF | TCRBV28-01*01 | TCRBJ01-05*03 | 29/9 | 4.9861E-05 | None |
| 115 | CASSLTDTGELFF | TCRBV11-02*02 | TCRBJ02-02*03 | 29/9 | 4.9861E-05 | None |
| 116 | CASSLTGGNSGNTIYF | TCRBV07-02*01 | TCRBJ01-03*03 | 19/3 | 5.4373E-05 | B14 |
| 117 | CAWRGTGNSPLHF | TCRBV30-01*01 | TCRBJ01-06*03 | 17/2 | 5.4712E-05 | None |
| 118 | CASASANYGYTF | TCRBV12 | TCRBJ01-02*03 | 12/0 | 5.8109E-05 | A2 |
| 119 | CASSLQAGANEQFF | TCRBV07-02*01 | TCRBJ02-01*03 | 12/0 | 5.8109E-05 | None |
| 120 | CASSEEAGGSGYTF | TCRBV06-01*01 | TCRBJ01-02*03 | 12/0 | 5.8109E-05 | None |
| 121 | CASRTGESGYTF | TCRBV06-05*01 | TCRBJ01-02*03 | 12/0 | 5.8109E-05 | None |
| 122 | CASSGLNEQFF | TCRBV06-01*01 | TCRBJ02-01*03 | 12/0 | 5.8109E-05 | None |
| 123 | CASSWDRDNSPLHF | TCRBV25-01*01 | TCRBJ01-06*03 | 12/0 | 5.8109E-05 | B7 |
| 124 | CASSIRTNYYGYTF | TCRBV19-01 | TCRBJ01-02*03 | 12/0 | 5.8109E-05 | None |
| 125 | CSARSPEAFF | TCRBV20-01*01 | TCRBJ01-01*03 | 12/0 | 5.8109E-05 | None |
| 126 | CASSRGTGATDTQYF | TCRBV19-01 | TCRBJ02-03*03 | 12/0 | 5.8109E-05 | None |
| 127 | CASSPRVSNQPQHF | TCRBV12 | TCRBJ01-05*03 | 12/0 | 5.8109E-05 | None |
| 128 | CAISESQDRGHEQYF | TCRBV10-03*01 | TCRBJ02-07*03 | 12/0 | 5.8109E-05 | None |
| 129 | CASSLGRGYEKLFF | TCRBV05-06*01 | TCRBJ01-04*03 | 12/0 | 5.8109E-05 | B62 |
| 130 | CSVEVRGTDTQYF | TCRBV29-01*01 | TCRBJ02-03*03 | 12/0 | 5.8109E-05 | None |
| 131 | CASRGQGAGELFF | TCRBV02-01*01 | TCRBJ02-02*03 | 30/10 | 6.4924E-05 | None |
| 132 | CATSREGSGYEQYF | TCRBV15-01*01 | TCRBJ02-07*03 | 22/5 | 7.9023E-05 | None |
| 133 | CASSLGWTEAFF | TCRBV05-01*01 | TCRBJ01-01*03 | 22/5 | 7.9023E-05 | None |
| 134 | CASSLGSSSYNEQFF | TCRBV07-02*01 | TCRBJ02-01*03 | 35/14 | 8.4988E-05 | None |
| 135 | CASSSAGADTQYF | TCRBV07-09 | TCRBJ02-03*03 | 14/1 | 9.8907E-05 | B5 |
| 136 | CASSERKNYGYTF | TCRBV06-01*01 | TCRBJ01-02*03 | 14/1 | 9.8907E-05 | None |
| 137 | CASRDRDRVNTEAFF | TCRBV06-01*01 | TCRBJ01-01*03 | 14/1 | 9.8907E-05 | A3 |
| 138 | CASSRVGEQFF | TCRBV03 | TCRBJ02-01*03 | 14/1 | 9.8907E-05 | None |
| 139 | CASSPRWQETQYF | TCRBV27-01*01 | TCRBJ02-05*03 | 14/1 | 9.8907E-05 | B14 |
| 140 | CASTPGDTIYF | TCRBV25-01*01 | TCRBJ01-03*03 | 14/1 | 9.8907E-05 | B55 |
| 141 | CASSENGGNQPQHF | TCRBV06-01*01 | TCRBJ01-05*03 | 14/1 | 9.8907E-05 | None |
| 142 | CASSYPGETQYF | TCRBV06-06 | TCRBJ02-05*03 | 36/15 | 9.991E-05 | None |

Figure 6:
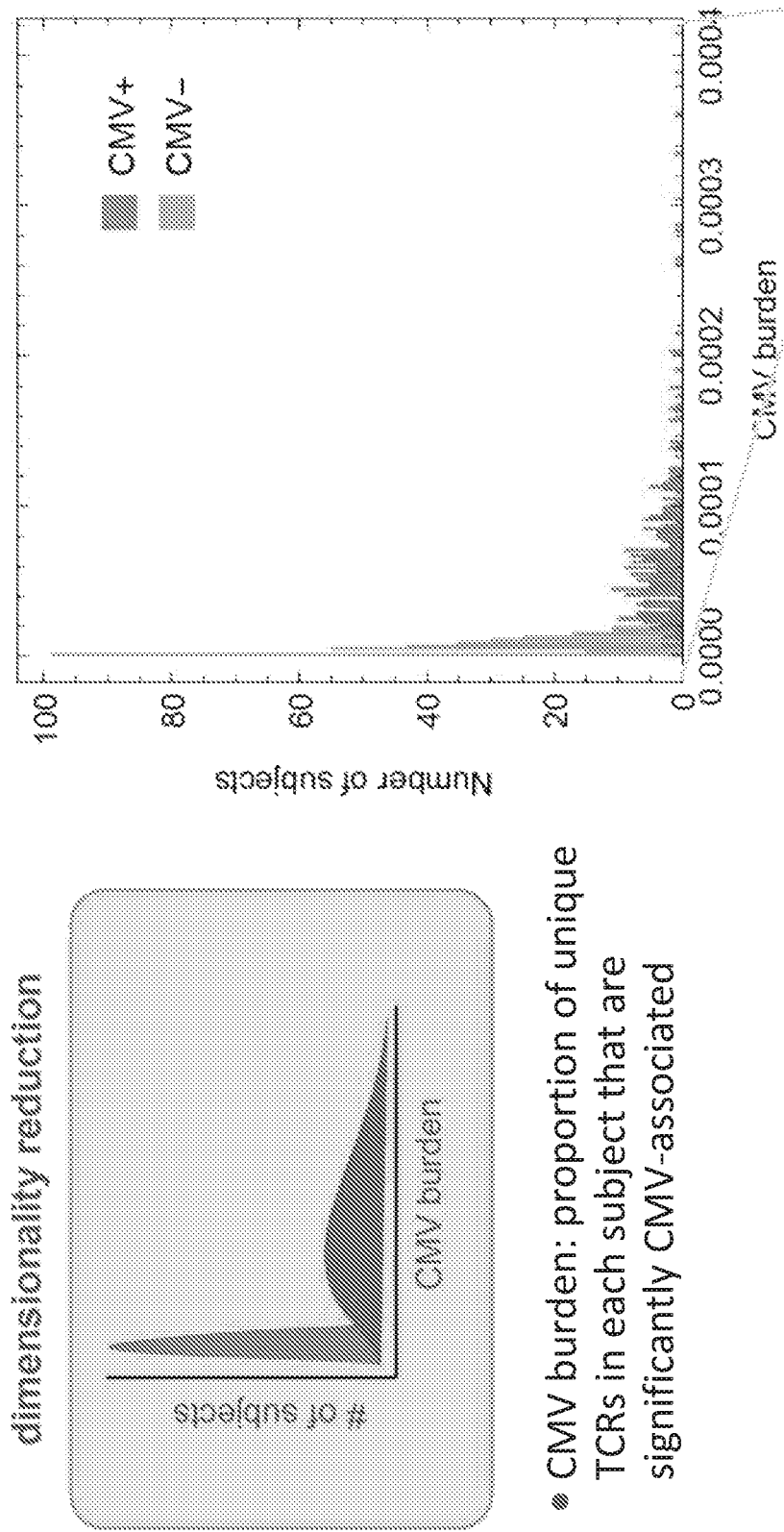
FIG. 6 depicts the CMV burden, which is represented as the proportion of unique TCRs in each subject that are significantly CMV-associated versus those TCRs that are not significantly CMV-associated.

Dimensionality Reduction and Machine Learning:

CMV burden was calculated for each subject. CMV burden is defined as the fraction of a subject's unique TCRβs that are significantly CMV-associated, as shown in FIG. 6. The graph in FIG. 6 shows the distribution of CMV scores (i.e., the proportion of each subject's TCRβ repertoire that matches our list of 142 CMV-associated TCRβ sequences) among CMV+ and CMV− subjects.

This enabled fast training of a one-dimensional logistic regression classifier of CMV status. Exhaustive leave-one-out cross validation (including re-computation of CMV-associated clones) was performed, indicating high accuracy across a broad range of p-value thresholds, with performance degrading at a high FDR.

Each subject was removed from the dataset in turn, and the list of significantly CMV-associated TCRβs was re-calculated using the remaining subjects with known CMV status. Each subject's CMV burden was then calculated as described above. A one-dimensional logistic regression classifier was then trained on CMV burden vs. CMV status, and the CMV burden of the subject which was held out was then calculated and input into the logistic regression. The output of this logistic regression model was the probability that the subject of unknown status was CMV+, which was then compared to the (known but not leveraged) status of the held-out subject to determine the accuracy of the hold-out classification. Classification of a subject with genuinely unknown CMV status proceeds likewise: sequence TCRβ, calculate a CMV burden (as proportion of unique TCRβs from this subject present on the list of CMV-associated TCRβs), and input this CMV burden into a logistic regression model trained on subjects of known status, with an estimated probability of CMV-positivity as output.

Figure 7:
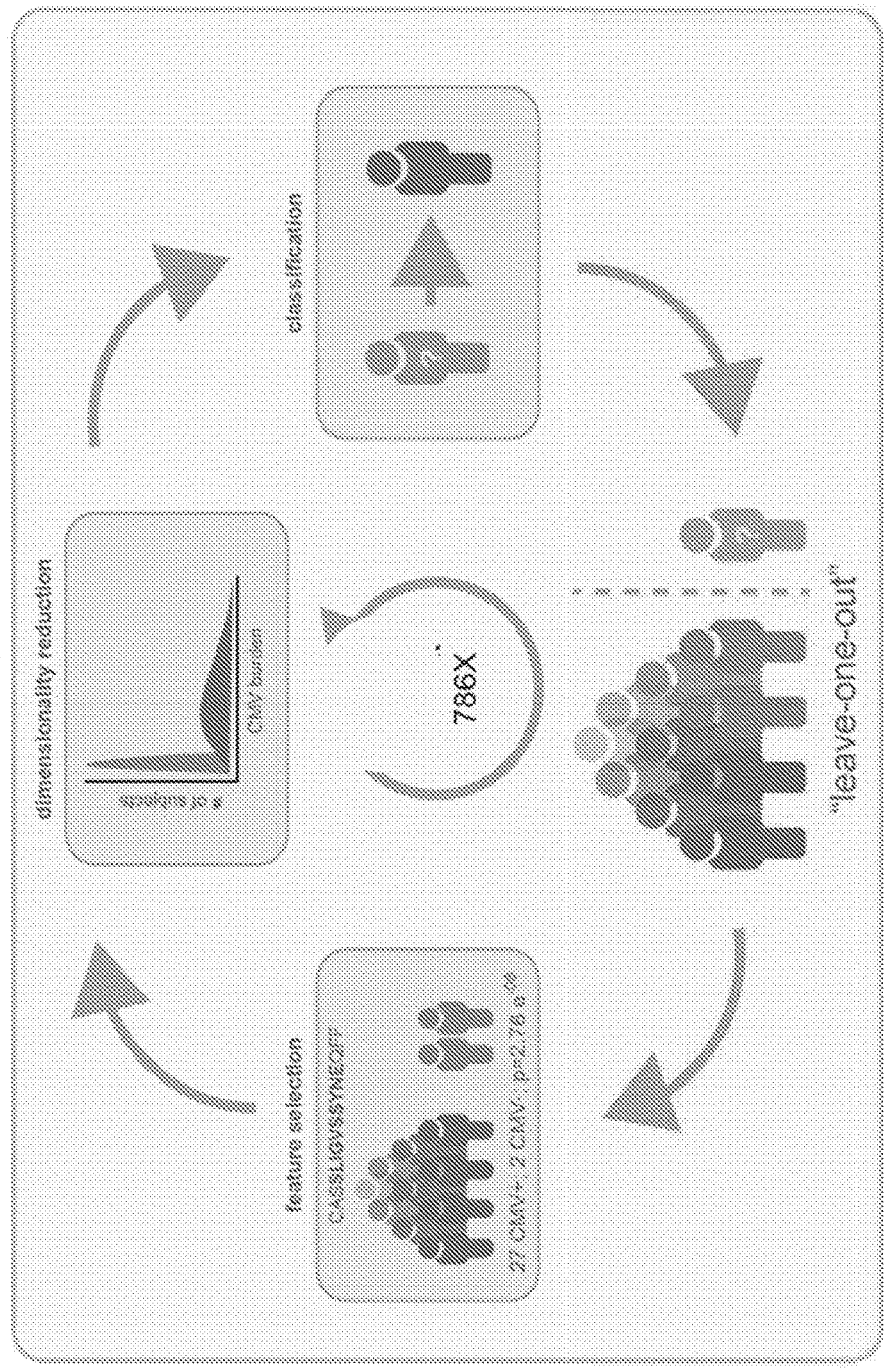
FIG. 7 depicts the cross-validation method, which leaves out one of the initial 640 samples, then the database of CMV-specific TCRβ sequences and associated statistics is retrained in an unsupervised fashion to eliminate bias, and the CMV serostatus of the left-out sample is classified.

As shown in FIG. 7, the cross-validation method left out one of the initial 640 samples, then the database of CMV-specific TCRβ sequences and associated statistics was retrained in an unsupervised fashion to eliminate bias, and the CMV serostatus of the left-out sample was classified.

Figure 8:
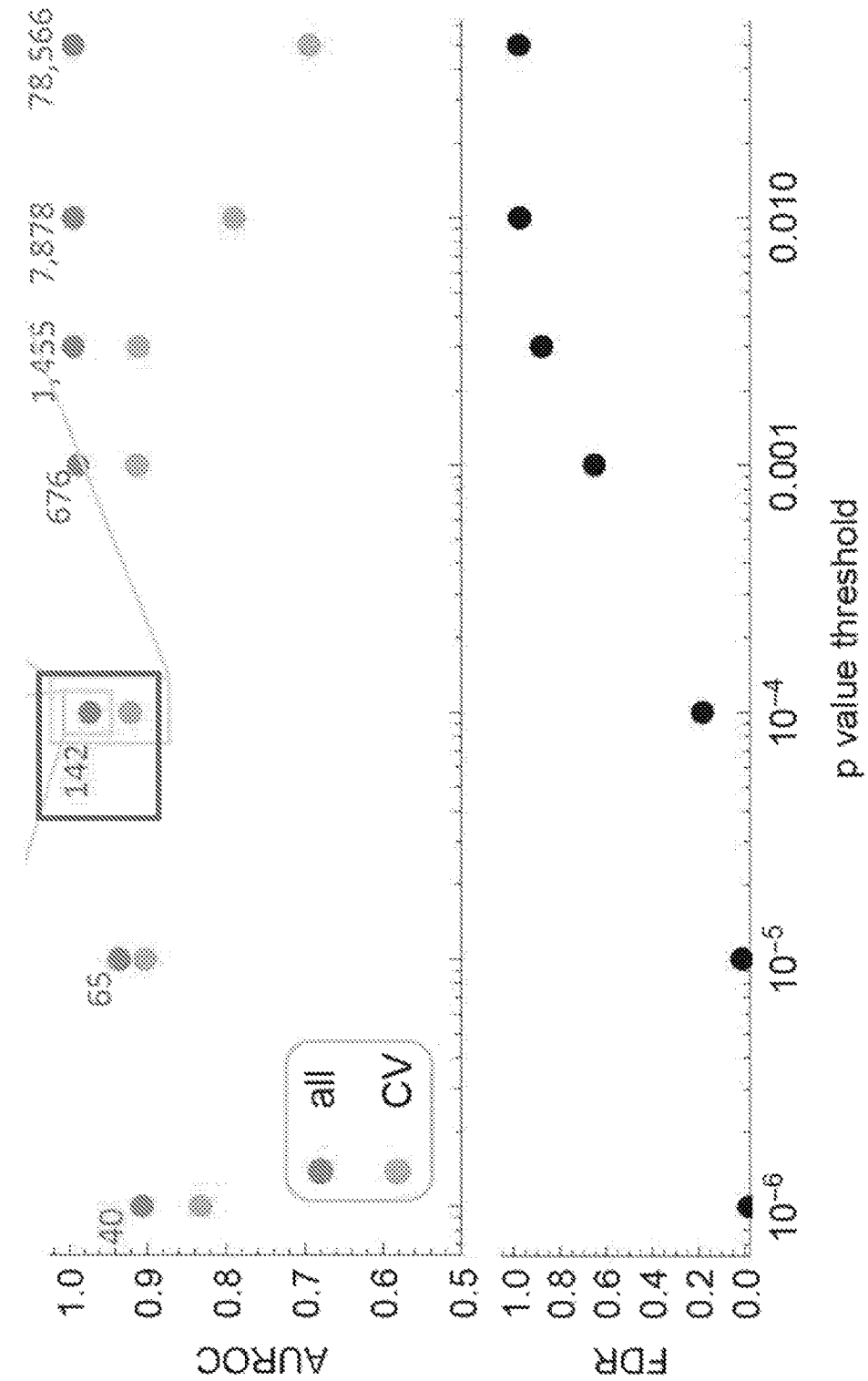
FIG. 8 depicts the results of the cross-validation method shown for all subjects and cross-validated subjects. The data is presented as the area under receiver operating characteristic (AUROC) in the y-axis versus the p-value across the x-axis. The results of the cross-validation method are shown as a plot of the false positive rate versus the true positive rate.
Figure 9:
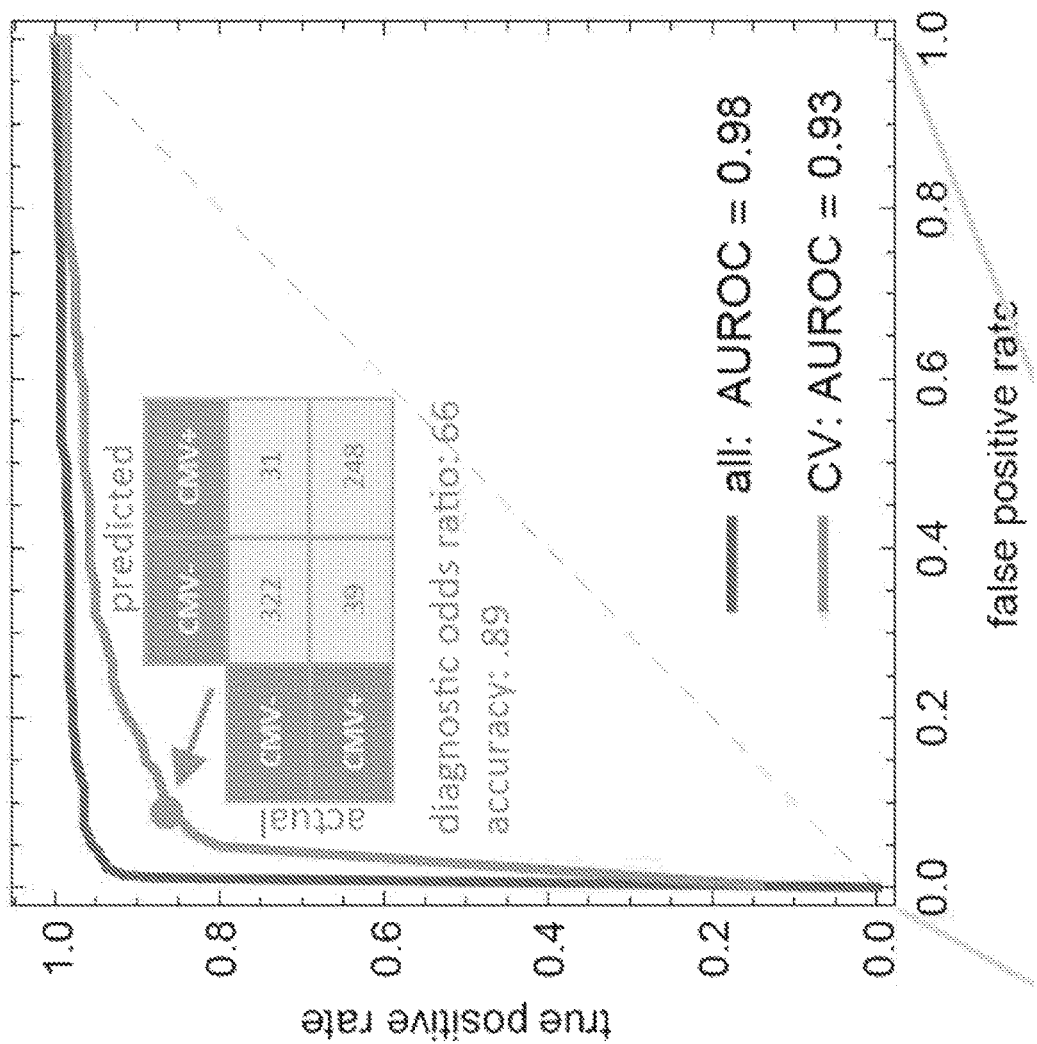
FIG. 9 shows the ROC curves for both the all and the cross-validation datasets.

The cross-validated results are shown in FIGS. 8 and 9 (shown for all subjects and cross-validated (CV) subjects). The accuracy of the model was shown to be at 89%, corresponding to a diagnostic odds ratio of ~66. Assessing model performance across the range of specificity vs. sensitivity using an ROC curve, an area under the ROC curve of 93% was achieved.

FIG. 8 (top graph) shows data for the classification performance of all and the cross-validation (CV) datasets for each p-value threshold, measured as the area under the ROC curve (AUROC). The number above each set of data points corresponds to the number of CMV-associated TCRβ identified at that p-value threshold, and the rectangle indicates the dataset selected for downstream analysis (p-value=$10^{-4}$).

FIG. 8 (bottom graph) also shows a false discovery rate (FDR) estimated for each p-value threshold used in the identification of significantly CMV-associated TCRβ sequences, using permutations of CMV status. The best performance is seen at a p-value of $10^{-4}$, which corresponds to an estimated FDR of ~20%, resulting in the identification of a set of 142 TCRβ sequences that were significantly associated with positive CMV status (listed in Table 1). Using these conditions resulted in a good separation between the CMV+ and CMV− subjects in the cohort as measured by CMV score (See FIG. 6).

FIG. 9 shows the ROC curves for both the all and the cross-validation datasets. The AUROC for the full dataset is 0.98, indicating that our approach resulted in an excellent classifier for CMV status. At the point of highest discriminating power, an accuracy of 0.89 and a diagnostic odds ratio of 66 in the cross-validation dataset was observed (achieved when classifying 86% of true positives correctly with a false positive rate of 8%). Taken together, these data suggest that presence of public T cell responses to CMV is highly correlated with CMV positive status.

Figure 10:
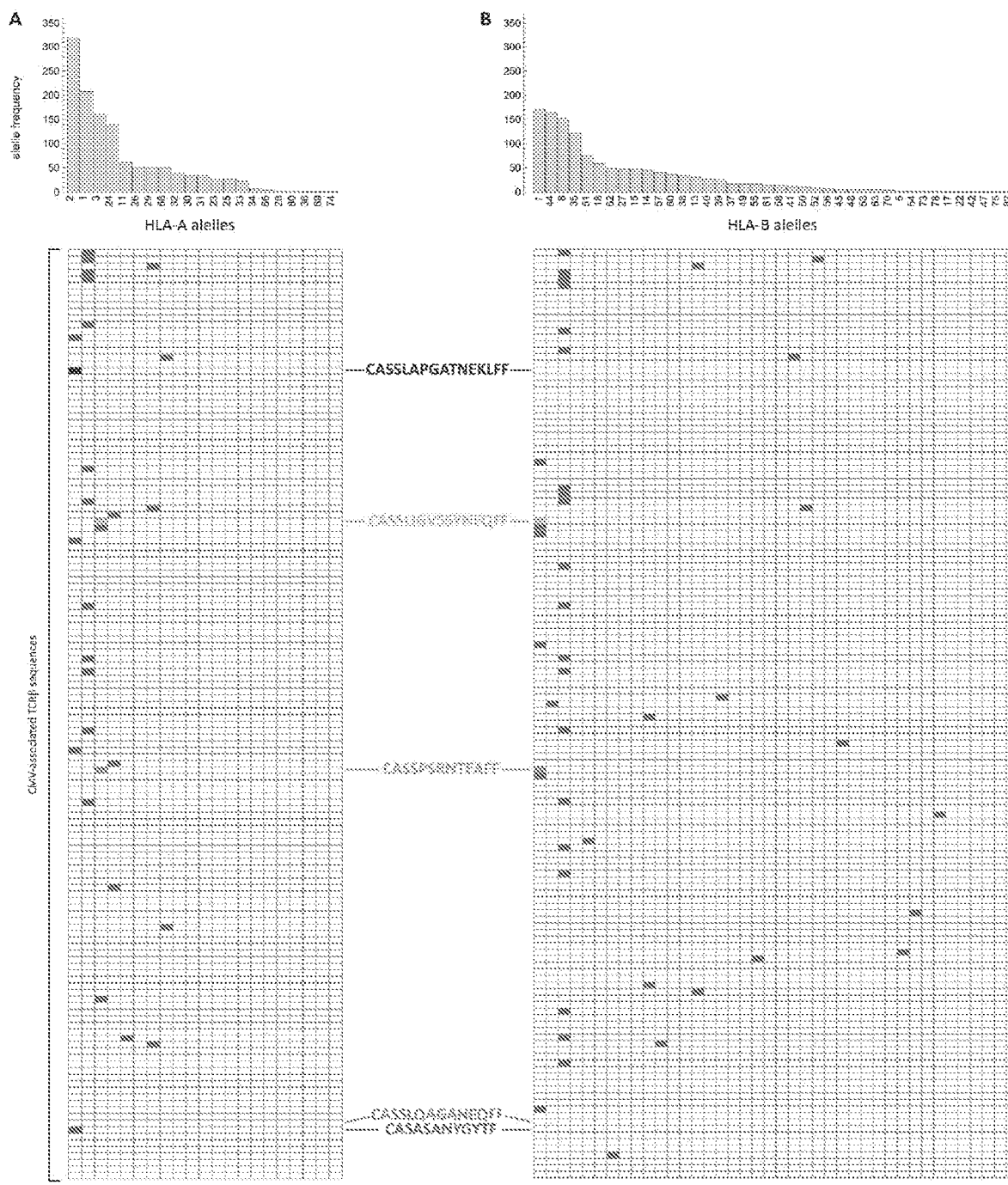
FIGS. 10A and 10B show HLA-restriction of CMV-associated TCRβ sequences.

Given that T cells recognize their cognate antigens in the context of MHC molecules expressed by antigen presenting cells, it was tested whether the HLA-restriction of our CMV-associated TCRβ sequences could be identified. A Fisher's exact test was performed on each CMV-associated TCRβ sequence to determine if its presence was significantly associated with any of the HLA alleles observed in the cohort. The association of 57 out of 142 CMV-associated TCRβ sequences could be confidently assigned with at least one HLA allele, with a p-value cutoff of $1\times10^{-3}$. Full results are presented in Table 1 (above) and FIG. 10.

FIGS. 10A and 10B show HLA-restriction of CMV-associated TCRβ sequences. FIG. 10A shows the distribution of HLA-A alleles in this cohort. FIG. 10B shows the distribution of HLA-B alleles in this cohort. Each of the 142 CMV-associated TCRβ sequences identified at $p\leq1\times10^{-4}$ was tested for significant association with each HLA allele, with a p-value threshold of $1\times10^{-3}$. Of these 142 CMV-associated TCRβ sequences, 57 were significantly associated with an HLA-A and/or an HLA-B allele, and no sequences were significantly associated with more than a single allele from each locus. Colored boxes and amino acid sequences indicate the 5 TCRβ sequences identified in our study that had been previously identified. In 4 of the cases, the correct HLA association was recapitulated, and in the $5^{th}$ case, there was no statistically-significant HLA association.

A literature search was performed to identify previously reported CMV-reactive TCRβ sequences, and 595 unique TCRβ sequences were selected that had been identified by at least one previously published study[3, 10, 12-27]. Of these, 30 unique TCRβ sequences had previously been previously classified as public, or were reported in multiple studies. It was determined that 5 of these 30 public TCRβ sequences unique were contained in the set of 142 CMV-associated TCRβ sequences. Furthermore, an HLA association was identified for 4 of these 5 TCRβ sequences, and in all 4 cases our HLA association agreed with the literature. FIGS. 11A, 11B, and 12 provide more complete information on the prevalence in our dataset of previously identified CMV-reactive TCRβ sequences, as described below.

FIGS. 11A and 11B show the incidence of previously reported CMV-reactive TCRβ sequences in this cohort. After a literature search, 565 'private' CMV-reactive TCRβ sequences (reported in one individual from a single study) and 30 'public' CMV-reactive TCRβ sequences (reported in multiple studies or in multiple individuals within a single study) were identified. FIG. 11A shows the incidence of each such TCRβ sequence in the cohort of 640 subjects plotted along the horizontal axis by decreasing total incidence, with the incidence in CMV+ subjects above the horizontal and the incidence in CMV− subjects below the horizontal. Many previously-reported sequences were observed in the dataset, but most were seen in roughly equal number of CMV+ and CMV− subjects, which could be explained by receptor sequences with exceptionally high frequency in the naïve repertoire, or could reflect cross-reactive receptors that bind to CMV antigens but also other common antigens. FIG. 11B shows a histogram of incidence of these TCRβ sequences in the cohort of 640 subjects plotted for each group of sequences. Most previously-reported CMV-reactive TCRβ sequences were found in our dataset at appreciable levels, though only a handful were found disproportionately in CMV+ subjects at $p \leq 1 \times 10^{-4}$. 'Public' TRβ sequences reported in the literature were considerably more common in our cohort.

FIG. 12 shows the concordance of TCRβ sequences in the cohort as compared to those in the literature. Of the 142 TCRβ sequences significantly associated with CMV status in the cohort with a p-value of less than $1 \times 10^{-4}$, five TCRβ sequences (defined by matching CDR3 amino acid sequence) have been previously reported in the literature as public clones. FIG. 12 provides the CDR3 amino acid sequence, V and J genes, and HLA association for each sequence and compares it to previous reports. As expected, the two sequences previously identified as public were seen in more subjects in our cohort than the three sequences previously reported only once. Concordance of V gene, J gene, and HLA allele association with those reported in the literature was very good. Five out of nine total comparisons had the same V gene, and the other 4 comparisons had the same V gene subfamily. There were concordant J genes in 9 out of 9 comparisons, and an identical HLA association in 8 out of 9 comparisons, with one sequence not significantly HLA-associated in this study.

Thus, immunosequencing can be used to determine CMV-specific T cell sequences in a large cohort and predict CMV status in new subjects with high accuracy. In summary, it has been demonstrated that information gleaned from rearranged T cell receptors can be used to infer disease status based on the presence of public T cell responses; the only requirement is a large sample of pathogen-positive and -negative samples with which to identify these public T cell responses. Because high-throughput sequencing of T cell receptors captures all T cell responses equally, and these store immunological memory to all pathogens in a common format, reading T cell memory by looking for known public responses can be a viable strategy for simultaneously diagnosing a wide range of infectious agents using a single peripheral blood sample and a simple, unified assay. These methods can be applied needed to acute infections, given that T cell memory persists for years, accounting for the fact that it is not known how public clones decay with time after an acute infection. Accordingly, this method can be used to assess multiple infections simultaneously, such as HPV, EBV, CMV and others. The method can also be used to predict or diagnose a non-infectious (e.g. autoimmune) disease.

The methods of the invention can also be used to quantify disease burden (e.g. CMV reactivation post-transplant).

Example 2: Identification of HLA Type

The first aim of the study was to create a comprehensive catalog of T cell receptor sequences and associated HLA types.

HLA Typing:

640 subjects were phenotyped for HLA type according to standard protocol by the Fred Hutchinson Cancer Research Center.

Immune Repertoire Sequencing:

Next, the TCRB sequences for each subject was determined by amplification and sequencing.

Genomic DNA was extracted from peripheral blood samples using the Qiagen DNeasy Blood extraction Kit (Qiagen, Gaithersburg, Md., USA). The CDR3 regions of rearranged TCRβ genes were sequenced; the TCRβ CDR3 region was defined according to the IMGT collaboration[28, 20]. TCRβ CDR3 regions were amplified and sequenced using methods described above and in previously described protocols[5, 29]. The multiplexed PCR method used a mixture of 60 forward primers specific to TCR Vβ gene segments and 13 reverse primers specific to TCR Jβ gene segments. The resulting amplicons were sequenced using the methods described above. Reads of 87 bp were obtained using the Illumina HiSeq System. Raw HiSeq sequence data were preprocessed to remove errors in the primary sequence of each read, and to compress the data. A nearest neighbor algorithm was used to collapse the data into unique sequences by merging closely related sequences, to remove both PCR and sequencing errors.

In order to ensure adequate coverage of each T cell rearrangement, 8-10× sequence coverage, or ~6-10 million sequencing reads per sample, was generated using approximately eight full sequencing runs. All sequencing reads were processed using a standardized bioinformatics pipeline to 1) demultiplex reads to specific samples, 2) eliminate low quality sequence and remove potential contaminants, 3) align and identify specific TCRB V and J gene segments and CDR3 regions, 4) cluster highly similar sequences to account for PCR and sequencing errors, 5) normalize data to remove PCR amplification bias, 6) estimate total T-cell input, and 7) generate TCRβ unique sequence counts and distributions.

Here, approximately 250,000 rearranged T cell receptor genes were sequenced from peripheral blood of each subject. For each subject, approximately $10^5$ TCRβ sequences were obtained, and the abundances of each unique sequence were quantified.

Feature Selection: To Define Association Between an HLA Allele and TCRB Sequence(s)

For each subject, the total number of unique TCRβ sequences and the frequency of each unique TCRβ sequence are determined. For a unique TCRβ sequence, it is determined how many subjects who are positive for an HLA allele have the TCRβ sequence and how many subjects who are negative for the HLA allele have the TCRβ sequence. In addition, it can be determined the number of subjects who are positive for an HLA allele and negative for the TCRβ sequence and the number of subjects who are negative for the HLA allele and positive for the TCRβ sequence. The table below shows categorization of subjects by the presence or absence of a TCRβ sequence and the presence or absence of an HLA allele, HLA-A2.

|  | HLA-A2+ | HLA-A2− |
|---|---|---|
| TCRβ sequence i present | $n_{i+}$ | $n_{i-}$ |
| TCRβ sequence i not present | $N_+ - n_{i+}$ | $N_- - n_{i-}$ |

FIG. 14 shows a list of exemplary unique TCRβ sequences and the number of subjects who are positive or negative for an HLA-A2 allele that have a particular TCRB sequence.

A p-value is determined for the association of each TCRβ sequence with an HLA status using a Fisher exact test (two-tailed). The p value for association of each TCR with allele status using a Fisher exact test (two tailed) is calculated as follows:

$$Pr(\text{table}) = \frac{\binom{n_+ + n_-}{n_+}\binom{N_+ + N_- - n_+ - n_-}{n_+ + n_-}}{\binom{N_+ + N_-}{N_+}}$$

FIG. 14 shows exemplary p values that were calculated for the association of a particular TCRβ sequence with an HLA type (HLA-A2).

As shown in FIG. 15, a p value is selected as a cutoff for identifying a set of "Feature TCRs" from the entire list of possible TCR sequences. Defining a p-value threshold and permuting the allele status across individuals provides an estimate of false discovery rate. This is performed for each HLA allele, resulting in a set of allele-associated TCRβ sequences for each HLA allele. In FIG. 15, a p value cutoff of p≤$10^{-4}$ and an FDR of 0.1 is used to identify 288 TCRβ sequences that are positively associated with HLA-A2. For each of the allele-associated TCRβ sequences, the frequency of the sequence is also determined in each subject.

As shown in FIG. 15, a p value is selected as a cutoff for identifying a set of "Feature TCRS" from the entire list of possible TCR sequences. Defining a p-value threshold and permuting the allele status across individuals provides an estimate of false discovery rate. This is performed for each HLA allele, resulting in a set of allele-associated TCRβ sequences for each HLA allele. In FIG. 15, a p value cutoff of p≤$10^{-4}$ and an FDR of 0.1 is used to identify 288 TCRβ sequences that are positively associated with HLA-A2. For each of the allele-associated TCRβ sequences, the frequency of the sequence is also determined in each subject.

The false discovery rate (FDR) was determined by permutation of allele status. See Storey et al. *Statistical significance for genomewide studies.* PNAS, 100 (6), pp. 9440-9445.

The feature selection step is followed by a machine learning process. As shown in FIG. 16, for each HLA allele, a logistic regression model is trained using the set of feature vectors over all subjects, along with the known status for presence of that allele.

As shown in FIG. 17, an exhaustive leave-one-out cross validation is performed where one subject is removed from the analysis, and the HLA status of the subject is inferred based on feature selection and training from only the remaining subjects. The result is a set of classifiers (one for each HLA allele) that estimate the probability of positive status for each HLA allele, taking as input the feature vector for each allele.

Equipped with these classifiers, the HLA type of a new subject can be assessed by: 1. immune repertoire sequencing, 2. computing feature vectors for each allele, and 3. defining a probability threshold for positive status that will be applied to the output from each classifier. In this manner, an HLA status can be inferred for a new subject with an unknown HLA status.

FIG. 18 shows the results of a cross validation study. The leave-one out cross validation was performed for 78 rounds. For the HLA-A2 allele, the method described above resulted in identification of 288 feature TCRs and an accurate prediction of 41 subjects out of 43 as HLA-A2 positive. As described above, the HLA type of the subjects was known prior to performing the cross validation. Only 2/43 subjects were false-positives for HLA-A2. Thus, the method was 96% accurate in predicting HLA-A2 presence in a subject based on the subject's TCRβ sequence profile.

FIG. 18 also shows the results for cross-validation of the HLA-A24 allele, which also had a 96% accuracy. 10 out of 13 subjects were accurately predicted to possess the HLA-A24 allele, and 65 out of 65 subjects were accurately predicted to as not have the HLA-A24 allele based on the identified TCRβ features.

Example 3: HLA Study

In another example, the public T-cell response to cytomegalovirus (CMV) was investigated by sequencing rearranged T cell receptors (TCRs) in 650 subjects (294 with and 356 without CMV). The concordance between ~90 million unique TCRs and CMV serostatus was assessed, focusing on identification of significant associations. In this study, 157 CMV-associated TCRs were identified at p≤$10^{-3}$, FDR 0.15) Training a binary classifier on these features, it was predicted that CMV serostatus in a leave-one-out cross-validation procedure had a diagnostic odds ratio of 44. The classifier was also tested on a second independent cohort of 120 subjects with known CMV serostatus, yielding a diagnostic odds ratio of 49.

Next, the HLA-restriction of each CMV-associated TCR was investigated by assessing the over-representation of particular HLA types among the subjects that carry each CMV-associated TCR. Of 157 CMV-associated TCRs, 61 were HLA-associated at p≤$10^{-3}$. None of these were significantly associated with multiple HLA-A or HLA-B alleles.

There was substantial concordance between our data and previously published CMV- and HLA-associated TCRs. Most previously-reported public CMV-specific TCRs were seen in the data, although only 5/157 CMV-associated TCRs identified in this study have been previously reported. Of these, 4 were significantly HLA-restricted, and all four confirmed previous findings.

In addition, the association of TCRs with each HLA-A allele present in the cohort was investigated, with significant (p≤$10^{-4}$) results for many higher frequency alleles. Binary classifier training resulted in high accuracy (~96%) prediction for these alleles, indicating that HLA type can be inferred from immunosequencing data.

In summary, this study demonstrated the validity of association studies using immunosequencing for detection and HLA-association of public T-cell responses to infection, and showed that assessing the presence of associated T-cell responses can serve as a powerful diagnostic classifier.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES

1. Neller, M. A., Burrows, J. M., Rist, M. J., Miles, J. J. & Burrows, S. R. High frequency of herpesvirus-specific clonotypes in the human T cell repertoire can remain stable over decades with minimal turnover. *J Virol* 87, 697-700 (2013).
2. Li, H., Ye, C., Ji, G. & Han, J. Determinants of public T cell responses. *Cell Res* 22, 33-42 (2012).
3. Venturi, V., Price, D. A., Douek, D. C. & Davenport, M. P. The molecular basis for public T-cell responses? *Nat Rev Immunol* 8, 231-238 (2008).
4. Arstila, T. P. et al. A direct estimate of the human alphabeta T cell receptor diversity. *Science* 286, 958-961 (1999).
5. Robins, H. S. et al. Comprehensive assessment of T-cell receptor beta-chain diversity in alphabeta T cells. *Blood* 114, 4099-4107 (2009).
6. Cabaniols, J. P., Fazilleau, N., Casrouge, A., Kourilsky, P. & Kanellopoulos, J. M. Most alpha/beta T cell receptor diversity is due to terminal deoxynucleotidyl transferase. *J Exp Med* 194, 1385-1390 (2001).
7. Davis, M. M. & Bjorkman, P. J. T-cell antigen receptor genes and T-cell recognition. *Nature* 334 (1988).
8. Robins, H. S. et al. Overlap and effective size of the human CD8+ T cell receptor repertoire. *Sci Transl Med* 2, 47ra64 (2010).
9. Li, H. et al. Recombinatorial biases and convergent recombination determine interindividual TCRbeta sharing in murine thymocytes. *J Immunol* 189, 2404-2413 (2012).
10. Venturi, V. et al. TCR beta-chain sharing in human CD8+ T cell responses to cytomegalovirus and EBV. *J Immunol* 181, 7853-7862 (2008).
11. Gandhi, M. K. & Khanna, R. Human cytomegalovirus: clinical aspects, immune regulation, and emerging treatments. *Lancet Infect Dis* 4, 725-738 (2004).
12. Babel, N. et al. Clonotype analysis of cytomegalovirus-specific cytotoxic T lymphocytes. *J Am Soc Nephrol* 20, 344-352 (2009).
13. Iancu, E. M. et al. Clonotype selection and composition of human CD8 T cells specific for persistent herpes viruses varies with differentiation but is stable over time. *J Immunol* 183, 319-331 (2009).
14. Khan, N., Cobbold, M., Keenan, R. & Moss, P. A. Comparative analysis of CD8+ T cell responses against human cytomegalovirus proteins pp65 and immediate early 1 shows similarities in precursor frequency, oligoclonality, and phenotype. *J Infect Dis* 185, 1025-1034 (2002).
15. Klarenbeek, P. L. et al. Deep sequencing of antiviral T-cell responses to HCMV and EBV in humans reveals a stable repertoire that is maintained for many years. *PLoS Pathog* 8, e1002889 (2012).
16. Klinger, M. et al. Combining next-generation sequencing and immune assays: a novel method for identification of antigen-specific T cells. *PLoS One* 8, e74231 (2013).
17. Koning, D. et al. In vitro expansion of antigen-specific CD8(+) T cells distorts the T-cell repertoire. *J Immunol Methods* 405, 199-203 (2014).
18. Miconnet, I. et al. Large TCR diversity of virus-specific CD8 T cells provides the mechanistic basis for massive TCR renewal after antigen exposure. *J Immunol* 186, 7039-7049 (2011).
19. Price, D. A. et al. Avidity for antigen shapes clonal dominance in CD8+ T cell populations specific for persistent DNA viruses. *J Exp Med* 202, 1349-1361 (2005).
20. Retiere, C. et al. Generation of cytomegalovirus-specific human T-lymphocyte clones by using autologous B-lymphoblastoid cells with stable expression of pp65 or IE1 proteins: a tool to study the fine specificity of the antiviral response. *J Virol* 74, 3948-3952 (2000).
21. Scheinberg, P. et al. The transfer of adaptive immunity to CMV during hematopoietic stem cell transplantation is dependent on the specificity and phenotype of CMV-specific T cells in the donor. *Blood* 114, 5071-5080 (2009).
22. Schub, A., Schuster, I. G., Hammerschmidt, W. & Moosmann, A. CMV-specific TCR-transgenic T cells for immunotherapy. *J Immunol* 183, 6819-6830 (2009).
23. Trautmann, L. et al. Selection of T cell clones expressing high-affinity public TCRs within Human cytomegalovirus-specific CD8 T cell responses. *J Immunol* 175, 6123-6132 (2005).
24. Wynn, K. K. et al. Impact of clonal competition for peptide-MHC complexes on the CD8+ T-cell repertoire selection in a persistent viral infection. *Blood* 111, 4283-4292 (2008).
25. Peggs, K. et al. Characterization of human cytomegalovirus peptide-specific CD8(+) T-cell repertoire diversity following in vitro restimulation by antigen-pulsed dendritic cells. *Blood* 99, 213-223 (2002).
26. Weekes, M. P., Wills, M. R., Mynard, K., Carmichael, A. J. & Sissons, J. G. The memory cytotoxic T-lymphocyte (CTL) response to human cytomegalovirus infection contains individual peptide-specific CTL clones that have undergone extensive expansion in vivo. *J Virol* 73, 2099-2108 (1999).
27. Lim, A. et al. Frequent contribution of T cell clonotypes with public TCR features to the chronic response against a dominant EBV-derived epitope: application to direct detection of their molecular imprint on the human peripheral T cell repertoire. *J Immunol* 165, 2001-2011 (2000).
28. Yousfi Monod, M., Giudicelli, V., Chaume, D. & Lefranc, M. P. IMGT/JunctionAnalysis: the first tool for the analysis of the immunoglobulin and T cell receptor complex V-J and V-D-J JUNCTIONs. *Bioinformatics* 20 Suppl 1, i379-385 (2004).
29. Carlson, C. S. et al. Using synthetic templates to design an unbiased multiplex PCR assay. *Nat Commun* 4, 2680 (2013).
30. Storey, J. D. & Tibshirani, R. Statistical significance for genomewide studies. *Proc Natl Acad Sci USA* 100, 9440-9445 (2003).

What is claimed is:

1. A method for predicting the presence or absence of a cytomegalovirus (CMV) infection in a subject of unknown infection status, the method comprising:
   a) performing amplification and high throughput sequencing of genomic DNA obtained from a sample comprising T cells obtained from the subject to determine a TCR profile comprising unique TCR CDR3 amino acid sequences;
   b) comparing the TCR profile with a database of previously identified diagnostic public T cell receptor sequences that are statistically significantly associated with CMV infection;
   c) generating a CMV burden score for the subject, wherein the CMV burden score is the proportion of unique TCR sequences in the profile of the subject that match the public TCR sequences in the database;
   d) inputting the calculated CMV burden score from c) into a logistic regression model, wherein the logistic regression models compares CMV burden and CMV infection status from a plurality of subjects of known CMV infection status;
   e) determining an estimated probability of CMV infection status of the subject as the output of logistic regression model; and
   f) predicting the presence or absence of a CMV infection in the subject based on the estimated probability of CMV infection status determined at step e).

2. The method of claim 1, wherein the database of public T cell sequences are determined to be statistically significantly associated with CMV infection by:
   a) obtaining unique TCR sequences from a group of subjects with CMV infection and a group of subjects without CMV infection;
   b) subjecting each unique TCR sequence to a one-tailed Fisher exact test based on presence or absence of each TCR sequence in subjects of known CMV infection status with the null hypothesis that each TCR sequence is no more common in subjects with a CMV infection than in subjects without a CMV infection;
   c) setting a nominal p value threshold;
   d) controlling false discovery rate (FDR) by permutation of CMV infection status in each subject to generate an empirical null distribution of p-values; and
   e) generating a database of T cell receptor sequences that are statistically significantly shared in subjects with CMV infection.

3. The method of claim 2, wherein the nominal p-value threshold is less than or equal to $1.0*10^{-4}$.

4. The method of claim 3, wherein the statistically identified unique TCR sequences that correlate with the presence or absence of CMV infection comprise SEQ ID NOs: 1-142.

5. The method of claim 1, wherein the step of determining TCR profile in step (b) comprises the steps of:
   a) amplifying rearranged nucleic acids encoding the TCR CDR3 region in a multiplex PCR reaction with a mixture of forward primers specific to TCR V gene segments and reverse primers specific to TCR J gene segments;
   b) sequencing reads of the amplified nucleic acids;
   c) processing the sequence reads to remove errors in the primary sequence of each read and to compress the data; and
   d) applying a nearest neighbor algorithm to collapse the data into unique sequences by merging closely related sequences to remove both PCR and sequencing errors.

6. The method of claim 1, further comprising determining an HLA association for each unique TCR sequence in the TCR profile.

7. The method of claim 6, wherein said TCR sequence is associated with an HLA-A and/or an HLA-B allele.

8. A method for predicting the presence or absence of an infection in a subject of unknown infection status, the method comprising:
    a) performing amplification and high throughput sequencing of genomic DNA obtained from a sample comprising T cells obtained from the subject to determine a TCR profile comprising unique CDR3 amino acid sequences;
    b) comparing the TCR profile with a database of previously identified diagnostic public T cell receptor sequences that are statistically significantly associated with the infection;
    c) generating a first score for the subject, wherein the first score is the proportion of unique TCR sequences in the profile of the subject that match the public TCR sequences in the database;
    d) inputting the first score from c) into an algorithm, wherein the algorithm compares the first score of the subject and the infection status from a plurality of subjects of known infection status;
    e) determining an estimated probability of infection status of the subject as the algorithm output; and
    f) predicting the presence or absence of an infection in the subject based on the estimated probability of infection status determined at step e).

9. The method of claim 8, wherein the infection is from a cytomegalovirus (CMV), an Epstein-Barr virus (EBV), or a Herpes Simplex Virus (HSV).

10. A method for predicting the presence or absence of one or more viral infections in a subject of unknown infection status, the method comprising:
    a) determining a profile of unique TCR sequences from a sample obtained from the subject;
    b) inputting the unique TCR sequences from a) into one or more algorithms, wherein the one or more algorithms are generated by determining at least $10^5$ unique TCR sequences from each of a plurality of subjects of known infection status for each of the one or more infections and statistically identifying unique TCR sequences that correlate with the presence or absence of each of the one or more infections, to generate a score predictive of the presence or absence of each of the one or more infections; and
    c) inputting the scores from step b) into a logistic regression model trained on each of the plurality of subjects of known infection status for each of the one or more infections to predict whether the subject is either positive or negative for each of the one or more infections.

11. The method of claim 10, wherein the one or more viral infections are from a cytomegalovirus (CMV), an Epstein-Barr virus (EBV), a Herpes Simplex Virus (HSV) or a small pox virus.

* * * * *

UNITED STATES PATENT AND TRADEMARK OFFICE
CERTIFICATE OF CORRECTION

| | | |
|---|---|---|
| PATENT NO. | : 11,047,008 B2 | Page 1 of 1 |
| APPLICATION NO. | : 15/553040 | |
| DATED | : June 29, 2021 | |
| INVENTOR(S) | : Ryan O. Emerson et al. | |

It is certified that error appears in the above-identified patent and that said Letters Patent is hereby corrected as shown below:

In the Specification

In Column 1, Line 40, "(MEW)" should read --MHC--.

In Column 9, Line 37, "*americans*" should read --*americanis*--.

Signed and Sealed this
Twenty-first Day of September, 2021

Drew Hirshfeld
*Performing the Functions and Duties of the*
*Under Secretary of Commerce for Intellectual Property and*
*Director of the United States Patent and Trademark Office*